US009486002B2

(12) United States Patent
Boghani et al.

(10) Patent No.: US 9,486,002 B2
(45) Date of Patent: Nov. 8, 2016

(54) CONFECTIONERY COMPOSITION INCLUDING AN ELASTOMERIC COMPONENT, A COOKED SACCHARINE COMPONENT, AND A FUNCTIONAL INGREDIENT

(75) Inventors: Navroz Boghani, Flanders, NJ (US); Petros Gebreselassie, Piscataway, NJ (US); Shiuh John Luo, Livingston, NJ (US); Kishor Kabse, Morris Plains, NJ (US)

(73) Assignee: INTERCONTINENTAL GREAT BRANDS LLC, East Hanover, NJ (US)

( * ) Notice: Subject to any disclaimer, the term of this patent is extended or adjusted under 35 U.S.C. 154(b) by 479 days.

(21) Appl. No.: 11/913,184

(22) PCT Filed: May 23, 2006

(86) PCT No.: PCT/US2006/019739
§ 371 (c)(1),
(2), (4) Date: Oct. 31, 2007

(87) PCT Pub. No.: WO2006/127603
PCT Pub. Date: Nov. 30, 2006

(65) Prior Publication Data
US 2008/0187621 A1  Aug. 7, 2008

Related U.S. Application Data

(60) Provisional application No. 60/683,634, filed on May 23, 2005, provisional application No. 60/792,556, filed on Apr. 17, 2006.

(51) Int. Cl.
| A23G 4/20 | (2006.01) |
| A23G 3/36 | (2006.01) |
| A23G 3/42 | (2006.01) |
| A23G 3/54 | (2006.01) |
| A23G 4/10 | (2006.01) |
| A23G 4/12 | (2006.01) |

(52) U.S. Cl.
CPC .................. *A23G 4/20* (2013.01); *A23G 3/364* (2013.01); *A23G 3/42* (2013.01); *A23G 3/54* (2013.01); *A23G 4/10* (2013.01); *A23G 4/12* (2013.01)

(58) Field of Classification Search
CPC ................................ A23G 4/20; A23G 3/364
See application file for complete search history.

(56) References Cited

U.S. PATENT DOCUMENTS

| 146,541 A | 1/1874 | Moore |
| 193,045 A | 7/1877 | Sibley et al. |
| 280,115 A | 6/1883 | Aubin |
| 1,242,562 A | 10/1917 | Laskey |
| 1,267,320 A | 5/1918 | Fries |
| 1,384,319 A | 7/1921 | Heath |
| 1,771,506 A | 7/1930 | Mustin |
| 1,771,981 A | 7/1930 | Mustin |
| 1,771,982 A | 7/1930 | Mustin |
| 1,855,670 A | 4/1932 | Greenwood |
| 2,215,575 A | 9/1940 | Bowman |
| 2,366,128 A | 12/1944 | Root et al. |
| 2,460,698 A | 2/1949 | Lindhe et al. |
| 2,559,648 A | 7/1951 | Lindhe et al. |
| 2,973,273 A | 2/1961 | Curtiss |
| 3,012,893 A | 12/1961 | Krenzner et al. |
| 3,062,662 A | 11/1962 | McDonald |
| 3,208,405 A | 9/1965 | Heggie et al. |
| 3,262,784 A | 7/1966 | Butcher et al. |
| 3,303,796 A | 2/1967 | Novissimo |
| 3,477,394 A | 11/1969 | Tidwell |
| 3,857,965 A | 12/1974 | Ream |
| 3,912,817 A | 10/1975 | Sapsowitz |
| 4,000,321 A | 12/1976 | Mochizuki et al. |
| 4,150,161 A | 4/1979 | Rudolph et al. |
| 4,157,402 A | 6/1979 | Ogawa et al. |
| 4,224,345 A | 9/1980 | Tezuka et al. |
| 4,254,149 A | 3/1981 | Rudolph et al. |
| 4,271,199 A | 6/1981 | Cherukuri et al. |
| 4,352,823 A | 10/1982 | Cherukuri et al. |
| 4,352,824 A | 10/1982 | Puglia et al. |
| 4,435,440 A | 3/1984 | Hough et al. |
| 4,485,118 A | 11/1984 | Carroll et al. |
| 4,491,596 A | 1/1985 | Elias |
| 4,496,592 A | 1/1985 | Kuwahara et al. |
| 4,497,846 A | 2/1985 | Boursier et al. |
| 4,515,769 A | 5/1985 | Merritt et al. |
| 4,601,907 A | 7/1986 | Knebl et al. |
| 4,614,654 A | 9/1986 | Ream et al. |
| 4,671,961 A | 6/1987 | Patel et al. |
| 4,724,151 A | 2/1988 | Mansukhani et al. |
| 4,726,953 A | 2/1988 | Carroll et al. |
| 4,740,376 A | 4/1988 | Yang |

(Continued)

FOREIGN PATENT DOCUMENTS

| EP | 1194042 B1 | 2/2003 |
| GB | 2 177 587 | 1/1987 |

(Continued)

OTHER PUBLICATIONS

U.S. Appl. No. 12/577,986, filed Oct. 13, 2009, Boghani, et al.
U.S. Appl. No. 11/913,188, filed Oct. 31, 2007, Boghani, et al.
U.S. Appl. No. 11/913,190, filed Oct. 31, 2007, Boghani, et al.
U.S. Appl. No. 11/926,550, filed Oct. 29, 2007, Kabse, et al.
Boomer Super Bubble Gum-Mango Jelly, Oct. 7, 2006.
Boomer Jelly Super Bubble Gum-Orange, Jan. 23, 2006.
Boomer Fresh Gel Super Bubble Gum—Lemon Mint, Jan. 23, 2006.
Wrigley's Doublement Chewing Gum-Gel, Oct. 3, 2005.
Boomer super Bubble Gum-Apple, Mar. 7, 2005.
Joyco Boomer Jelly Bubble Gum—Pineapple, Jun. 21, 2004.
Joyco Boomer Vampix Bubble Gum, Jun. 21, 2004.
Boomer Super Bubble Gum—Jelly Watermelon, Sep. 1, 2003.
Dunkin Max Bubble Gum with Tattoos—Apple; Cola; Strawberry, Mar. 26, 2001.

(Continued)

*Primary Examiner* — Jenna A Watts
(74) *Attorney, Agent, or Firm* — Cantor Colburn LLP

(57) ABSTRACT

The present invention relates to confectionery compositions including cooked saccharide, elastomeric component, and a functional ingredient.

26 Claims, 4 Drawing Sheets

(56) References Cited

U.S. PATENT DOCUMENTS

| | | | |
|---|---|---|---|
| 4,741,905 A | 5/1988 | Huzinec | |
| 4,753,806 A | 6/1988 | Carroll et al. | |
| 4,774,094 A | 9/1988 | Carroll et al. | |
| 4,792,453 A | 12/1988 | Reed et al. | |
| 4,800,095 A | 1/1989 | Carroll et al. | |
| 4,801,700 A | 1/1989 | Tully et al. | |
| 4,847,090 A | 7/1989 | Della Posta et al. | |
| 4,971,798 A | 11/1990 | Coia et al. | |
| 4,971,806 A | 11/1990 | Cherukuri et al. | |
| 4,981,698 A | 1/1991 | Cherukuri et al. | |
| 5,017,385 A | 5/1991 | Wienecke | |
| 5,108,763 A | 4/1992 | Chau et al. | |
| 5,139,798 A | 8/1992 | Yatka et al. | |
| 5,223,282 A | 6/1993 | Patel et al. | |
| 5,223,303 A * | 6/1993 | Taskinen | 426/660 |
| 5,376,389 A | 12/1994 | Reed et al. | |
| 5,437,879 A | 8/1995 | Kabse et al. | |
| 5,626,892 A | 5/1997 | Kehoe et al. | |
| 5,651,936 A | 7/1997 | Reed et al. | |
| 5,667,823 A | 9/1997 | Carroll et al. | |
| 5,855,631 A | 1/1999 | Leas | |
| 5,879,728 A | 3/1999 | Graff et al. | |
| 5,916,606 A | 6/1999 | Record et al. | |
| 5,958,472 A | 9/1999 | Robinson et al. | |
| 6,242,019 B1 * | 6/2001 | Bell et al. | 426/74 |
| 6,623,266 B2 | 9/2003 | Jani et al. | |
| 6,759,079 B2 | 7/2004 | Klug et al. | |
| 6,866,876 B2 | 3/2005 | Zuehlke et al. | |
| 7,390,518 B2 | 6/2008 | Gebreselassie et al. | |
| 7,955,630 B2 | 6/2011 | Boghani et al. | |
| 2002/0113632 A1 | 8/2002 | Yatka et al. | |
| 2002/0192329 A1 | 12/2002 | Corriveau et al. | |
| 2003/0134012 A1 | 7/2003 | Mederer | |
| 2003/0190387 A1 * | 10/2003 | Zuehlke et al. | 426/5 |
| 2003/0224087 A1 | 12/2003 | Lee | |
| 2005/0112236 A1 | 5/2005 | Boghani et al. | |
| 2005/0220867 A1 | 10/2005 | Boghani et al. | |
| 2005/0220934 A1 | 10/2005 | Leadbeater et al. | |
| 2006/0034975 A1 | 2/2006 | Schechner et al. | |
| 2006/0263413 A1 | 11/2006 | Boghani et al. | |
| 2006/0263472 A1 | 11/2006 | Boghani et al. | |
| 2006/0263473 A1 | 11/2006 | Boghani et al. | |
| 2006/0263477 A1 | 11/2006 | Boghani et al. | |
| 2006/0263478 A1 | 11/2006 | Boghani et al. | |
| 2008/0063747 A1 | 3/2008 | Boghani et al. | |
| 2008/0160138 A1 | 7/2008 | Boghani et al. | |
| 2008/0199564 A1 | 8/2008 | Boghani et al. | |

FOREIGN PATENT DOCUMENTS

| | | | |
|---|---|---|---|
| JP | 4 179 445 | 6/1992 | |
| JP | 2 796 425 | 6/1998 | |
| WO | 9500038 | 1/1995 | |
| WO | 97 06695 | 2/1997 | |
| WO | 9706695 | 2/1997 | |
| WO | 9952556 A1 | 10/1999 | |
| WO | 0069282 | 11/2000 | |
| WO | 0103513 A1 | 1/2001 | |
| WO | WO 0176383 A1 * | 10/2001 | A23G 3/00 |
| WO | 03/032744 | 4/2003 | |
| WO | 03068000 A1 | 8/2003 | |
| WO | 03084338 A1 | 10/2003 | |
| WO | 2005016022 A1 | 2/2005 | |
| WO | 2006127599 A2 | 11/2006 | |
| WO | 2006127600 A2 | 11/2006 | |
| WO | 2006127601 A2 | 11/2006 | |
| WO | 2006127602 A2 | 11/2006 | |
| WO | 2006127603 A2 | 11/2006 | |
| WO | 2006127604 A2 | 11/2006 | |
| WO | 2006127605 A2 | 11/2006 | |
| WO | 2007030011 A2 | 3/2007 | |
| WO | 02098240 A1 | 12/2012 | |

OTHER PUBLICATIONS

Joyco Chicle Dental Licor—del Polo Blanco Polor; del Polo Vitaminas+Calcio, Jul. 17, 2000.
Dunkin Bubble Gum—2 in 1 Transfer + Sticker; Round Container; Chewing Gum—Sugarfree.
Dunkin gum Lollipop—Looney Tunes, Jul. 10, 2000.
Boomer Active Bubblegum with Baking Soda—Mint; Stawberry, Sep. 6, 1999.
Super Pop'n Gum Fruit Flavoured Candy Pops—Fraise; Melon; Ananas; Peche, Jul. 5, 1999.
U.S. Appl. No. 11/913,188 Non-Final Office Action, notification date Apr. 7, 2011, 13 pages.
U.S. Appl. No. 11/913,190 Non-Final Office Action, notification date Mar. 31, 2011, 16 pages.
U.S. Appl. No. 11/913,190 Non-Final Office Action, notification date Sep. 30, 2011, 26 pages.
CN1513381 A, Abstract, Jul. 21, 2004, 1 page.
JP2006014739 A, Abstract, Jan. 19, 2006, 1 page.
Lee et al., "Sugar Confectionery and Chocolate Manufacture", 1973, pp. 4-5 and 332-339.
Mitchell (ed), Sweeteners and Sugar Alternatives in Food Technology, 2006, 2 pages.
Reduced Calorie Sweeteners: Isomalt, 1997, 4 pages.
Rowe et al. (eds), Handbook of Pharmaceutical Excipients, 4th ed, 2003, pp. 596-599.
U.S. Appl. No. 11/913,188 Final Office Action, notification date Oct. 28, 2011, 15 pages.
European Search Report and Office Action for European Application No. 07864591.8-2114, Dated Oct. 18, 2010, 5 pages.
International Preliminary Report on Patentability and Written Opinion for International Application No. PCT/US2007/085099, International Filing Date Nov. 19, 2007, Date of Mailing Apr. 8, 2008, 14 pages.
European Search Report for European Application No. 06770845.3-1221, dated Nov. 7, 2011, 8 pages.
U.S. Appl. No. 11/913,190 Final Office Action, filed Oct. 31, 2007, Notification Date May 11, 2012, 30 pages.
U.S. Appl. No. 11/926,550 Non-Final Office Action, filed Oct. 29, 2007, Notification Date May 10, 2012, 33 pages.
Non-Final Office Action for U.S. Appl. No. 11/913,190, filed Oct. 31, 2007, Date of Notification Jan. 10, 2013, 26 pages.
Final Office Action for U.S. Appl. No. 11/926,550, filed Oct. 29, 2007; Notification Date May 23, 2013, 31 pages.
Douglas P. Fritz, "Using Confectionery Equipment to Manufacture Chewing Gum." The Manufacturing Confectioner, Nov. 2000, pp. 45-48.
"New Twist for Gum Base", Candy Industry, May 1999, pp. 46 & 48.
Final Office Action for U.S. Appl. No. 11/926,550, filed Oct. 29, 2007, Notification Date May 21, 2014, 14 pages.
Non-Final Office Action for U.S. Appl. No. 11/926,550, filed Oct. 29, 2007, Notification Date Dec. 3, 2013, 22 pages.
International Search Report and Written Opinion; International Application No. PCT/US2006/019739; International Filing Date May 23, 2006; 8 pages.
EP Search Report and Written Opinion; Dated Nov. 3, 2011; Application No. 06770843.8; 10 pages.

* cited by examiner

CONFECTIONERY COMPOSITION INCLUDING AN ELASTOMERIC COMPONENT, A COOKED SACCHARINE COMPONENT, AND A FUNCTIONAL INGREDIENT

CROSS-REFERENCE TO RELATED APPLICATION

This application claims the benefit of U.S. provisional application 60/792,556 filed Apr. 17, 2006 and U.S. provisional application 60/683,634 filed May 23, 2005, both of which are incorporated herein by reference.

FIELD OF THE INVENTION

The present invention relates to confectionery compositions including cooked saccharide, an elastomeric component, and a functional ingredient. The compositions may have or may provide long lasting characteristics and/or variable textures. Optionally, components that create multi-modal effects are included in different portions of confectionery compositions.

BACKGROUND OF THE INVENTION

Some confectionery compositions where the finished product is formed by combining cooked saccharide syrups with chewing confectionery bases are known. For example, U.S. Pat. No. 4,741,905 discloses a chewing confectionery candy confection product produced from a process that combines a cooked sorbitol syrup with confectionery base. However, these compositions result in confectionery products that lack long lasting sensory characteristics and that have a narrow range of texture characteristics. Furthermore, these compositions have not been used to create multi-modal effects. Therefore, a need exists for confectionery compositions including cooked saccharide syrups and elastomeric components that demonstrate long lasting sensory attributes, offer a range of texture attributes, and/or provide multi-modal effects. There also exists a need for confectionery compositions that include cooked polyol syrups such as isomalt and elastomeric components.

SUMMARY OF THE INVENTION

Accordingly, one object of the present invention is to provide an edible composition comprising a cooked saccharide component; an elastomeric component; and a functional ingredient, flavors, food acids, sensates and sweeteners.

Another object of the present invention is to provide a confectionery composition, comprising a first portion, the first portion including a cooked saccharide component; and a second portion, the second portion including an elastomeric material; wherein the first portion comprises at least one first functional ingredient and the second portion comprises at least one second functional ingredient which is distinct from the at least one first functional ingredient, flavors, food acids, sensates and sweeteners.

Another object of the present invention is to provide a confectionery composition, comprising a first portion, the first portion including a cooked saccharide component; and a second portion, the second portion including an elastomeric material; wherein at least one of the first portion and the second portion comprises at least one first functional ingredient, flavors, food acids, sensates and sweeteners.

Another object of the present invention is to provide a confectionery composition, comprising a first portion, the first portion including a cooked sugar component; and a second portion, the second portion including an elastomeric material; wherein at least one of the first portion and the second portion comprises at least one first functional ingredient, flavors, food acids, sensates and sweeteners.

A more complete appreciation of the invention and many of the attendant advantages thereof will be readily obtained as the same becomes better understood by reference to the following detailed description when considered in connection with the accompanying drawings, wherein:

DETAILED DESCRIPTION OF THE INVENTION

Figure 1:
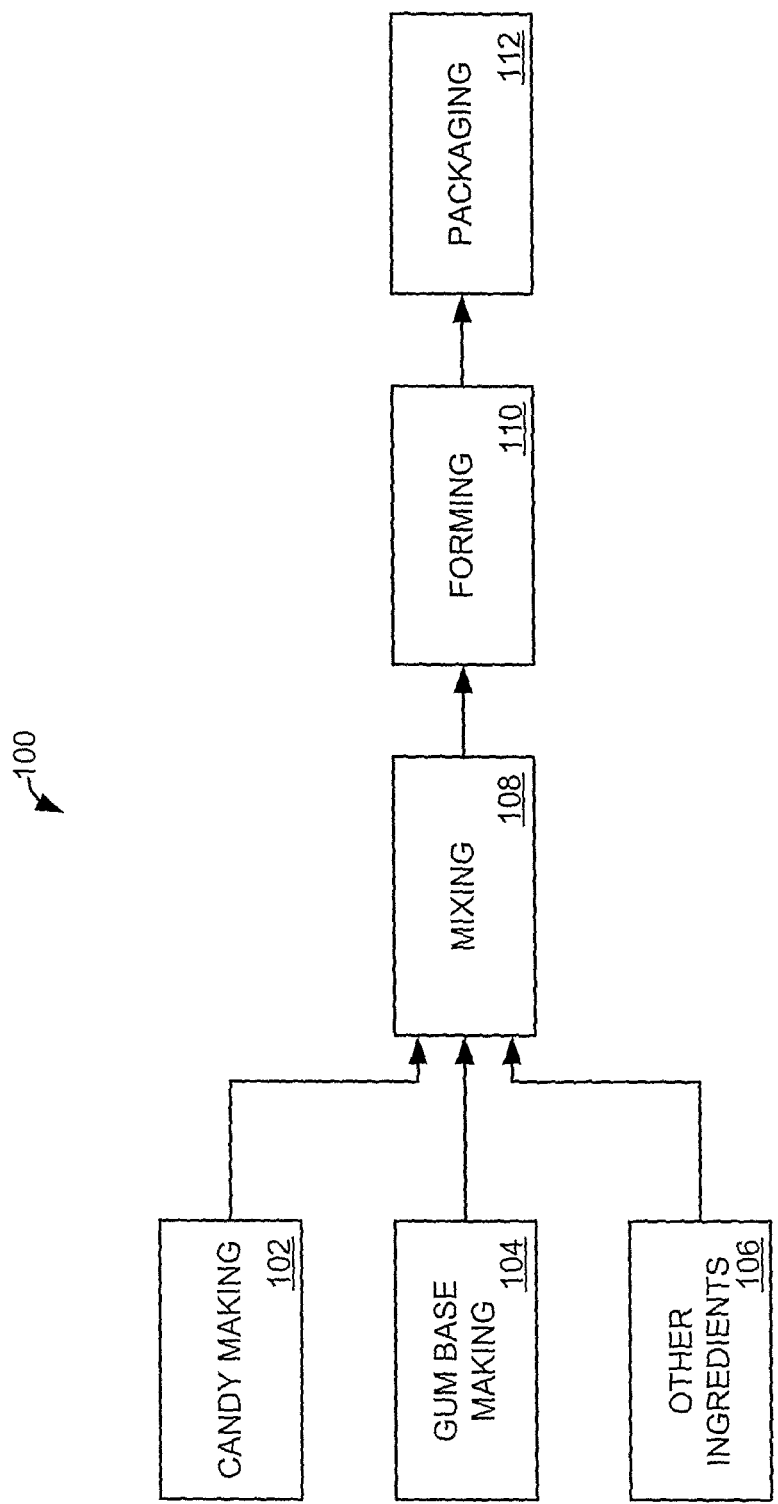
FIG. 1 shows a block diagram of a process for making confectionery compositions where candy and confectionery base, together with other ingredients such as flavor, color, etc., are mixed together and formed and then packaged.

Confectionery products are often consumed and enjoyed for their sensory characteristics including taste and texture attributes. Confectionery products can also be used to provide multi-modal effects and to deliver functional ingredients that provide consumer desired benefits. A prized attribute of confectionery products often is long lasting taste. Another desirable attribute is the product's texture profile including initial bite and hardness/softness over time. It can be desirable to provide consumers with interesting textures including those that provide a variety of textures such as an initial crispy texture followed by a soft chewing texture. Similarly, it can be desirable to provide consumers with products that provide a texture change or transformation such as textures that have an initial hardness similar to hard candy but then change to a chewy texture similar to chewing gum. However, economically producing confectionery products with interesting textures and long lasting sensory attributes remains a challenge because the technologies can be cost prohibitive. It has been found that confectionery compositions and processes allowing the use of confectionery equipment can alleviate the cost constraints through lower capital investment requirements thus making inclusion of long lasting sensory technologies possible. The result can be economically viable confectionery products with interesting textures and acceptable long lasting technology. A further finding has been that the long lasting technologies needed for confectionery compositions and processes that use confectionery equipment must be tailored to the demands of those compositions and processes. Yet another finding has been that incorporation of components in different portions of the confection can provide multi-modal effects.

In some embodiments, confectionery compositions including cooked polyol syrups and elastomeric components can contain erythritol, maltitol, lactitol, galactitol, isomalt, and combinations thereof as the cooked polyol syrup.

In other embodiments, confectionery compositions including cooked saccharide syrups and elastomeric components also include additional components such as sweeteners, functional ingredients, and combinations thereof. In still other embodiments, such confectionery compositions with additional components can include encapsulated additional components, unencapsulated additional components, or both. The encapsulated and unencapsulated additional components can be included in the cooked saccharide syrup, the elastomeric component, or both.

Additionally, in some embodiments, confectionery compositions including cooked saccharide syrups and elastomeric components include delivery systems. Such delivery systems can be included in the cooked saccharide syrup, the elastomeric component, or both. In some embodiments, the delivery systems can have tensile strengths of at least 6,500 psi. In some embodiments, the delivery systems can have water retentions of less than 15%.

In some embodiments, confectionery compositions can include texture modifying components. Such texture modifying components can include, but are not limited to, particulate materials, hydrophilic materials, flavoring materials, or combinations thereof.

Embodiments described herein provide a multi-component composition that includes at least one cooked saccharide portion and an elastomeric portion (e.g. gum base or chewing gum including a gum base). An individual piece of the confectionery composition may also include an outer coating or shell and/or an inner center-fill component. At least two components that create a dual perception upon consumption may be included in different portions of the piece of the confectionery composition. The individual pieces may form a variety of shapes including pellet, tablet, ball, pillow, chunk, stick, lollipop, and slab, among others. Further, in some embodiments, a confectionery composition can be in a particulate form. For example, in some embodiments, grinding the confectionery composition can create a particulate form. In still other embodiments, the grinding operation proceeds under ambient conditions. In some embodiments, a confectionery composition in particulate form is in a compressible form.

As used herein, the terms "first portion" and "cooked saccharide syrup" or "candy portion" are used interchangeably to refer to the portion of the compositions comprising saccharides and other optional ingredients.

As used herein, the terms "second portion" and "elastomeric portion" are used interchangeably to refer to a portion of the compositions comprising water insoluble polymers and other optional ingredients. In some embodiments, the second portion may contain, but is not limited to, elastomers, bulking agents, waxes, elastomer solvents, emulsifiers, plasticizers, fillers, and mixtures thereof.

As used herein, the term "gum base" refers to water insoluble material(s) and can include, but is not limited to, elastomers, bulking agents, waxes, elastomer solvents, emulsifiers, plasticizers, fillers, and mixtures thereof.

As used herein, the term "confectionery composition" and "confection" are used interchangeably to refer to the combination of at least one cooked saccharide syrup with at least one elastomeric portion.

As used herein, the term "delivery system" includes an encapsulating material and at least one ingredient encapsulated with the encapsulating material. In some embodiments, a delivery system may include multiple ingredients, multiples layers or levels of encapsulation, and/or one or more other additives. A delivery system may be an ingredient or component in a confectionery composition. In some embodiments, the one or more ingredients and an encapsulating material in the delivery system may form a matrix. In some embodiments, the encapsulating material may completely coat or cover the one or more ingredients or form a partial or complete shell, cover, or coating around the one or more ingredients.

As used herein, the term "tensile strength" includes the maximum stress a material subjected to a stretching load can withstand without tearing. A standard method for measuring tensile strength of a given substance is defined by the American Society of Testing Materials in method number ASTM-D638.

As used herein, the term "encapsulating material" includes any one or more water insoluble polymers, co-polymers, or other materials capable of forming a coating, shell, or film as a protective barrier or layer around one or more ingredients and/or capable of forming a matrix with the one or more ingredients. In some embodiments, the encapsulating material may completely surround, coat, cover, or enclose an ingredient. In other embodiments, the encapsulating material may only partially surround, coat, cover, or enclose an ingredient.

As used herein the transitional term "comprising," (also "comprises," etc.) which is synonymous with "including," "containing," or "characterized by," is inclusive or open-ended and does not exclude additional, unrecited elements or method steps, regardless of its use in the preamble or the body of a claim.

As used herein, the terms "bubble gum" and "chewing gum" are used interchangeably and are both meant to include any confectionery compositions.

As used herein, the term "ingredient" and the term "component" are used interchangeably to describe any additive, fixing, substance, material, agent, active, element, or part that may be included in the confectionery compositions of some embodiments.

As used herein, the term "duality" or "dual perception" refers to the perception by an individual of two characteristics that are complementary to each other, opposed to each other, i.e., distinct, or different in intensity from each other. The dual characteristics may be flavors, sensations, tastes or functionalities. Flavors, sensates, tastants and functional agents also may include compounds that potentiate each of these types of components.

The term "multi-modality" refers to the perception by an individual of at least two characteristics that are complementary, opposed, i.e., distinct, or different in intensity from one another. The multi-modal characteristics may be flavors, sensations, tastes, functionalities or combinations thereof. Flavors, sensates, tastants and functional agents also may include compounds that potentiate each of these types of components. The term "multi-modality" is broader than and encompasses the term "duality" in that it includes embodiments that have a dual perception, as well as embodiments that have more than one dual perception. For example, multi-modality may encompass two different dualities in one confectionery composition, such as dual flavors and dual tastes.

The term "complementary" refers to components that are in the same or similar flavor family, for example, the mint family or the fruit family; or components that are in the same or similar sensation family, for example, the cooling family, the warming family or the tingling family; or components that are in the same or similar taste family, for example, the sweetener family, the sour family, the bitter/astringent family, the salty family, the umami family or the kokumi family; or components that are in the same or similar functional family, for example, the breath freshening family or other functional families provided in Table 2 herein. The terms "family" and "type" are used interchangeably herein when referring to multi-modality components.

The term "opposed" means distinctly different components, for example, components that are from different families, such as a component in the flavor family and a component in the taste family.

The term "different in intensity" means that the at least two components that form the duality or multi-modality may be the same component but create the duality or multi-modality by being present in different amounts or by being encapsulated thereby providing a different intensity from one another. This different intensity can be formed by the component being in different amounts from one portion of the confectionery to another, or from being released at one rate in one portion versus being released at another rate in another portion. The different intensity can also be formed by the component interacting with the composition of a portion to provide a different intensity such as when a component has a low affinity for a portion's composition and therefore releases fully to provide a higher intensity at an amount lower than the amount needed to provide that same intensity from a portion where the component has a greater affinity for the portion's composition and is therefore less fully released.

Referring to the figures, FIG. 1 shows an illustrative confectionery production system 100 including a candy making system 102 and a gum base making system 104 which feed into a mixing operation 108 along with other ingredients 106. Upon exiting the mixing operation 108, the product proceeds to a forming operation 110 and finishes with a packaging operation 112.

Figure 2:
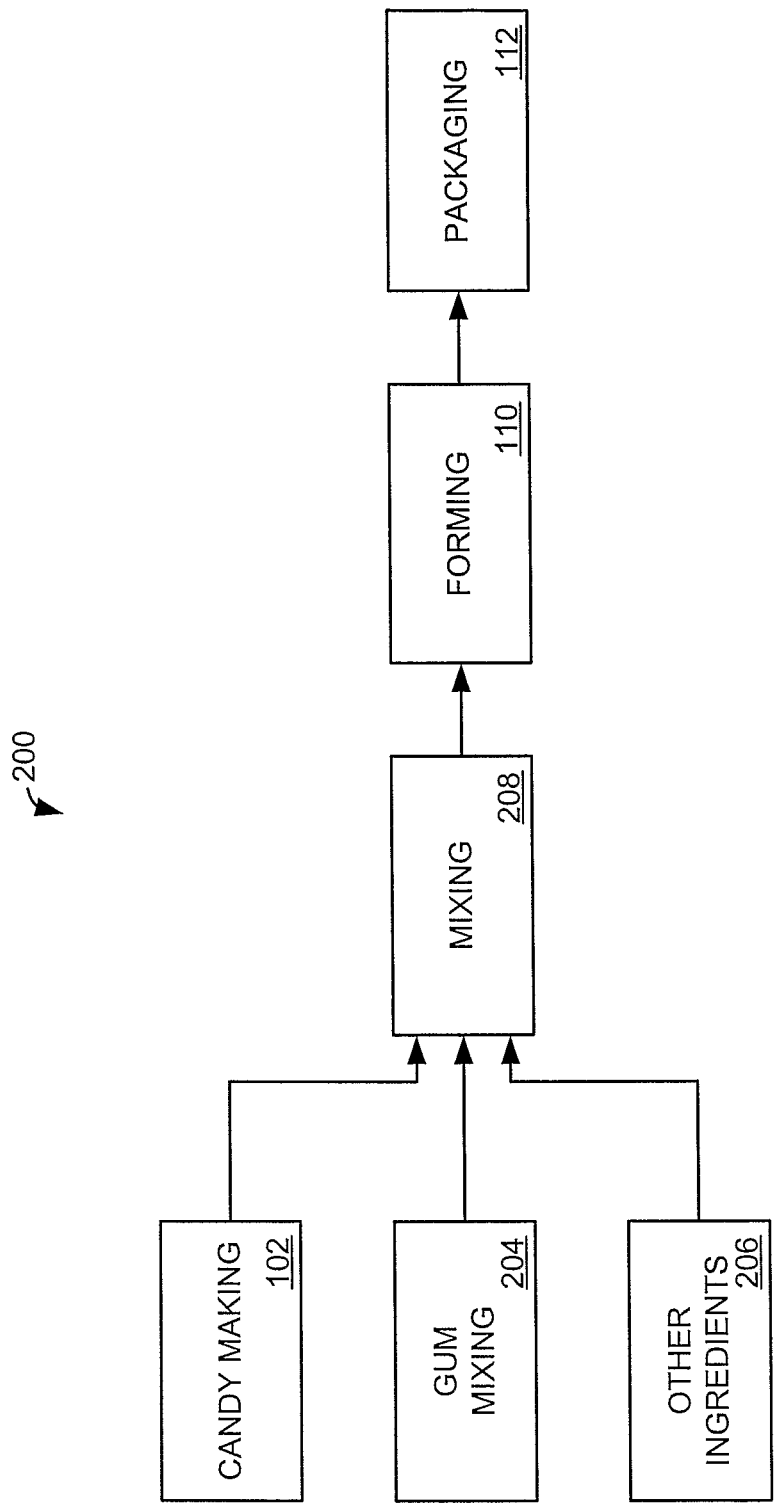
FIG. 2 shows a block diagram of a process for making confectionery compositions where candy and chewing confectionery, together with other ingredients such as flavor, color, etc., are mixed together and formed and then packaged.

An alternative confectionery production system 200 is shown in FIG. 2. This system includes a candy making system 102 and a confectionery mixing system 204 which feed into a mixing operation 208 together with other ingredients 206. In this alternative system, the confectionery mixing operation 204 could incorporate chewing confectionery ingredients such as bulk sweeteners, flavors, colors, etc. prior to being feed into the mixing operation in 208. By contrast, the system 100 in FIG. 1 includes a gum base making system 104 which could result in ingredients such as bulk sweeteners, flavors, colors, etc. being incorporated into the composition in the mixing system 108.

Figure 3:
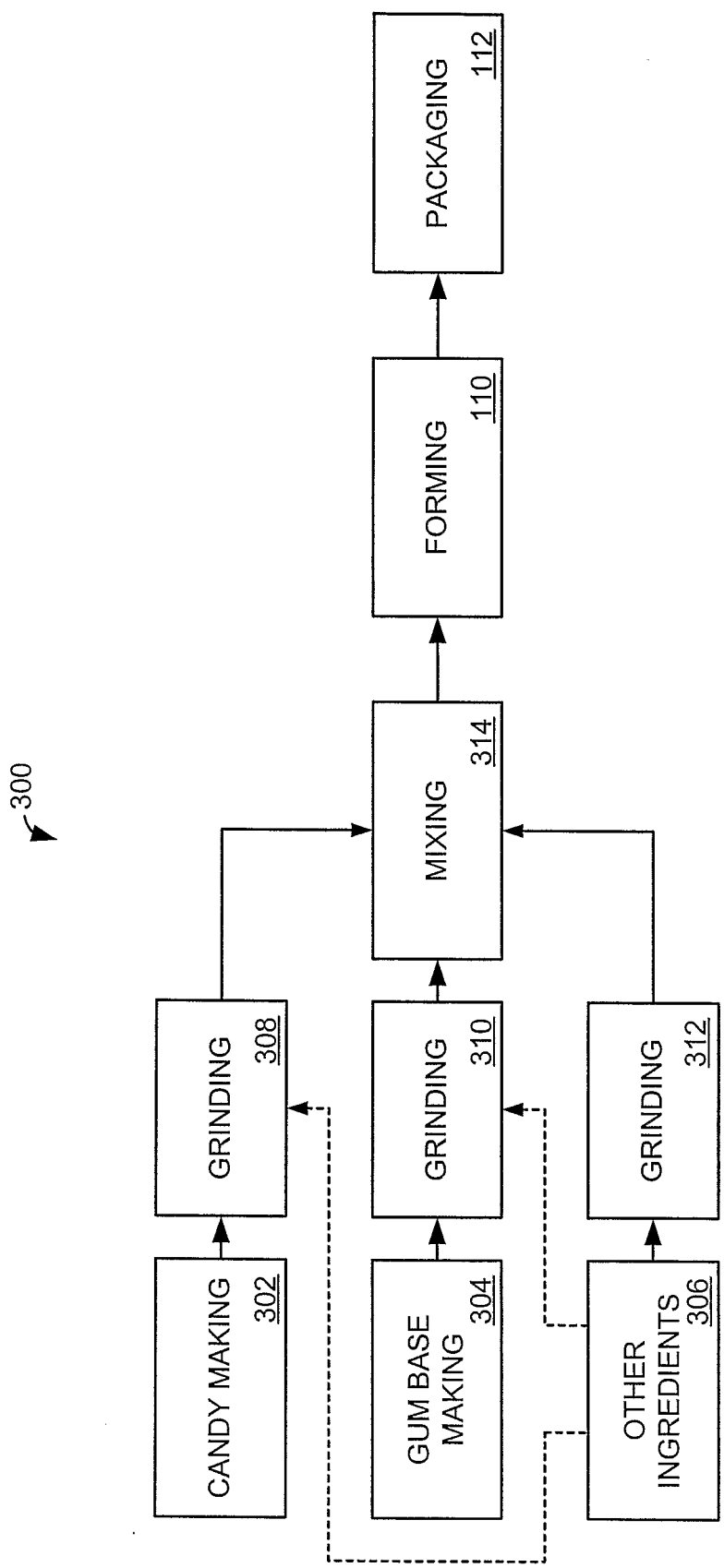
FIG. 3 shows a block diagram of a process for making confectionery compositions where candy and confectionery base, together with other ingredients are ground to particulate form before being mixed together and formed and then packaged.

FIG. 3 shows another illustrative confectionery production system 300 including a candy making system 302 which proceeds to a grinding operation 308 where the candy is reduced to particulate form before being fed into a mixing operation 314. Additionally, the confectionery production system 300 includes a gum base make making operation 304 which proceeds to a grinding operation 310 where the gum base is reduced to particulate form before being fed into the mixing operation 314. Also, other ingredients 306 proceed to a grinding operation 312 before being fed into the mixing operation 314. Optionally, as shown by dotted lines in FIG. 3, other ingredients 306 could also be fed into the grinding operations 308, or 310, or both/all. Upon exiting the mixing operation 314, the confectionery composition proceeds to a forming operation 110 and finishes with a packaging operation 112.

Figure 4:
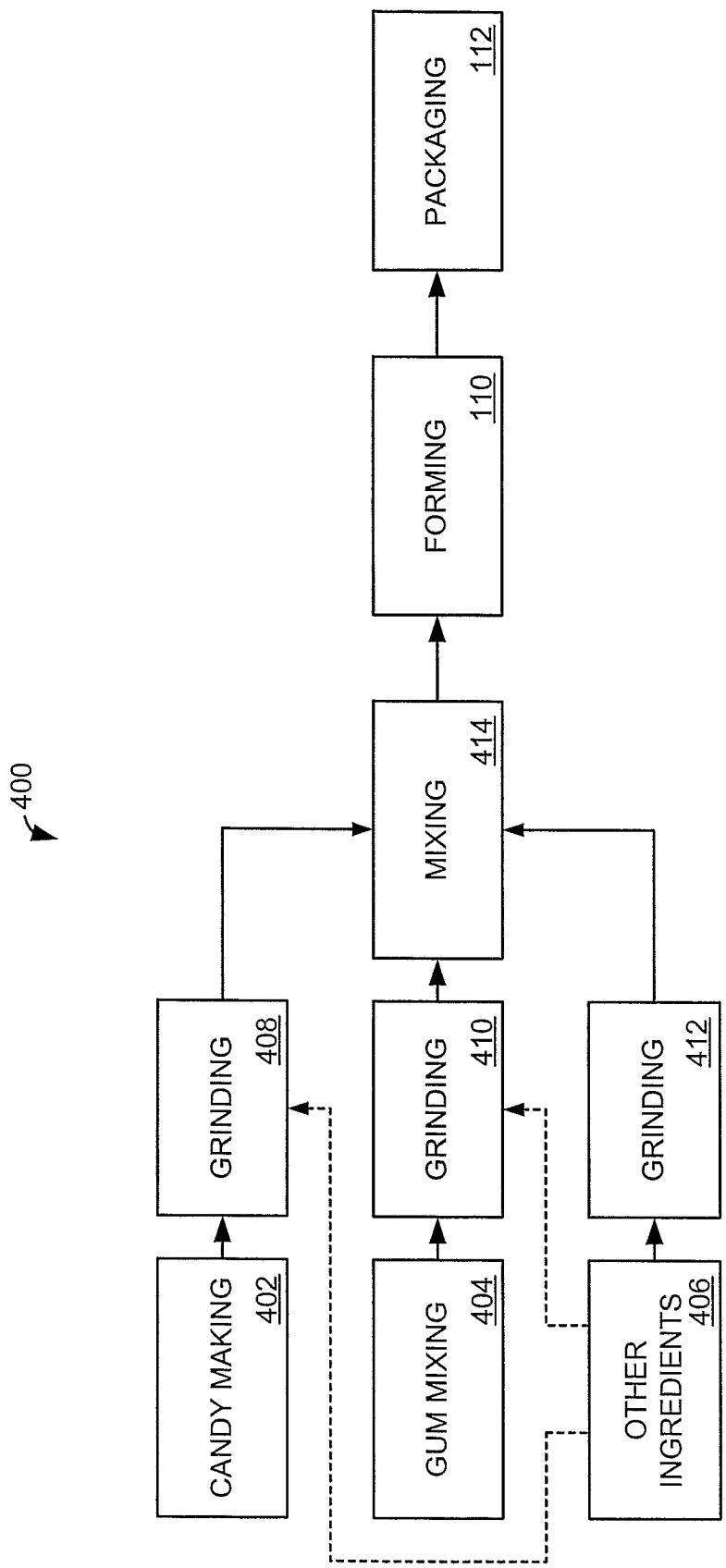
FIG. 4 shows a block diagram of a process for making confectionery compositions where candy and chewing confectionery, together with other ingredients are ground to particulate form before being mixed together and formed and then packaged.

FIG. 4 shows another illustrative confectionery production system 400 including a candy making system 402 which proceeds to a grinding operation 408 where the candy is reduced to particulate form before being fed into a mixing operation 414. Additionally, the confectionery production system 400 includes a chewing confectionery mixing operation 404 which proceeds to a grinding operation 410 where the chewing confectionery is reduced to particulate form before being fed into the mixing operation 414. In this alternative to the confectionery production system 300 in FIG. 3, chewing confectionery ingredients such as bulk sweeteners, flavors, colors, etc. could be added to the confectionery mixing system 404 prior to being fed into the mixing operation in 414. By contrast, the system in FIG. 3 includes a gum base making system 304 which could result in ingredients such as bulk sweeteners, flavors, colors, etc. being incorporated into the composition in the mixing system 314. Optionally, as shown by dotted lines in FIG. 4, other ingredients 406 could also be fed into the grinding operations 408, or 410, or both/all. Upon exiting the mixing operation 414, the confectionery composition proceeds to a forming operation 110 and finishes with a packaging operation 112.

Overview

In some embodiments, there is an edible composition comprising a cooked saccharide syrup and a chewing gum base, wherein the cooked saccharide syrup includes a polyol selected from the group consisting of maltitol, erythritol, isomalt or combinations thereof. In some embodiments, the edible composition also contains a high intensity sweetener that can be added to either the cooked saccharide syrup, the chewing gum base or both. In still further embodiments, the high intensity sweetener can be in an encapsulated form, a free form, or both. In some embodiments, the edible composition can include a delivery system. In other embodiments, the delivery system can have a tensile strength of at least 6,500 psi while in still other embodiments, the delivery system can have a water retention value to less than 15%.

In some embodiments, the edible composition comprises a texture modifying component. In some embodiments, the texture modifying component can include sorbitol, fat, flavor, or combinations thereof.

In some embodiments, the edible composition can include a center-fill, an exterior coating, or both.

In some embodiments, the edible composition can include at least one sensate. In other embodiments, at least one portion of the at least one sensate can be mixed with the cooked saccharide syrup, the gum base, or both. In still other embodiments, the at least one sensate can be in encapsulated form, in free form, or both.

In some embodiments, the edible composition can include at least one flavor. In other embodiments, at least one portion of the at least one flavor can be mixed with the cooked saccharide syrup, the gum base, or both. In still other embodiments, the at least one flavor can be in encapsulated form, in free form, or both.

In some embodiments, the edible composition can include at least one functional ingredient. In other embodiments, at least one portion of the at least one functional ingredient can be mixed with the cooked saccharide syrup, the gum base, or both. In still other embodiments, the at least one functional ingredient can be in encapsulated form, in free form, or both.

In some embodiments, the edible composition can include at least one sweetener. In other embodiments, at least one portion of the at least one sweetener can be mixed with the cooked saccharide syrup, the gum base, or both. In still other embodiments, the at least one sweetener can be in encapsulated form, in free form, or both.

In some embodiments, the cooked saccharide syrup and the gum base are visually distinct.

In some embodiments, there is provided an edible composition comprising a cooked component, wherein the cooked component includes isomalt; a gum base component; a multiple encapsulation sucralose composition, wherein said multiple encapsulation sucralose composition further comprises sucralose, a first encapsulation forming a first layer, and a second encapsulation forming a second layer; wherein the first layer encapsulates the sucralose and the second layer encapsulates the first layer; wherein the first encapsulation comprises polyvinyl acetate and the second encapsulation is selected from the group consisting of gum arabic, gelatin, or combinations thereof; and wherein the multiple encapsulation sucralose is added to the gum base component.

In some embodiments, there is provided an edible composition comprising a cooked saccharide component; a gum base component; and a functional ingredient. In some embodiments, the functional ingredient can be added to the cooked saccharide component or to the gum base component, or to both. In still other embodiments, the cooked saccharide component includes isomalt.

In some embodiments, there is provided an edible composition comprising a cooked saccharide component; a gum base component; a first flavor component; and a second flavor component. In some embodiments, the first flavor component can be added to the cooked saccharide component while the second flavor component can be added to the gum base component. In still other embodiments, the cooked saccharide component includes isomalt.

In some embodiments, there is provided an edible composition comprising a chewing gum base and a cooked saccharide syrup, wherein said cooked saccharide syrup has a moisture content of no more than 2% w/w, and wherein said chewing gum base and said cooked saccharide syrup are designed to withstand vigorous mixing without the incorporation of air into the mixture such that a homogeneous mixture of the chewing gum base and the cooked saccharide syrup results. In some embodiments, the chewing gum base is 10%-90% w/w of the edible composition while in other embodiments, the cooked saccharide syrup is 10%-90% w/w of the edible composition. In some embodiments, the amounts of cooked saccharide syrup and gum base are selected to provide a desired texture.

In some embodiments, the edible composition has an initial crunch that is the same as the initial crunch of a hard panned confection as measured by sensory testing techniques. In some embodiments, the composition has a surface gloss appearance that is the same as the surface gloss appearance of a hard panned product as measured by optometric equipment.

In some embodiments, at least a portion of the edible composition is in a ground particulate form. In other embodiments, at least a portion of the particulate composition is in compressible form.

In some embodiments, the edible composition includes a first flavor in the gum base and a second flavor in the cooked saccharide syrup. In some embodiments, the first flavor is the same as the second flavor while in other embodiments, the first flavor is different than the second flavor. In still other embodiments, the first flavor and the second flavor have different intensities as measured by sensory evaluation techniques.

In some embodiments, the gum base portion and the cooked saccharide portion are adjusted to be visually different.

In some embodiments, the chewing gum base contains a first ingredient and the cooked saccharide syrup contains a second ingredient. In some embodiments, the first ingredient and the second ingredient are the same while in other embodiments, the first ingredient is different from the second ingredient. In still other embodiments, the first ingredient and the second ingredient are more stable when separated than they would be if combined in the gum base or in the cooked saccharide syrup. In other embodiments, the first ingredient and the second ingredient operate together during consumption of the edible composition to provide a benefit.

In some embodiments, there is provided an edible composition comprising a chewing gum base and a cooked polymer syrup wherein the cooked polyol syrup is selected from the group consisting of isomalt, erythritol, lactitol, galactitol, and combinations thereof. In other embodiments, the edible composition further comprises a sugar component.

In some embodiments, there is provided a confectionery composition, comprising:
  a first portion, the first portion including a cooked saccharide component; and a second portion, the second portion including an elastomeric material; wherein the first portion comprises at least one first flavor and the second portion comprises at least one second flavor which is distinct from the at least one first flavor.

In some embodiments, there is provided a confectionery composition, comprising:
  a first portion, the first portion including a cooked saccharide component; and a second portion, the second portion including an elastomeric material; wherein the first portion comprises at least one first sensate and the second portion comprises at least one second sensate which is distinct from the at least one first sensate.

In some embodiments, at least a portion of the first sensate or the second sensate is encapsulated. In other embodiments, the first sensate or the second sensate includes at least one cooling agent.

In some embodiments, there is provided a confectionery composition, comprising:
  a first portion, the first portion including a cooked saccharide component; and a second portion, the second portion including an elastomeric material; wherein the first portion comprises at least one first food acid and the second portion comprises at least one second food acid which is distinct from the at least one first food acid.

In some embodiments, there is provided a confectionery composition, comprising:
  a first portion, the first portion including a cooked saccharide component; and a second portion, the second portion including an elastomeric material; wherein the first portion comprises at least one first functional ingredient and the second portion comprises at least one second functional ingredient which is distinct from the at least one first functional ingredient.

In some embodiments, the first or second functional ingredient is selected from the group comprising breath fresheners, dental care components, actives, herbals, effervescing systems, appetite suppressors, vitamins, micronutrients, mouth moistening components, throat care components, energy boosting agents, concentration boosting agents, and combinations thereof.

In some embodiments, there is provided a confectionery composition, comprising:
 a first portion, the first portion including a cooked saccharide component; and a second portion, the second portion including an elastomeric material; wherein the first portion comprises at least one first sweetener and the second portion comprises at least one second sweetener which is distinct from the at least one first sweetener.

In some embodiments, at least a portion of the at least one first sweetener or at least a portion of the at least one second sweetener are encapsulated. In still other embodiments, the first portion or the second portion also contain at least one sweetener potentiator. In some embodiments, at least a portion of the sweetener potentiator is encapsulated.

In some embodiments, there is provided a confectionery composition, comprising:
 a first portion, the first portion including a cooked saccharide component; and a second portion, the second portion including an elastomeric material; wherein at least one of the first portion or the second portion comprises at least one modified release component.

In some embodiments, the modified release component includes at least one ingredient selected from the group consisting of flavors, sweeteners, sensates, breath fresheners, dental care components, actives, herbals, effervescing systems, appetite suppressors, potentiators, food acids, micronutrients, mouth moistening components, throat care components, and combinations thereof.

In some embodiments, the confectionery composition further includes a center-fill material. In still other embodiments, the confectionery composition further includes a coating.

In some embodiments, there is provided a confectionery composition, comprising:
 a first portion, the first portion including a cooked saccharide component; and a second portion, the second portion including an elastomeric material; wherein at least one of the first portion and the second portion comprises at least one first flavor.

In some embodiments, the confectionery composition further includes a center-fill material. In still other embodiments, the confectionery composition further includes a coating.

In some embodiments, there is provided a confectionery composition, comprising:
 a first portion, the first portion including a cooked saccharide component; and a second portion, the second portion including an elastomeric material; wherein at least one of the first portion and the second portion comprises at least one first sensate.

In some embodiments, the at least one sensate comprises at least one cooling agent, warming agent, or tingling agent. In still other embodiments, at least a portion of the first sensate is encapsulated while in other embodiments, at least a portion of the at least one first sensate is unencapsulated.

In some embodiments, there is provided a confectionery composition, comprising:
 a first portion, the first portion including a cooked saccharide component; and a second portion, the second portion including an elastomeric material; wherein at least one of the first portion and the second portion comprises at least one first food acid.

In some embodiments, at least a portion of the at least one first food acid is encapsulated while in other embodiments, at least a portion of the at least one first food acid is unencapsulated.

In some embodiments, there is provided a confectionery composition, comprising:
 a first portion, the first portion including a cooked saccharide component; and a second portion, the second portion including an elastomeric material; wherein at least one of the first portion and the second portion comprises at least one first functional ingredient.

In some embodiments, at least a portion of the at least one first functional ingredient is encapsulated while in other embodiments, at least a portion of the at least one first functional ingredient is unencapsulated. In other embodiments, the at least one first functional ingredient is selected from the group comprising breath fresheners, dental care components, actives, herbals, effervescing systems, appetite suppressors, vitamins, micronutrients, mouth moistening components, throat care components, energy boosting agents, concentration boosting agents, and combinations thereof.

In some embodiments, there is provided a confectionery composition, comprising:
 a first portion, the first portion including a cooked saccharide component; and a second portion, the second portion including an elastomeric material; wherein at least one of the first portion and the second portion comprises at least one first sweetener.

In some embodiments, at least a portion of the at least one first sweetener is encapsulated while in other embodiments, at least a portion of the at least one first sweetener is unencapsulated. In other embodiments, the first portion includes a sweetener potentiator while in still other embodiments, the second portion includes a sweetener potentiator.

In some embodiments, there is provided an edible composition comprising:
 a cooked sugar component;
 a cooked saccharide component; and
 a gum base component.

In some embodiments, there is provided an edible composition comprising:
 a cooked sugar component;
 a cooked saccharide component; and
 a gum component.

In some embodiments, there is provided an edible composition comprising:
 a cooked sugar component;
 a cooked saccharide component; and
 an elastomeric component.

In some embodiments, there is provided a method of making an edible composition comprising:
 adding a chewing gum base to a mixer;
 adding a cooked saccharide syrup to the mixer after addition of the chewing gum base; and
 applying high shear mixing in the mixer to create a homogeneous composition of the chewing gum base and the cooked saccharide syrup.

In some embodiments, there is provided a method of making an edible composition comprising:
 determining the rheology of a chewing gum base;
 determining the rheology of a cooked saccharide syrup; and
 adjusting processing parameters of an extruder based on the chewing gum base rheology and the cooked saccharide syrup rheology such that a desired texture is achieved when the chewing gum base and the cooked saccharide syrup are mixed in the extruder.

In some embodiments, there is provided a method of making an edible composition comprising:
   determining the rheology of a chewing gum base;
   determining the rheology of a cooked saccharide syrup;
   determining amounts of the chewing gum base and the cooked saccharide syrup; and
   adjusting processing parameters of an extruder based on the amounts and rheologies of the chewing gum base and the cooked saccharide syrup such that a desired texture is achieved when the chewing gum base and the cooked saccharide syrup are mixed in said extruder.

In some embodiments there is provided a method of reducing the cost of goods for an edible composition comprising:
   mixing a chewing gum base and a cooked saccharide syrup in a high shear mixer to create a homogeneous composition;
   forming finished product pieces as the homogeneous composition exits said high shear mixer; and
   packaging the finished product pieces without subjecting the finished product pieces to conditioning involving holding the finished product pieces at constant temperature and relative humidity until they are rigid.

In some embodiments, a method of reducing the cost of goods for the edible composition further comprises:
   adjusting an amount of the chewing gum base and an amount of the cooked saccharide syrup to maximize the amount of the cheaper component; and
   maintaining a desired texture by adjusting processing parameters on the high shear mixer.

In some embodiments, there is provided a method of making an edible composition comprising:
   adding a chewing gum base to an extruder;
   adding a cooked saccharide syrup to the extruder; and
   applying high shear mixing in the extruder to create a homogeneous composition of the chewing gum base and the cooked saccharide syrup.

In some embodiments, there is provided a method of making an edible composition comprising:
   determining the rheology of a chewing gum base;
   determining the rheology of a cooked saccharide syrup; and
   adjusting processing parameters of an extruder based on the chewing gum base rheology and the cooked saccharide syrup rheology such that a desired texture is achieved when the chewing gum base and the cooked saccharide syrup are mixed in the extruder.

In some embodiments, there is provided a method of making an edible composition comprising:
   adding a chewing gum to an extruder;
   adding a cooked saccharide syrup to the extruder; and
   applying high shear mixing in the extruder to create a homogeneous composition of the chewing gum and the cooked saccharide syrup.

In some embodiments, there is provided a method of making an edible composition comprising:
   determining rheology of a chewing gum;
   determining rheology of a cooked saccharide syrup; and
   adjusting processing parameters of an extruder based on the chewing gum rheology and the cooked saccharide syrup rheology such that a desired texture is achieved when the chewing gum and the cooked saccharide syrup are mixed in the extruder.

In some embodiments, there is provided a method of making an edible composition comprising:
   adding an elastomeric material to an extruder;
   adding a cooked saccharide syrup to the extruder; and
   applying high shear mixing in the extruder to create a homogeneous composition.

In some embodiments, there is provided a method of making an edible composition comprising:
   determining rheology of an elastomeric material;
   determining rheology of a cooked saccharide syrup; and
   adjusting processing parameters of an extruder based on the elastomeric material rheology and the cooked saccharide syrup rheology such that a desired texture is achieved when the elastomeric material and the cooked saccharide syrup are mixed in the extruder.

In some embodiments, there is provided a method of making an edible composition comprising:
   adding an elastomeric material to a mixer;
   adding a cooked saccharide syrup to a mixer; and
   applying high shear mixing in the mixer to create a homogeneous composition of the elastomeric material and the cooked saccharide syrup.

In some embodiments, there is provided a method of making an edible composition comprising:
   determining rheology of an elastomeric material;
   determining rheology of a cooked saccharide syrup; and
   adjusting processing parameters of a mixer based on the elastomeric material rheology and the cooked saccharide syrup rheology such that a desired texture is achieved when the elastomeric material and the cooked saccharide syrup are mixed in the mixer.

Dualities and Multi-Modalities

As described above, in some embodiments, confectionery compositions comprising at least two components within the cooked saccharide portion and elastomeric portion can be optionally coated or center-filled and can be configured to create dualities and multi-modalities. In some embodiments, the at least two components may be opposed to each other, i.e., distinctly different components. For example, two opposed flavors, such as strawberry and kiwi, may be employed. In some embodiments, the at least two components may be complementary to one another. For example, two mint oils that complement each other, such as peppermint and spearmint, may be employed. In some embodiments, the at least two components may differ in intensity from one another. For example, a single mint oil may be used, but in different amounts or intensities such that an intensity difference exists between the two portions of the mint oil. In some embodiments, the release of the at least two components can be such that a lesser amount can produce a higher intensity. For example, mint oil included in a cooked saccharide portion at an amount lower than a mint oil amount included in an elastomeric portion can produce a higher intensity due to an increased release from the cooked saccharide portion.

The components that create the duality, or multi-modality, may be included in different portions of the confectionery composition. For example, in some embodiments, a first component may be present in the cooked saccharide portion and a second component, which is distinct from, complementary to or different in intensity from the first component, may be present in the elastomeric portion. Some embodiments may include a first component in the cooked saccharide portion and a second component, which is distinct from, complementary to or different in intensity from the first component, in a coating or center-fill. Some other embodiments may include a first component in the elastomeric portion and a second component, which is distinct from, complementary to or different in intensity from the first component, in the coating or center-fill.

A variety of other combinations of the first and second components also may be employed. In some embodiments, for example, a first component may be included in one portion of the coated or center-filled confectionery composition and a second component, which may be divided into two portions, may be included in the other two portions of the coated or center-filled confectionery composition confectionery. The second component may be distinct from, complementary to or different in intensity from the first component. For example, the first component may be included in the elastomeric portion. A first portion of the second component may be included in the cooked saccharide and a second portion of the second component may be included in the coating or center-fill of the coated or center-filled confectionery composition. The first and second portions of the second component may be the same or different in amount.

Non-limiting examples of some of the possible physical combinations for providing a duality in a confectionery composition are indicated in Table 1 below. In particular, Table 1 identifies a number of different physical combinations of components that may be employed involving dualities among: (1) distinct components; (2) complementary components; and (3) intensity differences between a single component.

As referred to in Table 1 and as defined above, the coating composition refers to the outermost portion of the confection, the center-fill composition refers to an innermost portion of the confection, the elastomeric portion composition refers to the water insoluble polymer ingredients and the cooked saccharide portion refers to the saccharide and other optional ingredients. As used in Table 1, A represents a first component and B represents a second component, which is distinct from the first component. A' represents a second component that is complementary to the first component. 1/n is used to indicate a fractional portion of component A. 1/m is used to indicate a fractional portion of component A that is different from fractional portion 1/n. n*A is used to indicate a multiplicative portion of component A, and m*A indicates a multiplicative portion of component A that is different from multiplicative portion n*A.

TABLE 1

| Coating or Center-fill Composition | Elastomeric Portion Composition | Cooked Saccharide Portion Composition |
|---|---|---|
| (1) Dualities based on differences between separate and distinct components: | | |
| A | B | |
| A | | B |
| | A | B |
| B | A | |
| B | | A |
| | B | A |
| 1/n A | B | 1/n A |
| 1/n A | 1/n A | B |
| B | 1/n A | 1/n A |
| 1/n A | B | 1/m A |
| 1/n A | 1/m A | B |
| B | 1/n A | 1/m A |
| (2) Dualities based on complementary components: | | |
| A | A' | |
| A | | A' |
| | A | A' |
| A' | A | |

TABLE 1-continued

| Coating or Center-fill Composition | Elastomeric Portion Composition | Cooked Saccharide Portion Composition |
|---|---|---|
| A' | | A |
| | A' | A |
| 1/n A | A' | 1/n A |
| 1/n A | 1/n A | A' |
| A' | 1/n A | 1/n A |
| 1/n A | A' | 1/m A |
| 1/n A | 1/m A | A' |
| A' | 1/n A | 1/m A |
| (3) Dualities based on intensity differences of a single component: | | |
| n*A | A | |
| n*A | | A |
| | n*A | A |
| A | n*A | |
| A | | n*A |
| | A | n*A |
| n*A | A | n*A |
| n*A | n*A | A |
| A | n*A | n*A |
| n*A | A | m*A |
| n*A | m*A | A |
| A | n*A | m*A |

Table 1, above, provides examples of a variety of different physical combinations of two components used to impart a duality to a confection. In some embodiments, more than one combination might be included.

Some embodiments provided herein may extend to combinations that include more than two components to create a duality, or multi-modality. In some embodiments, for example, three components may be employed, one component in each separate portion of the confectionery composition. For example, a first flavor may be present in the cooked saccharide portion, a second flavor in the elastomeric portion, and a third flavor in the optional coating or center-fill. The three flavors may be distinct from one another, complementary to one another or different in intensities from one another. In some embodiments, three components may be used to impart a duality, or multi-modality, with a first component in one portion of the confectionery composition and the second and third components together in another portion of the confectionery composition.

In embodiments containing three or more components, the components may provide multiple dualities. For example, in a three component embodiment, two of the components may be distinct from each other, whereas two of the components are complementary or different in intensity from each other. A confectionery composition may, for example, include peppermint flavor in the cooked saccharide portion and a different level or intensity of peppermint flavor in the coating or center-fill, thereby imparting a first duality, which is an intensity differential. Cinnamon may be included in the elastomeric portion, which is distinct from the peppermint flavors. A second duality based on the cinnamon-peppermint flavor distinction also is present in the confectionery composition. Accordingly, a multi-modality confectionery product may be provided having two different dualities.

A number of different combinations including two, three, four or even more components in any portion of the confectionery composition may be prepared providing additional dualities or combinations of dualities.

Alternatively, in some embodiments, the at least two components that create the duality, or multi-modality, may be present in the same portion of a confectionery composition. For example, two distinct flavors, such as strawberry and kiwi, both may be present in the cooked saccharide portion of the confectionery composition. Some embodiments may include multiple dualities, such as dual flavors and dual sensations, all in the same portion of the confectionery composition. In some other embodiments, a single duality may be present in one portion, and a second duality may be present in another portion of the confectionery composition.

As noted above, there are several different types of dualities that may be present in a confectionery composition. The components that create the dualities may be used in any of the physical combinations discussed above. In particular, dualities may exist among flavors, sensations, tastes and functionalities. Additionally, dualities among colors may exist. Combinations of these different dualities also may be employed.

Flavor Dualities

More specifically, some confectionery compositions may include a flavor duality. In some embodiments, one of the portions of the confectionery composition may include a first flavor and at least a second of the portions may include at least a second flavor. The second flavor may be distinct from, complementary to or different in intensity from the first flavor. For example, a cooked saccharide portion may include the first flavor and an elastomeric portion may include the second flavor. The cooked saccharide portion may include the first flavor and the coating or center-fill may include the second flavor. The elastomeric portion may include the first flavor and the coating or center-fill may include the second flavor.

In some embodiments, the cooked saccharide portion may include the first flavor, the elastomeric portion the second flavor and the coating or center-fill may include a third flavor. The coating or center-fill flavor may be the same as the elastomeric portion flavor. In such embodiments, the cooked saccharide portion flavor may be distinct from, complementary to or different in intensity from both the coating or center-fill and elastomeric portion flavors. In other embodiments, the coating or center-fill flavor may be complementary to the elastomeric portion flavor, but distinct from the cooked saccharide portion flavor. For example, the elastomeric portion and coating or center-fill flavors may be two different mint flavors, such as, peppermint and spearmint. The cooked saccharide portion flavor may be distinct from the mint flavors, such as, for example, cinnamon. Alternatively, the coating or center-fill flavor may be the same as the cooked saccharide portion flavor. In such embodiments, the elastomeric portion flavor may be distinct from, complementary to or different in intensity from both the coating or center-fill and cooked saccharide portion flavors. In other embodiments, the coating or center-fill flavor may be complementary to the cooked saccharide portion flavor, but distinct from the elastomeric portion flavor.

A variety of flavors may be used in any of these or other combinations to impart different dualities. More specifically, in some embodiments, at least two flavors that are distinct may be employed. Dualities based on distinct flavors may include, but are not limited to, the following combinations: a mint flavor and a fruit flavor; a mint flavor and a spicy flavor; a mint flavor and a savory flavor; a mint flavor and an indulgent flavor; a fruit flavor and a spicy flavor; a fruit flavor and a savory flavor; a fruit flavor and an indulgent flavor; a spicy flavor and a savory flavor; a spicy flavor and an indulgent flavor; and a savory flavor and an indulgent flavor.

Some of the duality combinations set forth above include an indulgent flavor. As used herein, "indulgent" refers to a type of flavor associated with a creamy or decadent taste. Sometimes these flavors are referred to as "sweet/brown" in the art. Examples of suitable indulgent flavors include, but are not limited to, maple, cola, chocolate, dulce de leche, raisin, vanilla, caramel, dairy flavors, such as cream, butter, milk and yoghurt, butterscotch, peanut butter, fruit cream flavors, such as strawberry cream, and combinations thereof.

In some embodiments, an indulgent flavor is included in a texture modifying agent as discussed below to provide an unctuous mouthfeel along with the indulgent flavor perception. In some embodiments, the indulgent flavor and unctuous mouthfeel provide an eating experience similar to high caloric confections such as chocolate without delivering the calories.

In some embodiments, at least two flavors that are complementary may be employed. In some embodiments, the complementary flavors may be the same type of flavor, e.g., two different mint flavors. In some other embodiments, a first flavor, e.g., a fruit flavor, may be provided, and the second flavor may be complementary by enhancing the first flavor, e.g., a fruit potentiator. More specifically, dualities based on complementary flavors may include, but are not limited to, the following combinations: a mint flavor and a mint potentiator; a fruit flavor and a fruit potentiator; a spicy flavor and a spice potentiator; a savory flavor and a savory potentiator; a mint flavor and a different mint flavor; a fruit flavor and a different fruit flavor; a spicy flavor and a different spicy flavor; a savory flavor and a different savory flavor; and an indulgent flavor and a different indulgent flavor.

In some embodiments, the duality may be based on at least two portions of a flavor that differ in intensity. For example, any of the following types of flavors may be used in at least two portions, each of which contains a different amount or intensity of the flavor: mint flavor; fruit flavor; spicy flavor; savory flavor; and indulgent flavor. For example, one of the portions of the confectionery composition may include a first amount or intensity of a flavor and a separate portion may include a second amount or intensity of the same flavor. The second amount or intensity may be greater than the first amount or intensity of the flavor, thereby creating an intensity differential in the flavor impact. It further may be desirable, in some embodiments, to include a third portion of the same flavor in the remaining portion of the confection, which is different in amount or intensity than the first and/or second portion.

In some embodiments, the amount of flavor used to create a desired intensity is determined by the portion to which the flavor is added. For example, the amount of flavor added to the cooked saccharide portion to create a desired intensity can be lower than the amount of flavor added to the elastomeric portion to create the same intensity. Therefore, in some embodiments, a desired confectionery composition flavor intensity can be created using an amount of flavor lower than would be needed to create the same flavor intensity in a confectionery composition without the cooked saccharide portion.

A variety of exemplary flavors, such as mint, fruit, spicy, savory and indulgent flavors are provided in Table 2 herein. Specific flavors may be selected from Table 2 and combined in various manners as described herein.

Further, in some embodiments, at least one of the flavors may have a modified release profile. As described in more detail below, components may be at least partially encapsulated to provide a modified release profile. Suitable encapsulating materials and methods of encapsulation are provided in more detail below in the section entitled "Additional Components." One or all of the flavors used in the confectionery composition may be at least partially encapsulated. Further, in some embodiments, at least one of the flavors may include a mixture of the flavor in its encapsulated and unencapsulated (sometimes referred to as "free") forms. Encapsulated and unencapsulated forms of a flavor may be included in any of the portions of the confectionery composition in the same or different amounts.

Some embodiments described herein extend to methods of preparing multi-modality confectionery products, which include at least one flavor duality. In particular, a confectionery composition including any of the flavor dualities described above may first be provided. The confectionery composition may include a cooked saccharide portion, an elastomeric portion and optionally a third portion, which may be a coating or shell or a center-fill. One of the confectionery composition portions may include at least one first flavor and at least a second portion of the confectionery composition portions may include at least one second flavor. The second flavor may be distinct from, complementary to or different in intensity from the first flavor. Individual confectionery composition pieces then may be formed from the confectionery composition. Methods of forming individual confectionery pieces from confectionery compositions are described in more detail below in the section entitled "Processing."

In some embodiments, methods of imparting a dual flavor perception are provided. In accordance therewith, a confectionery product prepared as described above may be provided. The chewing confectionery product may include a cooked saccharide portion, an elastomeric portion, and optionally a third portion, which may be a coating or a center-fill. One of the confectionery composition portions may include at least one first flavor and at least a second portion of the confectionery composition portions may include at least one second flavor. The second flavor may be distinct from, complementary to or different in intensity from the first flavor. The confectionery product may be applied into the oral cavity of an individual. As the individual chews the product and saliva mixes therewith, the at least one first flavor and the at least one second flavor may be released from the confection. The individual may experience a dual flavor perception as the first and second flavors are released and combine in the oral cavity.

Additional embodiments described herein relate to methods of developing confectionery products, which provide a consumer-preferred duality, particularly a flavor duality. In accordance therewith, a consumer preference for a dual flavor combination may first be identified. The dual flavor combination may include at least one first flavor and at least one second flavor, which is distinct from, complementary to or different intensity from the first flavor. A variety of methods may be used to identity a consumer preference for a specific flavor duality, such as, market research, including consumer surveys, taste panels, and the like. Once a consumer preference for a dual flavor combination, such as, for example, kiwi and banana, is identified, a confectionery product tailored to satisfy that preference may be provided. In particular, any of the confectionery products described above may be prepared. The first flavor of the consumer-preferred duality may be added to one portion of the confectionery composition and the second flavor of the consumer-preferred duality may be added to another portion of the confectionery composition. The confectionery may be marketed to consumers based on the consumer-preferred duality and may be included in a kit including the confectionery product, a housing for the confectionery product, and instructions including a message communicating the consumer-preferred duality.

The consumer-preferred duality provided by the confectionery product may be marketed to consumers in a variety of manners. Suitable marketing strategies, include, for example, print, radio, satellite radio, television, movie theater and online advertising campaigns, point-of-purchase advertisements, billboard advertisements, public transportation and telephone booth advertisements, indicia on the product packaging, including slogans, trademarks, terms and colors, instant messaging, ringtones, and the like.

Sensate Dualities

Some confectionery compositions may include a duality based on sensations, such as coolness, warmth and tingling sensations. Such sensations may be provided by sensates, such as cooling agents, warming agents and tingling agents, respectively. In some embodiments, one of the portions of the confectionery composition may include a first sensate and at least a second of the portions may include at least a second sensate. The second sensate may be distinct from, complementary to or different in intensity from the first sensate. For example, the cooked saccharide portion may include the first sensate and the elastomeric portion may include the second sensate. The cooked saccharide portion may include the first sensate and the optional coating or center-fill may include the second sensate. The elastomeric portion may include the first sensate and the coating or center-fill may include the second sensate.

In some embodiments, the cooked saccharide portion may include the first sensate, the elastomeric portion the second sensate and the coating or center-fill may include a third sensate. The coating or center-fill sensate may be the same as the elastomeric portion sensate. In such embodiments, the cooked saccharide portion sensate may be distinct from, complementary to or different in intensity from both the coating or center-fill and elastomeric portion sensates. In other embodiments, the coating or center-fill sensate may be complementary to the elastomeric portion sensate, but distinct from the cooked saccharide portion sensate. For example, the elastomeric portion and coating or center-fill sensates may be two different cooling agents, such as, menthol and menthyl succinate. The cooked saccharide portion sensate may be distinct from the cooling agents, such as, for example, a tingling agent. Alternatively, the coating or center-fill sensate may be the same as the cooked saccharide portion sensate. In such embodiments, the elastomeric portion sensate may be distinct from, complementary to or different in intensity from both the coating or center-fill and cooked saccharide portion sensates. In other embodiments, the coating or center-fill sensate may be complementary to the cooked saccharide portion sensate, but distinct from the elastomeric portion sensate.

A variety of sensates may be used in any of these or other combinations to impart different dualities. More specifically, in some embodiments, at least two sensates that are distinct may be employed. Dualities based on distinct sensates may include, but are not limited to, the following combinations: a cooling agent and a warming agent; a cooling agent and a tingling agent; and a warming agent and a tingling agent.

In some embodiments, at least two sensates that are complementary may be employed. In particular, the complementary sensates may be the same type of sensate, such as, two different cooling agents, two different warming agents or two different tingling agents.

In some embodiments, the duality may be based on at least two portions of a sensate that differ in intensity. Any of the following types of sensates may be used in at least two portions, each of which contains a different amount or delivers a different intensity of the sensate: cooling agents, warming agents or tingling agents. For example, one of the portions of the confectionery composition may include a first amount or intensity of a sensate and a separate portion may include a second amount or intensity of the same sensate. The second amount or intensity may be greater than the first amount or intensity of the sensate, thereby creating an intensity differential in the sensation. It further may be desirable, in some embodiments, to include a third portion or intensity of the same sensate in the remaining portion of the confectionery composition, which is different in amount or intensity than the first and/or second portion or intensity of the sensate.

As with the flavor ingredients described above, the amounts of sensates added to the various portions of a confectionery composition can depend on the composition of that portion and how the sensate interacts with that portion. For example, in some embodiments, sensates with an affinity for the polymers in elastomeric are used in lower amounts to deliver a desired sensation intensity when they are included in portions such as the cooked saccharide, coating, or center-fill portions than when those sensates with an affinity for elastomeric materials are included in the elastomeric portion. Therefore, in some embodiments, the overall level of sensates needed to deliver a desired sensation can be manipulated and lowered by including the sensate in one portion versus another.

A variety of exemplary sensates, such as cooling, warming and tingling agents are provided in Table 2 herein. Specific sensates may be selected from Table 2 and combined in various manners as described herein.

Further, in some embodiments, at least one of the sensates may have a modified release profile. As described in more detail below, components may be at least partially encapsulated to provide a modified release profile. Suitable encapsulating materials and methods of encapsulation are provided in more detail below in the section entitled "Additional Components." One or all of the sensates used in the confectionery composition may be at least partially encapsulated. Further, in some embodiments, at least one of the sensates may include a mixture of the sensate in its encapsulated and unencapsulated (sometimes referred to as "free") forms. Encapsulated and unencapsulated forms of a sensate may be included in any of the portions of the confectionery compositions in the same or different amounts.

Some embodiments described herein extend to methods of preparing multi-modality confectionery products, which include at least one sensation duality. In particular, a confectionery composition including any of the sensation dualities described above may first be provided. The confectionery composition may include a cooked saccharide portion, an elastomeric portion and optionally a third portion, which may be a coating or center-fill. One of the confectionery composition portions may include at least one first sensate and at least a second of the confectionery composition portions may include at least one second sensate. The second sensate may be distinct from, complementary to or different in intensity from the first sensate. Individual confectionery composition pieces then may be formed from the confectionery composition. Methods of forming individual confectionery pieces from confectionery compositions are described in more detail below in the section entitled "Processing."

In some embodiments, methods of imparting a dual sensation perception are provided. In accordance therewith, a confectionery product prepared as described above may be provided. The confectionery product may include a cooked saccharide portion, an elastomeric portion, and optionally a third portion, which may be a coating or center-fill. One of the confectionery composition portions may include at least one first sensate and at least a second of the confectionery composition portions may include at least one second sensate. The second sensate may be distinct from, complementary to or different in intensity from the first sensate. The confectionery product may be applied into the oral cavity of an individual. As the individual chews the product and saliva mixes therewith, the at least one first sensate and the at least one second sensate may be released from the confection. The individual may experience a dual sensation perception as the first and second sensates are released and combine in the oral cavity.

Additional embodiments described herein relate to methods of developing confectionery products, which provide a consumer-preferred duality, particularly a sensation duality. In accordance therewith, a consumer preference for a dual sensation combination may first be identified. The dual sensation combination may include at least one first sensate and at least one second sensate, which is distinct from, complementary to or different in intensity from the first sensate. A variety of methods may be used to identify a consumer preference for a specific sensation duality, such as, market research, including consumer surveys, taste panels, and the like. Once a consumer preference for a dual sensation combination, such as, for example, cooling and tingling, is identified, a confectionery product tailored to satisfy that preference may be provided. In particular, any of the confectionery products described above may be prepared. The first sensate of the consumer-preferred duality may be added to one portion of the confectionery composition and the second sensate of the consumer-preferred duality may be added to another portion of the confectionery composition. The confectionery product may be marketed to consumers based on the consumer-preferred duality.

The consumer-preferred duality provided by the confectionery product may be marketed to consumers in a variety of manners. Suitable marketing strategies, include, for example, print, radio, satellite radio, television, movie theater and online advertising campaigns, point-of-purchase advertisements, billboard advertisements, public transportation and telephone booth advertisements, indicia on the product packaging, including slogans, trademarks, terms and colors, instant messaging, ringtones, and the like.

Taste Dualities

Some confectionery compositions may include a duality based on tastes, such as, bitter, salty, sweet, sour, umami and kokumi tastes. Tastants are agents that may provide such tastes. In some embodiments, one of the portions of the confectionery composition may include a first tastant and at least a second of the portions may include at least a second tastant. The second tastant may be distinct from, complementary to or different in intensity from the first tastant. For example, the cooked saccharide portion may include the first tastant and the elastomeric portion may include the second tastant. The cooked saccharide portion may include the first tastant and the optional coating or center-fill may include the second tastant. The elastomeric portion may include the first tastant and the coating or center-fill may include the second tastant.

In some embodiments, the cooked saccharide portion may include the first tastant, the elastomeric portion the second tastant and the coating or center-fill may include a third tastant. The coating or center-fill tastant may be the same as the elastomeric portion tastant. In such embodiments, the cooked saccharide tastant may be distinct from, complementary to or different in intensity from both the coating or center-fill and elastomeric portion tastants. In other embodiments, the coating or center-fill tastant may be complementary to the elastomeric portion tastant, but distinct from the cooked saccharide tastant. For example, the elastomeric portion and coating or center-fill tastant may be two different sweeteners, such as, sucralose and sorbitol. The cooked saccharide tastant may be distinct from the sweeteners, such as, for example, a citric acid, which is a sour agent. Alternatively, the coating or center-fill tastant may be the same as the cooked saccharide portion tastant. In such embodiments, the elastomeric portion tastant may be distinct from, complementary to or different in intensity from both the coating or center-fill and cooked saccharide tastants. In other embodiments, the coating or center-fill tastant may be complementary to the cooked saccharide tastant, but distinct from the elastomeric portion tastant.

A variety of tastants may be used in any of these or other combinations to impart different dualities. More specifically, in some embodiments, at least two tastants that are distinct may be employed. Dualities based on distinct tastes may include, but are not limited to, the following combinations: a sweet tastant and a sour tastant; a sweet tastant and a salty tastant; a sweet tastant and a bitter tastant; a sweet tastant and an astringent tastant; a sweet tastant and an umami tastant; a sweet tastant and a kokumi tastant; a sour tastant and a salty tastant; a sour tastant and a bitter tastant; a sour tastant and an astringent tastant; a sour tastant and an umami tastant; a sour tastant and a kokumi tastant; a salty tastant and a bitter tastant; a salty tastant and an astringent tastant; a salty tastant and an umami tastant; a salty tastant and a kokumi tastant; a bitter tastant and an astringent tastant; a bitter tastant and an umami tastant; and a bitter tastant and a kokumi tastant.

In some embodiments, at least two tastants that are complementary may be employed. In particular, the complementary tastants may be the same type of tastant, such as, two different bitter agents; two different sour agents, two different sweeteners; two different salts; two different umami agents; or two different kokumi agents.

In some embodiments, the duality may be based on at least two portions of a tastant that differ in intensity. Any of the following types of tastants may be used in at least two portions, each of which contains a different amount or provides a different intensity of the tastant: bitter agents; two different sour agents, two different sweeteners; two different salts; two different umami agents; or two different kokumi agents. For example, one of the portions of the confectionery composition may include a first amount of a tastant and a separate portion may include a second amount of the same tastant. The second amount may be greater than the first amount of the tastant, thereby creating an intensity differential in the taste. Alternatively, the tastant may provide a greater intensity at a lower amount due to the tastant's interaction with the portion. It further may be desirable, in some embodiments, to include a third portion of the same tastant in the remaining portion of the chewing confectionery, which is different in amount or intensity than the first and/or second portion of the tastant.

Some of the duality combinations set forth above include an umami tastant. "Umami" refers to a taste that is savory, or the taste of glutamate.

Some of the duality combinations set forth above include a kokumi tastant. "Kokumi" refers to materials that impart "mouthfulness" and "good body," as disclosed in U.S. Pat. No. 5,679,397 to Kuroda et al., which is incorporated in its entirety herein by reference.

A variety of exemplary tastants, such as bitter, salty, sweet, sour, umami and kokumi tastants are provided in Table 2 herein. Specific tastants may be selected from Table 2 and combined in various manners as described herein.

Further, in some embodiments, at least one of the tastants may have a modified release profile. As described in more detail below, components may be at least partially encapsulated to provide a modified release profile. Suitable encapsulating materials and methods of encapsulation are provided in more detail below in the section entitled "Additional Components." One or all of the tastants used in the confectionery compositions may be at least partially encapsulated. Further, in some embodiments, at least one of the tastants may include a mixture of the tastant in its encapsulated and unencapsulated (sometimes referred to as "free") forms. Encapsulated and unencapsulated forms of a tastant may be included in any of the portions of the confectionery compositions in the same or different amounts or in amounts that deliver the same or different intensities.

Some embodiments described herein extend to methods of preparing multi-modality confectionery products, which include at least one taste duality. In particular, a confectionery composition including any of the taste dualities described above may first be provided. The confectionery composition may include a cooked saccharide portion, an elastomeric portion, and optionally a third portion, which may be a coating or center-fill. One of the confectionery composition portions may include at least one first tastant and at least a second of the confectionery composition portions may include at least one second tastant. The second tastant may be distinct from, complementary to or different in intensity from the first tastant. Individual confectionery composition pieces then may be formed from the confectionery composition. Methods of forming individual confectionery pieces from chewing confectionery compositions are described in more detail below in the section entitled "Processing."

In some embodiments, methods of imparting a dual taste perception are provided. In accordance therewith, a confectionery product prepared as described above may be provided. The confectionery product may include a cooked saccharide portion, an elastomeric portion, and optionally a third portion, which may be a coating or center-fill. One of the confectionery composition portions may include at least one first tastant and at least a second of the confectionery composition confectionery portions may include at least one second tastant. The second tastant may be distinct from, complementary to or different in intensity from the first tastant. The confectionery product may be applied into the oral cavity of an individual. As the individual chews the product and saliva mixes therewith, the at least one first tastant and the at least one second tastant may be released from the confectionery composition. The individual may experience a dual taste perception as the first and second tastants are released and combine in the oral cavity.

Additional embodiments described herein relate to methods of developing confectionery products, which provide a consumer-preferred duality, particularly a taste duality. In accordance therewith, a consumer preference for a dual taste combination may first be identified. The dual taste combination may include at least one first tastant and at least one second tastant, which is distinct from, complementary to or different intensity from the first tastant. A variety of methods may be used to identify a consumer preference for a specific taste duality, such as, market research, including consumer surveys, taste panels, and the like. Once a consumer preference for a dual taste combination, such as, for example, bitter and astringent, is identified, a confectionery product tailored to satisfy that preference may be provided. In particular, any of the confectionery products described above may be prepared. The first tastant of the consumer-preferred duality may be added to one portion of the confectionery composition and the second tastant of the consumer-preferred duality may be added to another portion of the confectionery composition. The confectionery product may be marketed to consumers based on the consumer-preferred duality.

The consumer-preferred duality provided by the confectionery product may be marketed to consumers in a variety of manners. Suitable marketing strategies, include, for example, print, radio, satellite radio, television, movie theater and online advertising campaigns, point-of-purchase advertisements, billboard advertisements, public transportation and telephone booth advertisements, indicia on the product packaging, including slogans, trademarks, terms and colors, instant messaging, ringtones, and the like.

Functional Dualities

Some confectionery compositions may include a duality based on functionalities. Functionalities include, for example, teeth whitening and breath freshening, among others, and may be provided by various functional agents. In some embodiments, one of the portions of the confectionery composition may include a first functional agent and at least a second of the portions may include at least a second functional agent. The second functional agent may be distinct from, complementary to or different in intensity from the first functional agent. For example, the cooked saccharide portion may include the first functional agent and the elastomeric portion may include the second functional agent. The cooked saccharide portion may include the first functional agent and the coating or center-fill may include the second functional agent. The elastomeric portion may include the first functional agent and the coating or center-fill may include the second functional agent.

In some embodiments, the cooked saccharide portion may include the first functional agent, the elastomeric portion the second functional agent and the coating or center-fill may include a third functional agent. The coating or center-fill functional agent, in some embodiments, may be the same as the elastomeric portion functional agent. In such embodiments, the cooked saccharide portion functional agent may be distinct from, complementary to or different in intensity from both the coating or center-fill and elastomeric portion functional agents. In other embodiments, the coating or center-fill functional agent may be complementary to the elastomeric portion functional agent, but distinct from the cooked saccharide portion functional agent. For example, the elastomeric portion and coating or center-fill functional agents may be two different anti-plaque agents, such as, chlorhexidine and triclosan. The cooked saccharide portion functional agent may be distinct from the anti-plaque agents, such as, for example, a remineralization agent. Alternatively, the coating or center-fill functional agent may be the same as the cooked saccharide portion functional agent. In such embodiments, the elastomeric portion functional agent may be distinct from, complementary to or different in intensity from both the coating or center-fill and cooked saccharide portion functional agents. In other embodiments, the coating or center-fill functional agent may be complementary to the cooked saccharide portion functional agent, but distinct from the elastomeric portion functional agent.

A variety of functional agents may be used in any of these or other combinations to impart different dualities. More specifically, in some embodiments, at least two functional agents that are distinct may be employed. Dualities based on distinct functional agents may include, but are not limited to, the following combinations: a vitamin and a mineral; a breath freshening agent and a tooth whitening agent; a breath freshening agent and a remineralization agent; a breath freshening agent and an antimicrobial agent; a tooth whitening agent and a stain prevention agent; a remineralization agent and a demineralization agent; an appetite suppressant and a stress relieving agent; an energy boosting agent and a stress relieving agent; and a concentration enhancing agent and a focus enhancing agent.

In some embodiments, at least two functional agents that are complementary may be employed. In particular, the complementary functional agents may be the same type of functional agent, such as, two different surfactants, two different breath freshening agents, two different anti-microbial agents, two different antibacterial agents, two different anti-calculus agents, two different anti-plaque agents, two different fluoride compounds, two different quaternary ammonium compounds, two different remineralization agents, two different demineralization agents, two different pharmaceutical actives, two different micronutrients, two different throat care actives, two different tooth whitening agents, two different stain removing agents, two different energy boosting agents, two different concentration boosting agents, two different focus enhancing agents and two different appetite suppressants.

In some embodiments, the duality may be based on at least two portions of a functional agent that differ in intensity. Any of the types of functional agents set forth above in the description of complementary functional agents may be used in at least two portions, each of which contains a different amount of the functional agent. For example, one of the portions of the confectionery composition may include a first amount of a functional agent and a separate portion may include a second amount of the same functional agent. The second amount may be greater than the first amount of the functional agent, thereby creating an intensity differential in the functionality. Additionally, the difference in intensity may arise from the composition of the portion and interaction between the portion and the functional agent. Therefore, in some embodiments, lower amounts can provide higher intensities of functional agents when they are more completely released from a given portion. It further may be desirable, in some embodiments, to include a third portion of the same functional agent in the remaining portion of the confectionery composition, which is different in amount or intensity than the first and/or second portion of the functional agent.

A variety of exemplary functional agents are provided in Table 2 herein. Specific functional agents may be selected from Table 2 and combined in various manners as described herein.

Further, in some embodiments, at least one of the functional agents may have a modified release profile. As described in more detail below, components may be at least partially encapsulated to provide a modified release profile.

Suitable encapsulating materials and methods of encapsulation are provided in more detail below in the section entitled "Additional Components." One or all of the functional agents used in the confectionery compositions may be at least partially encapsulated. Further, in some embodiments, at least one of the functional agents may include a mixture of the functional agent in its encapsulated and unencapsulated (sometimes referred to as "free") forms. Encapsulated and unencapsulated forms of a functional agent may be included in any of the portions of the confectionery composition in the same or different amounts or intensities.

Some embodiments described herein extend to methods of preparing multi-modality confectionery products, which include at least one functional duality. In particular, a confectionery composition including any of the functional dualities described above may first be provided. The confectionery composition may include a cooked saccharide portion, an elastomeric portion, and optionally a third portion, which may be a coating or center-fill. One of the confectionery composition portions may include at least one first functional agent and at least a second of the confectionery composition portions may include at least one second functional agent. The second functional agent may be distinct from, complementary to or different in intensity from the first functional agent. Individual confectionery composition pieces then may be formed from the confectionery composition. Methods of forming individual confectionery pieces from confectionery compositions are described in more detail below in the section entitled "Processing."

In some embodiments, methods of imparting a dual functional perception are provided. In accordance therewith, a confectionery product prepared as described above may be provided. The confectionery product may include a cooked saccharide portion, an elastomeric portion, and optionally a third portion, which may be a coating or center-fill. One of the confectionery composition portions may include at least one first functional agent and at least a second of the confectionery composition portions may include at least one second functional agent. The second functional agent may be distinct from, complementary to or different in intensity from the first functional agent. The confectionery product may be applied into the oral cavity of an individual. As the individual chews the product and saliva mixes therewith, the at least one first functional agent and the at least one second functional agent may be released from the confection. The individual may experience a dual functional perception as the first and second functional agents are released and combine in the oral cavity.

Additional embodiments described herein relate to methods of developing confectionery products, which provide a consumer-preferred duality, particularly a functional duality. In accordance therewith, a consumer preference for a dual functional combination may first be identified. The dual functional combination may include at least one first functional agent and at least one second functional agent, which is distinct from, complementary to or different intensity from the first functional agent. A variety of methods may be used to identify a consumer preference for a specific functional duality, such as, market research, including consumer surveys, taste panels, and the like. Once a consumer preference for a dual functional combination, such as, for example, breath freshening and stain removing, is identified, a confectionery product tailored to satisfy that preference may be provided. In particular, any of the confectionery products described above may be prepared. The first functional agent of the consumer-preferred duality may be added to one portion of the confectionery composition and the second functional agent of the consumer-preferred duality may be added to another portion of the confectionery composition. The chewing confectionery product may be marketed to consumers based on the consumer-preferred duality.

The consumer-preferred duality provided by the confectionery product may be marketed to consumers in a variety of manners. Suitable marketing strategies, include, for example, print, radio, satellite radio, television, movie theater and online advertising campaigns, point-of-purchase advertisements, billboard advertisements, public transportation and telephone booth advertisements, indicia on the product packaging, including slogans, trademarks, terms and colors, instant messaging, ringtones, and the like.

As mentioned above, specific flavors, sensates, tastants and functional agents may be selected from the exemplary listing of multi-modality components provided in Table 2 below and combined to create any of the different dualities described above. In particular, Table 2 is divided into the three separate portions of a confectionery composition, i.e., coating or center-fill, cooked saccharide portion, and an elastomeric portion. Suitable amounts for a multi-modality component when it is selected for use in any of the three portions are set forth in Table 2. Table 2 also provides a listing of basic components typically included in each of the three portions of a confectionery composition. Suitable amounts for the basic components also are set forth in Table 2. The amounts provided for the basic and multi-modality components are based on the specified portion in which the component is contained.

Further, the amounts provided for the multi-modality components in Table 2 generally apply to a component as it may be added to the specified portion of the confectionery composition in a free form, i.e., unencapsulated. In some embodiments, where the selected multi-modality component is provided in an encapsulated form, an amount greater than those amounts as set forth in Table 2 may be used due to the modified release profile of the component. Also, because a multi-modality component is selected in a specific embodiment to create a specific duality, the amounts provided in Table 2 represent amounts used only when the component is selected for inclusion in the composition. In other words, the lower limit of 0% is not included even though the multi-modality component may not be present.

Any of the multi-modality components listed in Table 2, below, which are selected to create a specific duality or multi-modality in a confectionery composition may be added to any portion of the confectionery composition in their encapsulated and/or unencapsulated forms.

As described above, Table 2 provides a list of multi-modality components that optionally may be present in one or more portions of the confectionery product. Suitable amounts that may be present in the coating or center-fill, cooked saccharide or elastomeric portion are provided in the table. The amounts in Table 2 are provided as ppm or weight % in a portion of the confectionery product. Table 2 is only representative and is not to be construed to limit the ingredients that can be included in the confectionery composition portions in any way.

TABLE 2

| Components | Optional Coating or Center-fill | Cooked Saccharide Portion | Elastomeric Portion |
|---|---|---|---|
| Basic Components | | | |
| Sugar | 0-100% | 0-95% | 20-80% |
| Polyol | 0-100% | 0-95% | 20-80% |
| Glycerin | 0-90% | 1-70% | 0-7% |
| Natural or synthetic confectionery | | 0-1% | |
| Elastomer | | | 10-70% |
| Bulking agent/Filler | 0-20% | 0-12% | 0-30% |
| Plasticizer/Softening agent | | | 0-10% |
| Mineral adjuvants | 0-20% | 0-20% | 0-12% |
| Wax | | | 0-3.0% |
| Emulsifier/Thickener | 0-3% | 0-5% | 0-1% |
| Texture Modifying Component | 0-10% | 2-25% | 0-30% |
| Multi-Modality Components | | | |
| I. Sensates | | | |
| A. Cooling agents | | | |
| Menthol | 10-500 ppm | 10-500 ppm | 500-20,000 ppm |
| Xylitol | 5-100% | 5-95% | 5-80% |
| Erythritol | 5-100% | 5-95% | 5-80% |
| Menthane | 10-500 ppm | 10-500 ppm | 500-20,000 ppm |
| Menthone | 10-500 ppm | 10-500 ppm | 500-20,000 ppm |
| Menthyl acetate | 10-500 ppm | 10-500 ppm | 500-20,000 ppm |
| Menthyl salicylate | 10-500 ppm | 10-500 ppm | 500-20,000 ppm |
| WS-23 | 10-500 ppm | 10-500 ppm | 500-20,000 ppm |
| WS-3 | 10-500 ppm | 10-500 ppm | 500-20,000 ppm |
| Menthyl succinate (and its alkaline earth metal salts) | 10-500 ppm | 10-500 ppm | 500-20,000 ppm |
| 3,1-menthoxypropane 1,2-diol | 10-500 ppm | 10-500 ppm | 500-20,000 ppm |
| Glutarate esters | 10-500 ppm | 10-500 ppm | 500-20,000 ppm |
| dextrose | 10-500 ppm | 10-500 ppm | 500-20,000 ppm |
| sorbitol | 10-500 ppm | 10-500 ppm | 500-20,000 ppm |
| ketals | 10-500 ppm | 10-500 ppm | 500-20,000 ppm |
| menthone ketals | 10-500 ppm | 10-500 ppm | 500-20,000 ppm |
| menthone glycerol ketals | 10-500 ppm | 10-500 ppm | 500-20,000 ppm |
| substituted p-menthanes | 10-500 ppm | 10-500 ppm | 500-20,000 ppm |
| acyclic carboxamides | 10-500 ppm | 10-500 ppm | 500-20,000 ppm |
| mono menthyl glutarate | 10-500 ppm | 10-500 ppm | 500-20,000 ppm |
| substituted cyclohexanamides | 10-500 ppm | 10-500 ppm | 500-20,000 ppm |
| substituted cyclohexane carboxamides | 10-500 ppm | 10-500 ppm | 500-20,000 ppm |
| substituted ureas and sulfonamides | 10-500 ppm | 10-500 ppm | 500-20,000 ppm |
| substituted menthanols | 10-500 ppm | 10-500 ppm | 500-20,000 ppm |
| hydroxymethyl | 10-500 ppm | 10-500 ppm | 500-20,000 ppm |
| hydroxymethyl derivatives of p-menthane | 10-500 ppm | 10-500 ppm | 500-20,000 ppm |
| 2-mercapto-cyclo-decanone | 10-500 ppm | 10-500 ppm | 500-20,000 ppm |
| hydroxycarboxylic acids with 2-6 carbon atoms | 10-500 ppm | 10-500 ppm | 500-20,000 ppm |
| cyclohexanamides | 10-500 ppm | 10-500 ppm | 500-20,000 ppm |
| l-isopulegol | 10-500 ppm | 10-500 ppm | 500-20,000 ppm |
| 3-(l-menthoxy)-2-methylpropane-1,2-diol | 10-500 ppm | 10-500 ppm | 500-20,000 ppm |
| p-menthane-2,3-diol | 10-500 ppm | 10-500 ppm | 500-20,000 ppm |
| p-menthane-3,8-diol | 10-500 ppm | 10-500 ppm | 500-20,000 ppm |
| 6-isopropyl-9-methyl-1,4-dioxaspiro[4,5]decane-2-methanol | 10-500 ppm | 10-500 ppm | 500-20,000 ppm |
| trimethylcyclohexanol | 10-500 ppm | 10-500 ppm | 500-20,000 ppm |
| N-ethyl-2-isopropyl-5-methylcyclohexanecarboxamide | 10-500 ppm | 10-500 ppm | 500-20,000 ppm |
| Japanese mint oil | 10-500 ppm | 10-500 ppm | 500-20,000 ppm |
| peppermint oil | 10-500 ppm | 10-500 ppm | 500-20,000 ppm |
| 3-(l-menthoxy)ethan-1-ol | 10-500 ppm | 10-500 ppm | 500-20,000 ppm |
| 3-(l-menthoxy)propan-1-ol | 10-500 ppm | 10-500 ppm | 500-20,000 ppm |
| 3-(l-menthoxy)butan-1-ol | 10-500 ppm | 10-500 ppm | 500-20,000 ppm |
| l-menthylacetic acid N-ethylamide | 10-500 ppm | 10-500 ppm | 500-20,000 ppm |
| l-menthyl-4-hydroxypentanoate | 10-500 ppm | 10-500 ppm | 500-20,000 ppm |
| l-menthyl-3-hydroxybutyrate | 10-500 ppm | 10-500 ppm | 500-20,000 ppm |
| N,2,3-trimethyl-2-(1-methylethyl)-butanamide | 10-500 ppm | 10-500 ppm | 500-20,000 ppm |
| n-ethyl-t-2-c-6 nonadienamide | 10-500 ppm | 10-500 ppm | 500-20,000 ppm |
| N,N-dimethyl menthyl succinamide | 10-500 ppm | 10-500 ppm | 500-20,000 ppm |
| substituted p-menthane-carboxamides | 10-500 ppm | 10-500 ppm | 500-20,000 ppm |
| 2-isopropanyl-5-methylcyclohexanol | 10-500 ppm | 10-500 ppm | 500-20,000 ppm |

TABLE 2-continued

| Components | Optional Coating or Center-fill | Cooked Saccharide Portion | Elastomeric Portion |
|---|---|---|---|
| menthyl lactate | 10-500 ppm | 10-500 ppm | 500-20,000 ppm |
| WS-30 | 10-500 ppm | 10-500 ppm | 500-20,000 ppm |
| WS-14 | 10-500 ppm | 10-500 ppm | 500-20,000 ppm |
| *Eucalyptus* extract | 10-500 ppm | 10-500 ppm | 500-20,000 ppm |
| Menthol PG carbonate | 10-500 ppm | 10-500 ppm | 500-20,000 ppm |
| Menthol EG carbonate | 10-500 ppm | 10-500 ppm | 500-20,000 ppm |
| Menthol glyceryl ether | 10-500 ppm | 10-500 ppm | 500-20,000 ppm |
| N-tertbutyl-p-menthane-3-carboxamide | 10-500 ppm | 10-500 ppm | 500-20,000 ppm |
| P-menthane-3-carboxylic acid glycerol ester | 10-500 ppm | 10-500 ppm | 500-20,000 ppm |
| Methyl-2-isopryl-bicyclo (2.2.1) Heptane-2-carboxamide | 10-500 ppm | 10-500 ppm | 500-20,000 ppm |
| Menthol methyl ether | 10-500 ppm | 10-500 ppm | 500-20,000 ppm |
| Methyl glutarate | 10-500 ppm | 10-500 ppm | 500-20,000 ppm |
| menthyl pyrrolidone carboxylate | 10-500 ppm | 10-500 ppm | 500-20,000 ppm |
| WS-5 | 10-500 ppm | 10-500 ppm | 500-20,000 ppm |
| WS-15 | 10-500 ppm | 10-500 ppm | 500-20,000 ppm |
| B. Warming agents | | | |
| vanillyl alcohol n-butylether | 1-1000 ppm | 1-1500 ppm | 10-8000 ppm |
| vanillyl alcohol n-propylether | 1-1000 ppm | 1-1500 ppm | 10-8000 ppm |
| vanillyl alcohol isopropylether | 1-1000 ppm | 1-1500 ppm | 10-8000 ppm |
| vanillyl alcohol isobutylether | 1-1000 ppm | 1-1500 ppm | 10-8000 ppm |
| vanillyl alcohol n-aminoether | 1-1000 ppm | 1-1500 ppm | 10-8000 ppm |
| vanillyl alcohol isoamylether | 1-1000 ppm | 1-1500 ppm | 10-8000 ppm |
| vanillyl alcohol n-hexylether | 1-1000 ppm | 1-1500 ppm | 10-8000 ppm |
| vanillyl alcohol methylether | 1-1000 ppm | 1-1500 ppm | 10-8000 ppm |
| vanillyl alcohol ethylether | 1-1000 ppm | 1-1500 ppm | 10-8000 ppm |
| gingerol | 1-1000 ppm | 1-1500 ppm | 10-8000 ppm |
| shogaol | 1-1000 ppm | 1-1500 ppm | 10-8000 ppm |
| paradol | 1-1000 ppm | 1-1500 ppm | 10-8000 ppm |
| zingerone | 1-1000 ppm | 1-1500 ppm | 10-8000 ppm |
| capsaicin | 1-1000 ppm | 1-1500 ppm | 10-8000 ppm |
| dihydrocapsaicin | 1-1000 ppm | 1-1500 ppm | 10-8000 ppm |
| nordihydrocapsaicin | 1-1000 ppm | 1-1500 ppm | 10-8000 ppm |
| homocapsaicin | 1-1000 ppm | 1-1500 ppm | 10-8000 ppm |
| homodihydrocapsaicin | 1-1000 ppm | 1-1500 ppm | 10-8000 ppm |
| ethanol | 1-1000 ppm | 1-1500 ppm | 10-8000 ppm |
| isopropyl alcohol | 1-1000 ppm | 1-1500 ppm | 10-8000 ppm |
| iso-amylalcohol | 1-1000 ppm | 1-1500 ppm | 10-8000 ppm |
| benzyl alcohol | 1-1000 ppm | 1-1500 ppm | 10-8000 ppm |
| glycerine | 1-1000 ppm | 1-1500 ppm | 10-8000 ppm |
| chloroform | 1-1000 ppm | 1-1500 ppm | 10-8000 ppm |
| eugenol | 1-1000 ppm | 1-1500 ppm | 10-8000 ppm |
| cinnamon oil | 1-1000 ppm | 1-1500 ppm | 10-8000 ppm |
| cinnamic aldehyde | 1-1000 ppm | 1-1500 ppm | 10-8000 ppm |
| C. Tingling agents | | | |
| Jambu Oleoresin or para cress | 5-500 ppm | 5-500 ppm | 50-5000 ppm |
| Japanese pepper extract | 5-500 ppm | 5-500 ppm | 50-5000 ppm |
| black pepper extract | 5-500 ppm | 5-500 ppm | 50-5000 ppm |
| *Echinacea* extract | 5-500 ppm | 5-500 ppm | 50-5000 ppm |
| Northern Prickly Ash extract | 5-500 ppm | 5-500 ppm | 50-5000 ppm |
| red pepper oleoresin | 5-500 ppm | 5-500 ppm | 50-5000 ppm |
| effervescing agents | 5-500 ppm | 5-500 ppm | 50-5000 ppm |
| Spilanthol | 5-500 ppm | 5-500 ppm | 50-5000 ppm |
| Sanshool | 5-500 ppm | 5-500 ppm | 50-5000 ppm |
| II. Flavors | | | |
| spearmint oil | 0.01-10.0% | 0.01-10.0% | 0.5-30.0% |
| cinnamon oil | 0.01-10.0% | 0.01-10.0% | 0.5-30.0% |
| oil of wintergreen | 0.01-10.0% | 0.01-10.0% | 0.5-30.0% |
| peppermint oil | 0.01-10.0% | 0.01-10.0% | 0.5-30.0% |
| clove oil | 0.01-10.0% | 0.01-10.0% | 0.5-30.0% |
| bay oil | 0.01-10.0% | 0.01-10.0% | 0.5-30.0% |
| anise oil | 0.01-10.0% | 0.01-10.0% | 0.5-30.0% |
| *eucalyptus* oil | 0.01-10.0% | 0.01-10.0% | 0.5-30.0% |
| thyme oil | 0.01-10.0% | 0.01-10.0% | 0.5-30.0% |
| cedar leaf oil | 0.01-10.0% | 0.01-10.0% | 0.5-30.0% |
| oil of nutmeg | 0.01-10.0% | 0.01-10.0% | 0.5-30.0% |
| allspice | 0.01-10.0% | 0.01-10.0% | 0.5-30.0% |
| oil of sage | 0.01-10.0% | 0.01-10.0% | 0.5-30.0% |
| mace | 0.01-10.0% | 0.01-10.0% | 0.5-30.0% |
| oil of bitter almonds | 0.01-10.0% | 0.01-10.0% | 0.5-30.0% |
| *cassia* oil | 0.01-10.0% | 0.01-10.0% | 0.5-30.0% |
| vanilla | 0.01-10.0% | 0.01-10.0% | 0.5-30.0% |

TABLE 2-continued

| Components | Optional Coating or Center-fill | Cooked Saccharide Portion | Elastomeric Portion |
|---|---|---|---|
| lemon | 0.01-10.0% | 0.01-10.0% | 0.5-30.0% |
| orange | 0.01-10.0% | 0.01-10.0% | 0.5-30.0% |
| lime | 0.01-10.0% | 0.01-10.0% | 0.5-30.0% |
| grapefruit | 0.01-10.0% | 0.01-10.0% | 0.5-30.0% |
| apple | 0.01-10.0% | 0.01-10.0% | 0.5-30.0% |
| pear | 0.01-10.0% | 0.01-10.0% | 0.5-30.0% |
| peach | 0.01-10.0% | 0.01-10.0% | 0.5-30.0% |
| grape | 0.01-10.0% | 0.01-10.0% | 0.5-30.0% |
| strawberry | 0.01-10.0% | 0.01-10.0% | 0.5-30.0% |
| raspberry | 0.01-10.0% | 0.01-10.0% | 0.5-30.0% |
| cherry | 0.01-10.0% | 0.01-10.0% | 0.5-30.0% |
| plum | 0.01-10.0% | 0.01-10.0% | 0.5-30.0% |
| pineapple | 0.01-10.0% | 0.01-10.0% | 0.5-30.0% |
| apricot | 0.01-10.0% | 0.01-10.0% | 0.5-30.0% |
| watermelon | 0.01-10.0% | 0.01-10.0% | 0.5-30.0% |
| chocolate | 0.01-10.0% | 0.01-10.0% | 0.5-30.0% |
| cola | 0.01-10.0% | 0.01-10.0% | 0.5-30.0% |
| maple | 0.01-10.0% | 0.01-10.0% | 0.5-30.0% |
| dulce de leche | 0.01-10.0% | 0.01-10.0% | 0.5-30.0% |
| raisin | 0.01-10.0% | 0.01-10.0% | 0.5-30.0% |
| caramel | 0.01-10.0% | 0.01-10.0% | 0.5-30.0% |
| cinnamyl acetate | 0.01-10.0% | 0.01-10.0% | 0.5-30.0% |
| cinnamaldehyde | 0.01-10.0% | 0.01-10.0% | 0.5-30.0% |
| citral diethylacetal | 0.01-10.0% | 0.01-10.0% | 0.5-30.0% |
| dihydrocarvyl acetate | 0.01-10.0% | 0.01-10.0% | 0.5-30.0% |
| eugenyl formate | 0.01-10.0% | 0.01-10.0% | 0.5-30.0% |
| p-methylamisol | 0.01-10.0% | 0.01-10.0% | 0.5-30.0% |
| acetaldehyde | 0.01-10.0% | 0.01-10.0% | 0.5-30.0% |
| benzaldehyde | 0.01-10.0% | 0.01-10.0% | 0.5-30.0% |
| anisic aldehyde | 0.01-10.0% | 0.01-10.0% | 0.5-30.0% |
| cinnamic aldehyde | 0.01-10.0% | 0.01-10.0% | 0.5-30.0% |
| citral | 0.01-10.0% | 0.01-10.0% | 0.5-30.0% |
| neral | 0.01-10.0% | 0.01-10.0% | 0.5-30.0% |
| decanal | 0.01-10.0% | 0.01-10.0% | 0.5-30.0% |
| ethyl vanillin | 0.01-10.0% | 0.01-10.0% | 0.5-30.0% |
| heliotrope | 0.01-10.0% | 0.01-10.0% | 0.5-30.0% |
| vanillin | 0.01-10.0% | 0.01-10.0% | 0.5-30.0% |
| alpha-amyl cinnamaldehyde | 0.01-10.0% | 0.01-10.0% | 0.5-30.0% |
| butyraldehyde | 0.01-10.0% | 0.01-10.0% | 0.5-30.0% |
| valeraldehyde | 0.01-10.0% | 0.01-10.0% | 0.5-30.0% |
| citronellal | 0.01-10.0% | 0.01-10.0% | 0.5-30.0% |
| decanal | 0.01-10.0% | 0.01-10.0% | 0.5-30.0% |
| aldehyde C-8 | 0.01-10.0% | 0.01-10.0% | 0.5-30.0% |
| aldehyde C-9 | 0.01-10.0% | 0.01-10.0% | 0.5-30.0% |
| aldehyde C-12 | 0.01-10.0% | 0.01-10.0% | 0.5-30.0% |
| 2-ethyl butyraldehyde | 0.01-10.0% | 0.01-10.0% | 0.5-30.0% |
| hexenal | 0.01-10.0% | 0.01-10.0% | 0.5-30.0% |
| tolyl aldehyde | 0.01-10.0% | 0.01-10.0% | 0.5-30.0% |
| veratraldehyde | 0.01-10.0% | 0.01-10.0% | 0.5-30.0% |
| 2,6-dimethyl-5-heptenal | 0.01-10.0% | 0.01-10.0% | 0.5-30.0% |
| 2,6-dimethyloctanal | 0.01-10.0% | 0.01-10.0% | 0.5-30.0% |
| 2-dodecenal | 0.01-10.0% | 0.01-10.0% | 0.5-30.0% |
| strawberry shortcake | 0.01-10.0% | 0.01-10.0% | 0.5-30.0% |
| pomegranate | 0.01-10.0% | 0.01-10.0% | 0.5-30.0% |
| beef | 0.01-10.0% | 0.01-10.0% | 0.5-30.0% |
| chicken | 0.01-10.0% | 0.01-10.0% | 0.5-30.0% |
| cheese | 0.01-10.0% | 0.01-10.0% | 0.5-30.0% |
| onion | 0.01-10.0% | 0.01-10.0% | 0.5-30.0% |
| III. Tastes | | | |
| A. Sweeteners | | | |
| sucrose | 5-100% | 5-100% | 5-80% |
| dextrose | 5-100% | 5-100% | 5-80% |
| maltose | 5-100% | 5-100% | 5-80% |
| dextrin | 5-100% | 5-100% | 5-80% |
| xylose | 5-100% | 5-100% | 5-80% |
| ribose | 5-100% | 5-100% | 5-80% |
| glucose | 5-100% | 5-100% | 5-80% |
| mannose | 5-100% | 5-100% | 5-80% |
| galactose | 5-100% | 5-100% | 5-80% |
| fructose | 5-100% | 5-100% | 5-80% |
| invert sugar | 5-100% | 5-100% | 5-80% |
| fructo oligo saccharide syrups | 5-100% | 5-100% | 5-80% |
| partially hydrolyzed starch | 5-100% | 5-100% | 5-80% |
| corn syrup solids | 5-100% | 5-100% | 5-80% |
| sorbitol | 5-100% | 5-100% | 5-80% |
| xylitol | 5-100% | 5-100% | 5-80% |

TABLE 2-continued

| Components | Optional Coating or Center-fill | Cooked Saccharide Portion | Elastomeric Portion |
|---|---|---|---|
| mannitol | 5-100% | 5-100% | 5-80% |
| galactitol | 5-100% | 5-100% | 5-80% |
| maltitol | 5-100% | 5-100% | 5-80% |
| Isomalt | 5-100% | 5-100% | 5-80% |
| lactitol | 5-100% | 5-100% | 5-80% |
| erythritol | 5-100% | 5-100% | 5-80% |
| hydrogenated starch hydrolysate | 5-100% | 5-100% | 5-80% |
| stevia | 10-20,000 ppm | 10-20,000 ppm | 10-20,000 ppm |
| dihydrochalcones | 10-20,000 ppm | 10-20,000 ppm | 10-20,000 ppm |
| monellin | 10-20,000 ppm | 10-20,000 ppm | 10-20,000 ppm |
| steviosides | 10-20,000 ppm | 10-20,000 ppm | 10-20,000 ppm |
| glycyrrhizin | 10-20,000 ppm | 10-20,000 ppm | 10-20,000 ppm |
| dihydroflavenol | 10-20,000 ppm | 10-20,000 ppm | 10-20,000 ppm |
| L-aminodicarboxylic acid aminoalkenoic acid ester amides | 10-20,000 ppm | 10-20,000 ppm | 10-20,000 ppm |
| sodium or calcium saccharin salts | 10-20,000 ppm | 10-20,000 ppm | 10-20,000 ppm |
| cyclamate salts | 10-20,000 ppm | 10-20,000 ppm | 10-20,000 ppm |
| sodium, ammonium or calcium salt of 3,4-dihydro-6-methyl-1,2,3-oxathiazine-4-one-2,2-dioxide | 10-20,000 ppm | 10-20,000 ppm | 10-20,000 ppm |
| Acesulfame-K | 10-20,000 ppm | 10-20,000 ppm | 10-20,000 ppm |
| free acid form of saccharin | 10-20,000 ppm | 10-20,000 ppm | 10-20,000 ppm |
| Aspartame | 10-20,000 ppm | 10-20,000 ppm | 10-20,000 ppm |
| Alitame | 10-20,000 ppm | 10-20,000 ppm | 10-20,000 ppm |
| Neotame | 10-20,000 ppm | 10-20,000 ppm | 10-20,000 ppm |
| methyl esters of L-aspartyl-L-phenylglycerine and L-aspartyl-L-2,5-dihydrophenyl-glycine | 10-20,000 ppm | 10-20,000 ppm | 10-20,000 ppm |
| L-aspartyl-2,5-dihydro-L-phenylalanine | 10-20,000 ppm | 10-20,000 ppm | 10-20,000 ppm |
| L-aspartyl-L-(1-cyclohexen)-alanine | 10-20,000 ppm | 10-20,000 ppm | 10-20,000 ppm |
| Sucralose | 10-20,000 ppm | 10-20,000 ppm | 10-20,000 ppm |
| 1-chloro-1'-deoxysucrose | 10-20,000 ppm | 10-20,000 ppm | 10-20,000 ppm |
| 4-chloro-4-deoxy-alpha-D-galactopyranosyl-alpha-D-fructofuranoside | 10-20,000 ppm | 10-20,000 ppm | 10-20,000 ppm |
| 4-chloro-4-deoxygalactosucrose | 10-20,000 ppm | 10-20,000 ppm | 10-20,000 ppm |
| 4-chloro-4-deoxy-alpha-D-galactopyranosyl-1-chloro-1-deoxy-beta-D-fructo-furanoside | 10-20,000 ppm | 10-20,000 ppm | 10-20,000 ppm |
| 4,1'-dichloro-4,1'-dideoxygalactosucrose | 10-20,000 ppm | 10-20,000 ppm | 10-20,000 ppm |
| 1',6'-dichloro1',6'-dideoxysucrose | 10-20,000 ppm | 10-20,000 ppm | 10-20,000 ppm |
| 4-chloro-4-deoxy-alpha-D-galactopyranosyl-1,6-dichloro-1,6-dideoxy-beta-D-fructofuranoside | 10-20,000 ppm | 10-20,000 ppm | 10-20,000 ppm |
| 4,1',6'-trichloro-4,1',6'-trideoxygalactosucrose | 10-20,000 ppm | 10-20,000 ppm | 10-20,000 ppm |
| 4,6-dichloro-4,6-dideoxy-alpha-D-galactopyranosyl-6-chloro-6-deoxy-beta-D-fructofuranoside | 10-20,000 ppm | 10-20,000 ppm | 10-20,000 ppm |
| 4,6,6'-trichloro-4,6,6'-trideoxygalactosucrose | 10-20,000 ppm | 10-20,000 ppm | 10-20,000 ppm |
| 6,1',6'-trichloro-6,1',6'-trideoxysucrose | 10-20,000 ppm | 10-20,000 ppm | 10-20,000 ppm |
| 4,6-dichloro-4,6-dideoxy-alpha-D-galacto-pyranosyl-1,6-dichloro-1,6-dideox y-beta-D-fructofuranoside | 10-20,000 ppm | 10-20,000 ppm | 10-20,000 ppm |
| 4,6,1',6'-tetrachloro4,6,1',6'-tetradeoxygalacto-sucrose | 10-20,000 ppm | 10-20,000 ppm | 10-20,000 ppm |
| 4,6,1',6'-tetradeoxy-sucrose | 10-20,000 ppm | 10-20,000 ppm | 10-20,000 ppm |
| Thaumatin I and II | 10-20,000 ppm | 10-20,000 ppm | 10-20,000 ppm |
| Monatin | 10-20,000 ppm | 10-20,000 ppm | 10-20,000 ppm |
| B. Sour | | | |
| acetic acid | 0.00005-10% | 0.00005-10% | 0.00005-10% |
| adipic acid | 0.00005-10% | 0.00005-10% | 0.00005-10% |
| ascorbic acid | 0.00005-10% | 0.00005-10% | 0.00005-10% |
| butyric acid | 0.00005-10% | 0.00005-10% | 0.00005-10% |
| citric acid | 0.00005-10% | 0.00005-10% | 0.00005-10% |
| formic acid | 0.00005-10% | 0.00005-10% | 0.00005-10% |
| fumaric acid | 0.00005-10% | 0.00005-10% | 0.00005-10% |
| glyconic acid | 0.00005-10% | 0.00005-10% | 0.00005-10% |
| lactic acid | 0.00005-10% | 0.00005-10% | 0.00005-10% |

TABLE 2-continued

| Components | Optional Coating or Center-fill | Cooked Saccharide Portion | Elastomeric Portion |
|---|---|---|---|
| phosphoric acid | 0.00005-10% | 0.00005-10% | 0.00005-10% |
| malic acid | 0.00005-10% | 0.00005-10% | 0.00005-10% |
| oxalic acid | 0.00005-10% | 0.00005-10% | 0.00005-10% |
| succinic acid | 0.00005-10% | 0.00005-10% | 0.00005-10% |
| tartaric acid | 0.00005-10% | 0.00005-10% | 0.00005-10% |
| C. Bitter/Astringent | | | |
| quinine | 0.01-100 ppm | 0.01-100 ppm | 0.01-100 ppm |
| naringin | 0.01-100 ppm | 0.01-100 ppm | 0.01-100 ppm |
| quassia | 0.01-100 ppm | 0.01-100 ppm | 0.01-100 ppm |
| phenyl thiocarbamide (PTC) | 0.01-100 ppm | 0.01-100 ppm | 0.01-100 ppm |
| 6-n-propylthiouracil (Prop) | 0.01-100 ppm | 0.01-100 ppm | 0.01-100 ppm |
| alum | 0.01-100 ppm | 0.01-100 ppm | 0.01-100 ppm |
| salicin | 0.01-100 ppm | 0.01-100 ppm | 0.01-100 ppm |
| caffeine | 0.01-100 ppm | 0.01-100 ppm | 0.01-100 ppm |
| Epigallocatechingallate | 0.01-100 ppm | 0.01-100 ppm | 0.01-100 ppm |
| D. Salty | | | |
| sodium chloride | 0.01-1% | 0.01-1% | 0.01-1% |
| calcium chloride | 0.01-1% | 0.01-1% | 0.01-1% |
| potassium chloride | 0.01-1% | 0.01-1% | 0.01-1% |
| l-lysine | 0.01-1% | 0.01-1% | 0.01-1% |
| IV. Functional agents | | | |
| A. Surfactants | | | |
| salts of fatty acids selected from the group consisting of $C_8$-$C_{24}$ | 0.001-5% | 0.001-5% | 0.001-2% |
| palmitoleic acid | 0.001-5% | 0.001-5% | 0.001-2% |
| oleic acid | 0.001-5% | 0.001-5% | 0.001-2% |
| eleosteric acid | 0.001-5% | 0.001-5% | 0.001-2% |
| butyric acid | 0.001-5% | 0.001-5% | 0.001-2% |
| caproic acid | 0.001-5% | 0.001-5% | 0.001-2% |
| caprylic acid | 0.001-5% | 0.001-5% | 0.001-2% |
| capric acid | 0.001-5% | 0.001-5% | 0.001-2% |
| lauric acid | 0.001-5% | 0.001-5% | 0.001-2% |
| myristic acid | 0.001-5% | 0.001-5% | 0.001-2% |
| palmitic acid | 0.001-5% | 0.001-5% | 0.001-2% |
| stearic acid | 0.001-5% | 0.001-5% | 0.001-2% |
| ricinoleic acid | 0.001-5% | 0.001-5% | 0.001-2% |
| arachidic acid | 0.001-5% | 0.001-5% | 0.001-2% |
| behenic acid | 0.001-5% | 0.001-5% | 0.001-2% |
| lignoceric acid | 0.001-5% | 0.001-5% | 0.001-2% |
| cerotic acid | 0.001-5% | 0.001-5% | 0.001-2% |
| sulfated butyl oleate | 0.001-5% | 0.001-5% | 0.001-2% |
| medium and long chain fatty acid esters | 0.001-2% | 0.001-2% | 0.001-2% |
| sodium oleate | 0.001-2% | 0.001-2% | 0.001-2% |
| salts of fumaric acid | 0.001-2% | 0.001-2% | 0.001-2% |
| potassium glomate | 0.001-2% | 0.001-2% | 0.001-2% |
| organic acid esters of mono- and diglycerides | 0.001-2% | 0.001-2% | 0.001-2% |
| stearyl monoglyceridyl citrate | 0.001-2% | 0.001-2% | 0.001-2% |
| succistearin | 0.001-2% | 0.001-2% | 0.001-2% |
| dioctyl sodium sulfosuccinate | 0.001-2% | 0.001-2% | 0.001-2% |
| glycerol tristearate | 0.001-2% | 0.001-2% | 0.001-2% |
| lecithin | 0.001-2% | 0.001-2% | 0.001-2% |
| hydroxylated lecithin | 0.001-2% | 0.001-2% | 0.001-2% |
| sodium lauryl sulfate | 0.001-2% | 0.001-2% | 0.001-2% |
| acetylated monoglycerides | 0.001-2% | 0.001-2% | 0.001-2% |
| succinylated monoglycerides | 0.001-2% | 0.001-2% | 0.001-2% |
| monoglyceride citrate | 0.001-2% | 0.001-2% | 0.001-2% |
| ethoxylated mono- and diglycerides | 0.001-2% | 0.001-2% | 0.001-2% |
| sorbitan monostearate | 0.001-2% | 0.001-2% | 0.001-2% |
| calcium stearyl-2-lactylate | 0.001-2% | 0.001-2% | 0.001-2% |
| sodium stearyl lactylate | 0.001-2% | 0.001-2% | 0.001-2% |
| lactylated fatty acid esters of glycerol and propylene glycerol | 0.001-2% | 0.001-2% | 0.001-2% |
| glycerol-lactoesters of C8-C24 fatty acids | 0.001-2% | 0.001-2% | 0.001-2% |
| polyglycerol esters of C8-C24 fatty acids | 0.001-2% | 0.001-2% | 0.001-2% |
| propylene glycol alginate | 0.001-2% | 0.001-2% | 0.001-2% |
| sucrose C8-C24 fatty acid esters | 0.001-2% | 0.001-2% | 0.001-2% |
| diacetyl tartaric and citric acid esters of mono- and diglycerides | 0.001-2% | 0.001-2% | 0.001-2% |
| triacetin | 0.001-2% | 0.001-2% | 0.001-2% |

TABLE 2-continued

| Components | Optional Coating or Center-fill | Cooked Saccharide Portion | Elastomeric Portion |
|---|---|---|---|
| sarcosinate surfactants | 0.001-2% | 0.001-2% | 0.001-2% |
| isethionate surfactants | 0.001-2% | 0.001-2% | 0.001-2% |
| tautate surfactants | 0.001-2% | 0.001-2% | 0.001-2% |
| pluronics | 0.001-2% | 0.001-2% | 0.001-2% |
| polyethylene oxide condensates of alkyl phenols | 0.001-2% | 0.001-2% | 0.001-2% |
| products derived from the condensation of ethylene oxide with the reaction product of propylene oxide and ethylene diamine | 0.001-2% | 0.001-2% | 0.001-2% |
| ethylene oxide condensates of aliphatic alcohols | 0.001-2% | 0.001-2% | 0.001-2% |
| long chain tertiary amine oxides | 0.001-2% | 0.001-2% | 0.001-2% |
| long chain tertiary phosphine oxides | 0.001-2% | 0.001-2% | 0.001-2% |
| long chain dialkyl sulfoxides | 0.001-2% | 0.001-2% | 0.001-2% |
| B. Breath freshening agents | | | |
| spearmint oil | 0.001-10% | 0.001-10% | 0.001-10% |
| peppermint oil | 0.001-10% | 0.001-10% | 0.001-10% |
| wintergreen oil | 0.001-10% | 0.001-10% | 0.001-10% |
| *sassafras* oil | 0.001-10% | 0.001-10% | 0.001-10% |
| chlorophyll oil | 0.001-10% | 0.001-10% | 0.001-10% |
| citral oil | 0.001-10% | 0.001-10% | 0.001-10% |
| geraniol oil | 0.001-10% | 0.001-10% | 0.001-10% |
| cardamom oil | 0.001-10% | 0.001-10% | 0.001-10% |
| clove oil | 0.001-10% | 0.001-10% | 0.001-10% |
| sage oil | 0.001-10% | 0.001-10% | 0.001-10% |
| carvacrol oil | 0.001-10% | 0.001-10% | 0.001-10% |
| *eucalyptus* oil | 0.001-10% | 0.001-10% | 0.001-10% |
| cardamom oil | 0.001-10% | 0.001-10% | 0.001-10% |
| *magnolia* bark extract oil | 0.001-10% | 0.001-10% | 0.001-10% |
| marjoram oil | 0.001-10% | 0.001-10% | 0.001-10% |
| cinnamon oil | 0.001-10% | 0.001-10% | 0.001-10% |
| lemon oil | 0.001-10% | 0.001-10% | 0.001-10% |
| lime oil | 0.001-10% | 0.001-10% | 0.001-10% |
| grapefruit oil | 0.001-10% | 0.001-10% | 0.001-10% |
| orange oil | 0.001-10% | 0.001-10% | 0.001-10% |
| cinnamic aldehyde | 0.001-10% | 0.001-10% | 0.001-10% |
| salicylaldehyde | 0.001-10% | 0.001-10% | 0.001-10% |
| menthol | 0.001-10% | 0.001-10% | 0.001-10% |
| carvone | 0.001-10% | 0.001-10% | 0.001-10% |
| iso-garrigol | 0.001-10% | 0.001-10% | 0.001-10% |
| anethole | 0.001-10% | 0.001-10% | 0.001-10% |
| zinc citrate | 0.01-25% | 0.01-25% | 0.1-15% |
| zinc acetate | 0.01-25% | 0.01-25% | 0.1-15% |
| zinc fluoride | 0.01-25% | 0.01-25% | 0.1-15% |
| zinc ammonium sulfate | 0.01-25% | 0.01-25% | 0.1-15% |
| zinc bromide | 0.01-25% | 0.01-25% | 0.1-15% |
| zinc iodide | 0.01-25% | 0.01-25% | 0.1-15% |
| zinc chloride | 0.01-25% | 0.01-25% | 0.1-15% |
| zinc nitrate | 0.01-25% | 0.01-25% | 0.1-15% |
| zinc flurosilicate | 0.01-25% | 0.01-25% | 0.1-15% |
| zinc gluconate | 0.01-25% | 0.01-25% | 0.1-15% |
| zinc tartarate | 0.01-25% | 0.01-25% | 0.1-15% |
| zinc succinate | 0.01-25% | 0.01-25% | 0.1-15% |
| zinc formate | 0.01-25% | 0.01-25% | 0.1-15% |
| zinc chromate | 0.01-25% | 0.01-25% | 0.1-15% |
| zinc phenol sulfonate | 0.01-25% | 0.01-25% | 0.1-15% |
| zinc dithionate | 0.01-25% | 0.01-25% | 0.1-15% |
| zinc sulfate | 0.01-25% | 0.01-25% | 0.1-15% |
| silver nitrate | 0.01-25% | 0.01-25% | 0.1-15% |
| zinc salicylate | 0.01-25% | 0.01-25% | 0.1-15% |
| zinc glycerophosphate | 0.01-25% | 0.01-25% | 0.1-15% |
| copper nitrate | 0.01-25% | 0.01-25% | 0.1-15% |
| chlorophyll | 0.01-25% | 0.01-25% | 0.1-15% |
| copper chlorophyll | 0.01-25% | 0.01-25% | 0.1-15% |
| chlorophyllin | 0.01-25% | 0.01-25% | 0.1-15% |
| hydrogenated cottonseed oil | 0.5-5% | 0.5-70% | 0.5-15% |
| chlorine dioxide | 0.025-0.50% | 0.025-0.50% | 0.025-0.50% |
| beta cyclodextrin | 0.1-5% | 0.1-5% | 0.1-5% |
| zeolite | 0.1-5% | 0.1-5% | 0.1-5% |
| silica-based materials | 0.1-5% | 0.1-5% | 0.1-5% |
| carbon-based materials | 0.1-5% | 0.1-5% | 0.1-5% |
| enzymes such as laccase, papain, krillase, amylase, glucose oxidase | 0.1-5% | 0.1-5% | 0.1-5% |

TABLE 2-continued

| Components | Optional Coating or Center-fill | Cooked Saccharide Portion | Elastomeric Portion |
|---|---|---|---|
| C. Anti-microbial agents | | | |
| cetylpyridinium chloride | 0.01-1% | 0.01-1% | 0.01-1% |
| zinc compounds | 0.01-25% | 0.01-25% | 0.1-15% |
| copper compounds | 0.01-25% | 0.01-25% | 0.1-15% |
| D. Antibacterial agents | | | |
| chlorhexidine | 0.0025-2% | 0.0025-2% | 0.0025-2% |
| alexidine | 0.0025-2% | 0.0025-2% | 0.0025-2% |
| quaternary ammonium salts | 0.0025-2% | 0.0025-2% | 0.0025-2% |
| benzethonium chloride | 0.0025-2% | 0.0025-2% | 0.0025-2% |
| cetyl pyridinium chloride | 0.0025-2% | 0.0025-2% | 0.0025-2% |
| 2,4,4'-trichloro-2'-hydroxy-diphenyl ether (triclosan) | 0.0025-2% | 0.0025-2% | 0.0025-2% |
| E. Anti-calculus agents | | | |
| pyrophosphates | 1-6% | 1-6% | 1-6% |
| triphosphates | 0.1-10% | 0.1-10% | 0.1-10% |
| polyphosphates | 0.1-10% | 0.1-10% | 0.1-10% |
| polyphosphonates | 0.1-10% | 0.1-10% | 0.1-10% |
| dialkali metal pyrophosphate salt | 1-6% | 1-6% | 1-6% |
| tetra alkali polyphosphate salt | 0.1-10% | 0.1-10% | 0.1-10% |
| tetrasodium pyrophosphate | 1-6% | 1-6% | 1-6% |
| tetrapotassium pyrophosphate | 1-6% | 1-6% | 1-6% |
| sodium tripolyphosphate | 0.1-10% | 0.1-10% | 0.1-10% |
| Sodium hexametaphosphate | 0.1-10% | 0.1-10% | 0.1-10% |
| F. Anti-plaque agents | | | |
| chlorhexidine | 0.0025-2% | 0.0025-2% | 0.0025-2% |
| triclosan | 0.01-2% | 0.01-2% | 0.01-2% |
| hexetidine | 0.01-2% | 0.01-2% | 0.01-2% |
| zinc citrate | 0.01-25% | 0.01-25% | 0.1-15% |
| essential oils | 0.001-10% | 0.001-10% | 0.001-10% |
| sodium lauryl sulfate | 0.001-2% | 0.001-2% | 0.001-2% |
| Epigallocatechingallate | 0.001-5% | 0.001-3% | 0.001-2% |
| G. Fluoride compounds | | | |
| sodium fluoride | 0.01-1% | 0.01-1% | 0.01-1% |
| sodium monofluorophosphate | 0.01-1% | 0.01-1% | 0.01-1% |
| stannous fluoride | 0.01-1% | 0.01-1% | 0.01-1% |
| H. Quaternary ammonium compounds | | | |
| Benzalkonium Chloride | 0.01-1% | 0.01-1% | 0.01-1% |
| Benzethonium Chloride | 0.01-1% | 0.01-1% | 0.01-1% |
| Cetalkonium Chloride | 0.01-1% | 0.01-1% | 0.01-1% |
| Cetrimide | 0.01-1% | 0.01-1% | 0.01-1% |
| Cetrimonium Bromide | 0.01-1% | 0.01-1% | 0.01-1% |
| Cetylpyridinium Chloride | 0.01-1% | 0.01-1% | 0.01-1% |
| Glycidyl Trimethyl Ammonium Chloride | 0.01-1% | 0.01-1% | 0.01-1% |
| Stearalkonium Chloride | 0.01-1% | 0.01-1% | 0.01-1% |
| I. Remineralization agents | | | |
| phosphopeptide-amorphous calcium phosphate | 0.1-5% | 0.1-5% | 0.1-5% |
| casein phosphoprotein-calcium phosphate complex | 0.1-5% | 0.1-5% | 0.1-5% |
| casein phosphopeptide-stabilized calcium phosphate | 0.1-5% | 0.1-5% | 0.1-5% |
| J. Pharmaceutical actives | | | |
| drugs or medicaments | 0.0001-10% | 0.0001-10% | 0.0001-10% |
| vitamins and other dietary supplements | 0.0001-10% | 0.0001-10% | 0.0001-10% |
| minerals | 0.0001-10% | 0.0001-10% | 0.0001-10% |
| caffeine | 0.0001-10% | 0.0001-10% | 0.0001-10% |
| nicotine | 0.0001-10% | 0.0001-10% | 0.0001-10% |
| fruit juices | 2-10% | 2-60% | 1-15% |
| K. Micronutrients | | | |
| vitamin A | 0.0001-10% | 0.0001-10% | 0.0001-10% |
| vitamin D | 0.0001-10% | 0.0001-10% | 0.0001-10% |
| vitamin E | 0.0001-10% | 0.0001-10% | 0.0001-10% |
| vitamin K | 0.0001-10% | 0.0001-10% | 0.0001-10% |

TABLE 2-continued

| Components | Optional Coating or Center-fill | Cooked Saccharide Portion | Elastomeric Portion |
|---|---|---|---|
| vitamin C (ascorbic acid) | 0.0001-10% | 0.0001-10% | 0.0001-10% |
| B vitamins (thiamine or B1, riboflavoin or B2, niacin or B3, pyridoxine or B6, folic acid or B9, cyanocobalimin or B12, pantothenic acid, biotin) | 0.0001-10% | 0.0001-10% | 0.0001-10% |
| sodium | 0.0001-10% | 0.0001-10% | 0.0001-10% |
| magnesium | 0.0001-10% | 0.0001-10% | 0.0001-10% |
| chromium | 0.0001-10% | 0.0001-10% | 0.0001-10% |
| iodine | 0.0001-10% | 0.0001-10% | 0.0001-10% |
| iron | 0.0001-10% | 0.0001-10% | 0.0001-10% |
| manganese | 0.0001-10% | 0.0001-10% | 0.0001-10% |
| calcium | 0.0001-10% | 0.0001-10% | 0.0001-10% |
| copper | 0.0001-10% | 0.0001-10% | 0.0001-10% |
| fluoride | 0.0001-10% | 0.0001-10% | 0.0001-10% |
| potassium | 0.0001-10% | 0.0001-10% | 0.0001-10% |
| phosphorous | 0.0001-10% | 0.0001-10% | 0.0001-10% |
| molybdenum | 0.0001-10% | 0.0001-10% | 0.0001-10% |
| selenium | 0.0001-10% | 0.0001-10% | 0.0001-10% |
| zinc | 0.0001-10% | 0.0001-10% | 0.0001-10% |
| L-carnitine | 0.0001-10% | 0.0001-10% | 0.0001-10% |
| choline | 0.0001-10% | 0.0001-10% | 0.0001-10% |
| coenzyme Q10 | 0.0001-10% | 0.0001-10% | 0.0001-10% |
| alpha-lipoic acid | 0.0001-10% | 0.0001-10% | 0.0001-10% |
| omega-3-fatty acids | 0.0001-10% | 0.0001-10% | 0.0001-10% |
| pepsin | 0.0001-10% | 0.0001-10% | 0.0001-10% |
| phytase | 0.0001-10% | 0.0001-10% | 0.0001-10% |
| trypsin | 0.0001-10% | 0.0001-10% | 0.0001-10% |
| lipases | 0.0001-10% | 0.0001-10% | 0.0001-10% |
| proteases | 0.0001-10% | 0.0001-10% | 0.0001-10% |
| cellulases | 0.0001-10% | 0.0001-10% | 0.0001-10% |
| ascorbic acid | 0.0001-10% | 0.0001-10% | 0.0001-10% |
| citric acid | 0.0001-10% | 0.0001-10% | 0.0001-10% |
| rosemary oil | 0.0001-10% | 0.0001-10% | 0.0001-10% |
| vitamin A | 0.0001-10% | 0.0001-10% | 0.0001-10% |
| vitamin E phosphate | 0.0001-10% | 0.0001-10% | 0.0001-10% |
| tocopherols | 0.0001-10% | 0.0001-10% | 0.0001-10% |
| di-alpha-tocopheryl phosphate | 0.0001-10% | 0.0001-10% | 0.0001-10% |
| tocotrienols | 0.0001-10% | 0.0001-10% | 0.0001-10% |
| alpha lipoic acid | 0.0001-10% | 0.0001-10% | 0.0001-10% |
| dihydrolipoic acid | 0.0001-10% | 0.0001-10% | 0.0001-10% |
| xanthophylls | 0.0001-10% | 0.0001-10% | 0.0001-10% |
| beta cryptoxanthin | 0.0001-10% | 0.0001-10% | 0.0001-10% |
| lycopene | 0.0001-10% | 0.0001-10% | 0.0001-10% |
| lutein | 0.0001-10% | 0.0001-10% | 0.0001-10% |
| zeaxanthin | 0.0001-10% | 0.0001-10% | 0.0001-10% |
| beta-carotene | 0.0001-10% | 0.0001-10% | 0.0001-10% |
| carotenes | 0.0001-10% | 0.0001-10% | 0.0001-10% |
| mixed carotenoids | 0.0001-10% | 0.0001-10% | 0.0001-10% |
| polyphenols | 0.0001-10% | 0.0001-10% | 0.0001-10% |
| flavonoids | 0.0001-10% | 0.0001-10% | 0.0001-10% |
| cartotenoids | 0.0001-10% | 0.0001-10% | 0.0001-10% |
| chlorophyll | 0.0001-10% | 0.0001-10% | 0.0001-10% |
| chlorophyllin | 0.0001-10% | 0.0001-10% | 0.0001-10% |
| fiber | 0.0001-10% | 0.0001-10% | 0.0001-10% |
| anthocyanins | 0.0001-10% | 0.0001-10% | 0.0001-10% |
| cyaniding | 0.0001-10% | 0.0001-10% | 0.0001-10% |
| delphinidin | 0.0001-10% | 0.0001-10% | 0.0001-10% |
| malvidin | 0.0001-10% | 0.0001-10% | 0.0001-10% |
| pelargonidin | 0.0001-10% | 0.0001-10% | 0.0001-10% |
| peonidin | 0.0001-10% | 0.0001-10% | 0.0001-10% |
| petunidin | 0.0001-10% | 0.0001-10% | 0.0001-10% |
| flavanols | 0.0001-10% | 0.0001-10% | 0.0001-10% |
| flavonols | 0.0001-10% | 0.0001-10% | 0.0001-10% |
| catechin | 0.0001-10% | 0.0001-10% | 0.0001-10% |
| epicatechin | 0.0001-10% | 0.0001-10% | 0.0001-10% |
| epigallocatechin | 0.0001-10% | 0.0001-10% | 0.0001-10% |
| epigallocatechingallate | 0.0001-10% | 0.0001-10% | 0.0001-10% |
| theaflavins | 0.0001-10% | 0.0001-10% | 0.0001-10% |
| thearubigins | 0.0001-10% | 0.0001-10% | 0.0001-10% |
| proanthocyanins | 0.0001-10% | 0.0001-10% | 0.0001-10% |
| quercetin | 0.0001-10% | 0.0001-10% | 0.0001-10% |
| kaempferol | 0.0001-10% | 0.0001-10% | 0.0001-10% |
| myricetin | 0.0001-10% | 0.0001-10% | 0.0001-10% |
| isorhamnetin | 0.0001-10% | 0.0001-10% | 0.0001-10% |
| flavononeshesperetin | 0.0001-10% | 0.0001-10% | 0.0001-10% |
| naringenin | 0.0001-10% | 0.0001-10% | 0.0001-10% |

TABLE 2-continued

| Components | Optional Coating or Center-fill | Cooked Saccharide Portion | Elastomeric Portion |
|---|---|---|---|
| eriodictyol | 0.0001-10% | 0.0001-10% | 0.0001-10% |
| tangeretin | 0.0001-10% | 0.0001-10% | 0.0001-10% |
| flavones | 0.0001-10% | 0.0001-10% | 0.0001-10% |
| apigenin | 0.0001-10% | 0.0001-10% | 0.0001-10% |
| luteolin | 0.0001-10% | 0.0001-10% | 0.0001-10% |
| lignans | 0.0001-10% | 0.0001-10% | 0.0001-10% |
| phytoestrogens | 0.0001-10% | 0.0001-10% | 0.0001-10% |
| resveratrol | 0.0001-10% | 0.0001-10% | 0.0001-10% |
| isoflavones | 0.0001-10% | 0.0001-10% | 0.0001-10% |
| daidzein | 0.0001-10% | 0.0001-10% | 0.0001-10% |
| genistein | 0.0001-10% | 0.0001-10% | 0.0001-10% |
| soy isoflavones | 0.0001-10% | 0.0001-10% | 0.0001-10% |
| L. Throat care actives (1) analgesics, anesthetics, antipyretic and anti-inflammatory agents | | | |
| menthol | 10-500 ppm | 10-500 ppm | 500-20,000 ppm |
| phenol | 0.1-10% | 0.1-50% | 0.1-20% |
| hexylresorcinol | 0.1-10% | 0.1-50% | 0.1-20% |
| benzocaine | 0.1-10% | 0.1-50% | 0.1-20% |
| dyclonine hydrochloride | 0.1-10% | 0.1-50% | 0.1-20% |
| benzyl alcohol | 0.1-10% | 0.1-50% | 0.1-20% |
| salicyl alcohol | 0.1-10% | 0.1-50% | 0.1-20% |
| acetaminophen | 0.1-10% | 0.1-50% | 0.1-20% |
| aspirin | 0.1-10% | 0.1-50% | 0.1-20% |
| diclofenac | 0.1-10% | 0.1-50% | 0.1-20% |
| diflunisal | 0.1-10% | 0.1-50% | 0.1-20% |
| etodolac | 0.1-10% | 0.1-50% | 0.1-20% |
| fenoprofen | 0.1-10% | 0.1-50% | 0.1-20% |
| flurbiprofen | 0.1-10% | 0.1-50% | 0.1-20% |
| ibuprofen | 0.1-10% | 0.1-50% | 0.1-20% |
| ketoprofen | 0.1-10% | 0.1-50% | 0.1-20% |
| ketorolac | 0.1-10% | 0.1-50% | 0.1-20% |
| nabumetone | 0.1-10% | 0.1-50% | 0.1-20% |
| naproxen | 0.1-10% | 0.1-50% | 0.1-20% |
| piroxicam | 0.1-10% | 0.1-50% | 0.1-20% |
| caffeine | 0.0001-10% | 0.0001-10% | 0.0001-10% |
| lidocaine | 0.1-10% | 0.1-50% | 0.1-20% |
| benzocaine | 0.1-10% | 0.1-50% | 0.1-20% |
| phenol | 0.1-10% | 0.1-50% | 0.1-20% |
| dyclonine | 0.1-10% | 0.1-50% | 0.1-20% |
| benzonotate | 0.1-10% | 0.1-50% | 0.1-20% |
| (2) demulcents | | | |
| slippery elm bark | 0.1-10% | 0.1-10% | 0.1-10% |
| pectin | 0.1-10% | 0.1-10% | 0.1-10% |
| gelatin | 0.1-10% | 0.1-10% | 0.1-10% |
| (3) antiseptics | | | |
| cetylpyridinium chloride | 0.01-1% | 0.01-1% | 0.01-1% |
| domiphen bromide | 0.01-1% | 0.01-1% | 0.01-1% |
| dequalinium chloride | 0.01-1% | 0.01-1% | 0.01-1% |
| (4) antitussives | | | |
| chlophedianol hydrochloride | 0.0001-2% | 0.0001-2% | 0.0001-2% |
| codeine | 0.0001-2% | 0.0001-2% | 0.0001-2% |
| codeine phosphate | 0.0001-2% | 0.0001-2% | 0.0001-2% |
| codeine sulfate | 0.0001-2% | 0.0001-2% | 0.0001-2% |
| dextromethorphan | 0.0001-2% | 0.0001-2% | 0.0001-2% |
| dextromethorphan hydrobromide | 0.0001-2% | 0.0001-2% | 0.0001-2% |
| diphenhydramine citrate | 0.0001-2% | 0.0001-2% | 0.0001-2% |
| diphenhydramine hydrochloride | 0.0001-2% | 0.0001-2% | 0.0001-2% |
| dextrorphan | 0.0001-2% | 0.0001-2% | 0.0001-2% |
| diphenhydramine | 0.0001-2% | 0.0001-2% | 0.0001-2% |
| hydrocodone | 0.0001-2% | 0.0001-2% | 0.0001-2% |
| noscapine | 0.0001-2% | 0.0001-2% | 0.0001-2% |
| oxycodone | 0.0001-2% | 0.0001-2% | 0.0001-2% |
| pentoxyverine | 0.0001-2% | 0.0001-2% | 0.0001-2% |
| (5) throat soothing agents | | | |
| honey | 0.5-25% | 0.5-90% | 0.5-15% |
| propolis | 0.1-10% | 0.1-10% | 0.1-10% |
| aloe vera | 0.1-10% | 0.1-10% | 0.1-10% |
| glycerine | 0.1-10% | 0.1-10% | 0.1-10% |
| menthol | 10-500 ppm | 10-500 ppm | 500-20,000 ppm |

TABLE 2-continued

| Components | Optional Coating or Center-fill | Cooked Saccharide Portion | Elastomeric Portion |
|---|---|---|---|
| (6) cough suppressants | | | |
| codeine | 0.0001-2% | 0.0001-2% | 0.0001-2% |
| antihistamines | 0.0001-2% | 0.0001-2% | 0.0001-2% |
| dextromethorphan | 0.0001-2% | 0.0001-2% | 0.0001-2% |
| isoproterenol | 0.0001-2% | 0.0001-2% | 0.0001-2% |
| (7) expectorants | | | |
| ammonium chloride | 0.0001-2% | 0.0001-2% | 0.0001-2% |
| guaifenesin | 0.0001-2% | 0.0001-2% | 0.0001-2% |
| ipecac fluid extract | 0.0001-2% | 0.0001-2% | 0.0001-2% |
| potassium iodide | 0.0001-2% | 0.0001-2% | 0.0001-2% |
| (8) mucolytics | | | |
| acetylcycsteine | 0.0001-2% | 0.0001-2% | 0.0001-2% |
| ambroxol | 0.0001-2% | 0.0001-2% | 0.0001-2% |
| bromhexine | 0.0001-2% | 0.0001-2% | 0.0001-2% |
| (9) antihistamines | | | |
| acrivastine | 0.05-10% | 0.05-10% | 0.05-10% |
| azatadine | 0.05-10% | 0.05-10% | 0.05-10% |
| brompheniramine | 0.05-10% | 0.05-10% | 0.05-10% |
| chlorpheniramine | 0.05-10% | 0.05-10% | 0.05-10% |
| clemastine | 0.05-10% | 0.05-10% | 0.05-10% |
| cyproheptadine | 0.05-10% | 0.05-10% | 0.05-10% |
| dexbrompheniramine | 0.05-10% | 0.05-10% | 0.05-10% |
| dimenhydrinate | 0.05-10% | 0.05-10% | 0.05-10% |
| diphenhydramine | 0.05-10% | 0.05-10% | 0.05-10% |
| doxylamine | 0.05-10% | 0.05-10% | 0.05-10% |
| hydroxyzine | 0.05-10% | 0.05-10% | 0.05-10% |
| meclizine | 0.05-10% | 0.05-10% | 0.05-10% |
| phenindamine | 0.05-10% | 0.05-10% | 0.05-10% |
| phenyltoloxamine | 0.05-10% | 0.05-10% | 0.05-10% |
| promethazine | 0.05-10% | 0.05-10% | 0.05-10% |
| pyrilamine | 0.05-10% | 0.05-10% | 0.05-10% |
| tripelennamine | 0.05-10% | 0.05-10% | 0.05-10% |
| triprolidine | 0.05-10% | 0.05-10% | 0.05-10% |
| astemizole | 0.05-10% | 0.05-10% | 0.05-10% |
| cetirizine | 0.05-10% | 0.05-10% | 0.05-10% |
| ebastine | 0.05-10% | 0.05-10% | 0.05-10% |
| fexofenadine | 0.05-10% | 0.05-10% | 0.05-10% |
| loratidine | 0.05-10% | 0.05-10% | 0.05-10% |
| terfenadine | 0.05-10% | 0.05-10% | 0.05-10% |
| (10) nasal decongestants | | | |
| phenylpropanolamine | 0.1-10% | 0.1-50% | 0.1-20% |
| pseudoephedrine | 0.1-10% | 0.1-50% | 0.1-20% |
| ephedrine | 0.1-10% | 0.1-50% | 0.1-20% |
| phenylephrine | 0.1-10% | 0.1-50% | 0.1-20% |
| oxymetazoline | 0.1-10% | 0.1-50% | 0.1-20% |
| menthol | 0.1-10% | 0.1-50% | 0.1-20% |
| camphor | 0.1-10% | 0.1-50% | 0.1-20% |
| borneol | 0.1-10% | 0.1-50% | 0.1-20% |
| ephedrine | 0.1-10% | 0.1-50% | 0.1-20% |
| *eucalyptus* oil | 0.001-10% | 0.001-10% | 0.001-10% |
| peppermint oil | 0.001-10% | 0.001-10% | 0.001-10% |
| methyl salicylate | 0.001-10% | 0.001-10% | 0.001-10% |
| bornyl acetate | 0.001-10% | 0.001-10% | 0.001-10% |
| lavender oil | 0.001-10% | 0.001-10% | 0.001-10% |
| wasabi extracts | 0.001-10% | 0.001-10% | 0.001-10% |
| horseradish extracts | 0.001-10% | 0.001-10% | 0.001-10% |
| M. Tooth whitening/Stain removing agents | | | |
| surfactants | 0.001-5% | 0.001-5% | 0.001-5% |
| chelators | 0.1-10% | 0.1-10% | 0.1-10% |
| abrasives | 0.1-5% | 0.1-5% | 0.1-20% |
| oxidizing agents | 0.1-5% | 0.1-5% | 0.1-5% |
| hydrolytic agents | 0.1-5% | 0.1-5% | 0.1-5% |
| N. Energy boosting agents | | | |
| caffeine | 0.0001-10% | 0.0001-10% | 0.0001-10% |
| vitamins | 0.0001-10% | 0.0001-10% | 0.0001-10% |
| minerals | 0.0001-10% | 0.0001-10% | 0.0001-10% |
| amino acids | 0.0001-10% | 0.0001-10% | 0.0001-10% |
| ginseng extract | 0.0001-10% | 0.0001-10% | 0.0001-10% |
| ginko extract | 0.0001-10% | 0.0001-10% | 0.0001-10% |

TABLE 2-continued

| Components | Optional Coating or Center-fill | Cooked Saccharide Portion | Elastomeric Portion |
|---|---|---|---|
| guarana extract | 0.0001-10% | 0.0001-10% | 0.0001-10% |
| green tea extract | 0.0001-10% | 0.0001-10% | 0.0001-10% |
| taurine | 0.0001-10% | 0.0001-10% | 0.0001-10% |
| kola nut extract | 0.0001-10% | 0.0001-10% | 0.0001-10% |
| yerba mate leaf | 0.0001-10% | 0.0001-10% | 0.0001-10% |
| Niacin | 0.0001-10% | 0.0001-10% | 0.0001-10% |
| rhodiola root extract | 0.0001-10% | 0.0001-10% | 0.0001-10% |
| O. Concentration boosting agents | | | |
| caffeine | 0.0001-10% | 0.0001-10% | 0.0001-10% |
| ginko extract | 0.0001-10% | 0.0001-10% | 0.0001-10% |
| gotu cola (*centella asiatica*) | 0.0001-10% | 0.0001-10% | 0.0001-10% |
| German chamomile | 0.0001-10% | 0.0001-10% | 0.0001-10% |
| *avina sativa* | 0.0001-10% | 0.0001-10% | 0.0001-10% |
| phosphatidyl serine | 0.0001-10% | 0.0001-10% | 0.0001-10% |
| *aspalathus linearis* | 0.0001-10% | 0.0001-10% | 0.0001-10% |
| pregnenolone | 0.0001-10% | 0.0001-10% | 0.0001-10% |
| *rhodiola* root extract | 0.0001-10% | 0.0001-10% | 0.0001-10% |
| theanine | 0.0001-10% | 0.0001-10% | 0.0001-10% |
| vinpocetine | 0.0001-10% | 0.0001-10% | 0.0001-10% |
| P. Appetite suppressants | | | |
| caffeine | 0.0001-10% | 0.0001-10% | 0.0001-10% |
| guarana extract | 0.0001-10% | 0.0001-10% | 0.0001-10% |
| *hoodia gordonii* | 0.0001-10% | 0.0001-10% | 0.0001-10% |
| glucomannan | 0.0001-10% | 0.0001-10% | 0.0001-10% |
| calcium | 0.0001-10% | 0.0001-10% | 0.0001-10% |
| *garcinia cambogia* extract | 0.0001-10% | 0.0001-10% | 0.0001-10% |
| n-acetyl-tyrosine | 0.0001-10% | 0.0001-10% | 0.0001-10% |
| soy phospholipids | 0.0001-10% | 0.0001-10% | 0.0001-10% |
| Green tea extract (epigallocatechingallate) | 0.0001-10% | 0.0001-10% | 0.0001-10% |
| V. Colors | | | |
| Annatto extract | 0.5-10% | 0.5-20% | 0.5-10% |
| Beta-carotene | 0.5-10% | 0.5-20% | 0.5-10% |
| Canthaxanthin | 0.5-10% | 0.5-20% | 0.5-10% |
| Grape color extract | 0.5-10% | 0.5-20% | 0.5-10% |
| Turmeric oleoresin | 0.5-10% | 0.5-20% | 0.5-10% |
| B-Apo-8'-carotenal | 0.5-10% | 0.5-20% | 0.5-10% |
| Beet powder | 0.5-10% | 0.5-20% | 0.5-10% |
| Caramel color | 0.5-10% | 0.5-20% | 0.5-10% |
| Carmine | 0.5-10% | 0.5-20% | 0.5-10% |
| Cochineal extract | 0.5-10% | 0.5-20% | 0.5-10% |
| Grape skin extract | 0.5-10% | 0.5-20% | 0.5-10% |
| Saffron | 0.5-10% | 0.5-20% | 0.5-10% |
| Tumeric | 0.5-10% | 0.5-20% | 0.5-10% |
| Titanium dioxide | 0.05-2% | 0.05-2% | 0.05-2% |
| F.D. & C. Blue No. 1 | 0.05-2% | 0.05-2% | 0.05-2% |
| F.D.& C. Blue No. 2 | 0.05-2% | 0.05-2% | 0.05-2% |
| F.D.& C. Green No. 1 | 0.05-2% | 0.05-2% | 0.05-2% |
| F.D. & C. Red No. 40 | 0.05-2% | 0.05-2% | 0.05-2% |
| F.D. & C. Red No. 3 | 0.05-2% | 0.05-2% | 0.05-2% |
| F.D. & C. Yellow No. 6 | 0.05-2% | 0.05-2% | 0.05-2% |
| F.D. & C. Yellow No. 5 | 0.05-2% | 0.05-2% | 0.05-2% |

As mentioned above, some embodiments described herein may include more than one duality in the confectionery composition. Such compositions may be referred to as multi-modality compositions. In some embodiments, more than one duality of the same type may be included, such as, two different flavor dualities. Alternatively, different types of dualities may be combined in a single confectionery composition. For example, a flavor duality and a sensation duality may be used together. Further, three or even four of the different duality types may be included in one confectionery composition in some embodiments.

Cooked Saccharide Portion

As described above, components that create multi-modal effects may be added to various portions of a confectionery composition. In some embodiments, confectionery products are formed by combining cooked saccharide (sugar or sugar free) syrups with elastomeric and other ingredients such as flavor, color, etc. In other embodiments, a cooked saccharide portion includes cooked saccharide (sugar or sugar free) syrups along with other ingredients such as, but not limited to, starches, fats, and hydrocolloids. As described in more detail below in the "Texture Modification" section, in some embodiments, the composition of the cooked saccharide portion is influenced by the composition of the elastomeric portion.

In some embodiments, the cooked syrups include saccharides with low hygroscopicity and low tendency to crystallize such that when combined with elastomeric, the resultant chewing confectionery products demonstrate desired shelf life stability. Examples of such cooked syrups include sugar/ corn syrup blends, isomalt, erythritol, maltitol, and combinations of these saccharides. In some embodiments, the tendency of the saccharides to crystallize is exploited by seeding the cooked syrup such that the saccharides crystallize over time to adjust the texture from a harder texture during manufacture to a softer texture at the time of consumption.

In some embodiments, a cooked saccharide portion can include confectionery compositions. Such confectionery compositions can include, but are not limited to, chocolate, compound coating, carob coating, cocoa butter, butter fat, hydrogenated vegetable fat, illipe butter, fondant including fondant-based cremes, fudge, frappe, caramel, nougat, compressed tablet, candy floss (also known as cotton candy), marzipan, hard boiled candy, gummy candy, jelly beans, toffees, taffy, jellies including pectin-based gels, jams, preserves, butterscotch, nut brittles or croquant, candied fruit, marshmallow, pastilles, pralines or nougats, flour or starch confectionery, truffles, nonpareils, bon bons, after-dinner mints, fourres, nut pastes, peanut butter, chewing gum, kisses, angel kisses, montelimart, nougatine, fruit chews, Turkish delight, hard gummies, soft gummies, starch jellies, gelatin jellies, agar jellies, persipan, coconut paste, coconut ice, lozenges, cachous, crème paste, dragees, sugared nuts, sugared almonds, comfits, aniseed balls, licorice, licorice paste, chocolate spreads, chocolate crumb, and combinations thereof.

In some embodiments, the cooked saccharide portion may contain those traditional ingredients well known in the confectionery arts, such as flavoring agents, sweetening agents, and the like, and mixtures thereof, as described above. In addition to confectionery additives, the cooked saccharide portion may also contain pharmaceutical additives such as medicaments, breath fresheners, vitamins, minerals, caffeine, phytochemicals, nutraceuticals, fruit juices, and the like, and mixtures thereof. The confectionery and pharmaceutical agents may be used in many distinct physical forms well known in the art to provide an initial burst of sweetness and flavor and/or therapeutic activity or a prolonged sensation of sweetness and flavor and/or therapeutic activity. Without being limited thereto, such physical forms include free forms, such as spray dried, powdered, and beaded forms, and encapsulated forms, and mixtures thereof. Specific examples of suitable additional components include taurine, guarana, vitamins, Actizol™, chlorophyll, Recaldent™ tooth remineralization technology, and Retsyn™ breath freshening technology.

Elastomeric Portion

The elastomeric portion, also referred to as a second portion, may include at least one modified release component, as discussed in more detail below. Moreover, in some embodiments, the elastomeric portion may include a component that exhibits modified release properties in combination with the same component in its free, or unmodified, form.

The elastomeric portion may be varied to provide a range of characteristics. For example, in some embodiments, an elastomeric portion can include a level of mineral adjuvant or filler that provides a desired chewing texture and is higher than an elastomeric portion with a lesser amount of filler. In other embodiments, an elastomeric portion can include low melting point fats that provides an unctuous mouthfeel and indulgent chewing experience.

The elastomeric portion may include a gum base and/or other elastomeric materials. The gum base or elastomeric materials may include any component known in the chewing gum art. For example, the elastomeric portion may include elastomers, bulking agents, waxes, elastomer solvents, emulsifiers, plasticizers, fillers and mixtures thereof. Wherein the elastomeric portion is included in a dual component composition including a cooked saccharide portion and an elastomeric portion, the elastomeric portion may comprise from about 5% to about 95%, more specifically from about 30% to about 70% by weight of the confectionery composition piece, even more specifically about 50%.

The amount of the gum base or elastomeric material which is present in the elastomeric portion may also vary. In some embodiments, the gum base or elastomeric materials may be included in the elastomeric portion in an amount from about 25% to about 100% by weight of the elastomeric portion. A more specific range of gum base or elastomeric materials in some embodiments may be from about 30% to about 75% by weight of the elastomeric portion. Even more specifically, the range may be from about 35% to about 65% or from about 40% to about 50% in some embodiments.

The elastomers (rubbers) employed in the elastomeric portion will vary greatly depending upon various factors such as the type of elastomeric portion desired, the consistency of elastomeric portion desired and the other components used in the elastomeric portion to make the final confectionery product. The elastomer may be any water-insoluble polymer known in the art, and includes those polymers utilized for chewing gums and bubble gums. Illustrative examples of suitable polymers in gum bases include both natural and synthetic elastomers. For example, those polymers which are suitable in elastomeric portion compositions include, without limitation, natural substances (of vegetable origin) such as chicle, natural rubber, crown gum, nispero, rosidinha, jelutong, perillo, niger gutta, tunu, balata, guttapercha, lechi capsi, sorva, gutta kay, and the like, and combinations thereof. Examples of synthetic elastomers include, without limitation, styrene-butadiene copolymers (SBR), polyisobutylene, isobutylene-isoprene copolymers, polyethylene, polyvinyl acetate and the like, and combinations thereof.

Additional useful polymers include: crosslinked polyvinyl pyrrolidone, polymethylmethacrylate; copolymers of lactic acid, polyhydroxyalkanoates, plasticized ethylcellulose, polyvinyl acetatephthalate and combinations thereof.

The amount of elastomer employed in the elastomeric portion may vary depending upon various factors such as the type of elastomer used, the consistency of the elastomeric portion desired and the other components used in the elastomeric portion to make the final confectionery product. In general, the elastomer will be present in the elastomeric portion in an amount from about 10% to about 60% by weight of the elastomeric portion, desirably from about 35% to about 40% by weight.

In some embodiments, the elastomeric portion may include wax. It softens the polymeric mixture and improves the elasticity of the elastomeric portion. When present, the waxes employed will have a melting point below about 60° C., and preferably between about 45° C. and about 55° C. The low melting wax may be a paraffin wax. The wax may be present in the elastomeric portion in an amount from about 6% to about 10%, and preferably from about 7% to about 9.5%, by weight of the elastomeric portion.

In addition to the low melting point waxes, waxes having a higher melting point may be used in the elastomeric portion in amounts up to about 5%, by weight of the elastomeric portion. Such high melting waxes include beeswax, vegetable wax, candelilla wax, carnuba wax, most petroleum waxes, and the like, and mixtures thereof.

In addition to the components set out above, the elastomeric portion may include a variety of other ingredients, such as components selected from elastomer solvents, emulsifiers, plasticizers, fillers, and mixtures thereof.

The elastomeric portion may contain elastomer solvents to aid in softening the elastomeric materials. Such elastomer solvents may include those elastomer solvents known in the art, for example, terpinene resins such as polymers of alpha-pinene or beta-pinene, methyl, glycerol and pentaerythritol esters of rosins and modified rosins and gums such as hydrogenated, dimerized and polymerized rosins, and mixtures thereof. Examples of elastomer solvents suitable for use herein may include the pentaerythritol ester of partially hydrogenated wood and gum rosin, the pentaerythritol ester of wood and gum rosin, the glycerol ester of wood rosin, the glycerol ester of partially dimerized wood and gum rosin, the glycerol ester of polymerized wood and gum rosin, the glycerol ester of tall oil rosin, the glycerol ester of wood and gum rosin and the partially hydrogenated wood and gum rosin and the partially hydrogenated methyl ester of wood and rosin, and the like, and mixtures thereof. The elastomer solvent may be employed in the elastomeric portion in amounts from about 2% to about 15%, and preferably from about 7% to about 11%, by weight of the elastomeric portion.

The elastomeric portion may also include emulsifiers which aid in dispersing the immiscible components into a single stable system. The emulsifiers useful in this invention include glyceryl monostearate, lecithin, fatty acid monoglycerides, diglycerides, propylene glycol monostearate, and the like, and mixtures thereof. The emulsifier may be employed in amounts from about 2% to about 15%, and more specifically, from about 7% to about 11%, by weight of the elastomeric portion.

The elastomeric portion may also include plasticizers or softeners to provide a variety of desirable textures and consistency properties. Because of the low molecular weight of these ingredients, the plasticizers and softeners are able to penetrate the fundamental structure of the elastomeric portion making it plastic and less viscous. Useful plasticizers and softeners include lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, and the like, and mixtures thereof. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like, may also be incorporated into the elastomeric portion. The plasticizers and softeners are generally employed in the elastomeric portion in amounts up to about 20% by weight of the elastomeric portion, and more specifically in amounts from about 9% to about 17%, by weight of the elastomeric portion.

Plasticizers also include are the hydrogenated vegetable oils and include soybean oil and cottonseed oil which may be employed alone or in combination. These plasticizers provide the elastomeric portion with good texture and soft chew characteristics. These plasticizers and softeners are generally employed in amounts from about 5% to about 14%, and more specifically in amounts from about 5% to about 13.5%, by weight of the elastomeric portion.

Anhydrous glycerin may also be employed as a softening agent, such as the commercially available United States Pharmacopeia (USP) grade. Glycerin is a syrupy liquid with a sweet warm taste and has a sweetness of about 60% of that of cane sugar. Because glycerin is hygroscopic, the anhydrous glycerin may be maintained under anhydrous conditions throughout the preparation of the confectionery composition.

In some embodiments, the elastomeric portion of this invention may also include effective amounts of bulking agents such as mineral adjuvants which may serve as fillers and textural agents. Useful mineral adjuvants include calcium carbonate, magnesium carbonate, alumina, aluminum hydroxide, aluminum silicate, talc, tricalcium phosphate, dicalcium phosphate, calcium sulfate and the like, and mixtures thereof. These fillers or adjuvants may be used in the elastomeric portion in various amounts. The amount of filler, may be present in an amount from about zero to about 40%, and more specifically from about zero to about 30%, by weight of the elastomeric portion. In some embodiments, the amount of filler will be from about zero to about 15%, more specifically from about 3% to about 11%.

A variety of traditional ingredients may be optionally included in the elastomeric portion in effective amounts such as coloring agents, antioxidants, preservatives, flavoring agents, high intensity sweeteners, and the like. For example, titanium dioxide and other dyes suitable for food, drug and cosmetic applications, known as F. D. & C. dyes, may be utilized. An anti-oxidant such as butylated hydroxytoluene (BHT), butylated hydroxyanisole (BHA), propyl gallate, and mixtures thereof, may also be included. Other conventional confectionery additives known to one having ordinary skill in the confectionery art may also be used in the elastomeric portion. A variety of components which may be added to the elastomeric portion, or alternatively to the cooked saccharide portion, center-fill, or coating portions are described in greater detail in the section entitled "Additional Components" hereinbelow.

Some embodiments extend to methods of making the confectionery compositions. The manner in which the elastomeric portion components are mixed is not critical and is performed using standard techniques and apparatus known to those skilled in the art. In a typical method, an elastomer is admixed with an elastomer solvent and/or a plasticizer and/or an emulsifier and agitated for a period of from 1 to 30 minutes. The remaining ingredients, such as the low melting point wax, are then admixed, either in bulk or incrementally, while the elastomeric portion mixture is blended again for 1 to 30 minutes.

The elastomeric portion may include amounts of conventional additives selected from the group consisting of sweetening agents (sweeteners), plasticizers, softeners, emulsifiers, waxes, fillers, bulking agents (carriers, extenders, bulk sweeteners), mineral adjuvants, flavoring agents (flavors, flavorings), coloring agents (colorants, colorings), antioxidants, acidulants, thickeners, medicaments, and the like, and mixtures thereof. Some of these additives may serve more than one purpose. For example, in sugarless confectionery compositions, a sweetener, such as maltitol or other sugar alcohol, may also function as a bulking agent.

The plasticizers, softening agents, mineral adjuvants, waxes and antioxidants discussed above, as being suitable for use in the elastomeric portion, may also be used in the confectionery composition. Examples of other conventional additives which may be used include emulsifiers, such as lecithin and glyceryl monostearate, thickeners, used alone or in combination with other softeners, such as methyl cellulose, alginates, carrageenan, xanthan gum, gelatin, carob, tragacanth, locust bean gum, pectin, alginates, galactomannans such as guar gum, carob bean gum, glucomannan, gelatin, starch, starch derivatives, dextrins and cellulose derivatives such as carboxy methyl cellulose, acidulants such as malic acid, adipic acid, citric acid, tartaric acid, fumaric acid, and mixtures thereof, and fillers, such as those discussed above under the category of mineral adjuvants.

In some embodiments, the elastomeric portion may also contain a bulking agent. Suitable bulking agents may be water-soluble and include sweetening agents selected from, but not limited to, monosaccharides, disaccharides, polysaccharides, sugar alcohols, and mixtures thereof; randomly bonded glucose polymers such as those polymers distributed under the tradename Litesse™ which is the brand name for polydextrose and is manufactured by Danisco Sweeteners, Ltd. of 41-51 Brighton Road, Redhill, Surryey, RHI 6YS, United Kingdom; isomalt (a racemic mixture of alpha-D-glucopyranosyl-1,6-mannitol and alpha-D-glucopyranosyl-1,6-sorbitol manufactured under the tradename PALATINIT™ by Palatinit Sussungsmittel GmbH of Gotlieb-Daimler-Strause 12 a, 68165 Mannheim, Germany); maltodextrins; hydrogenated starch hydrolysates; hydrogenated hexoses; hydrogenated disaccharides; minerals, such as calcium carbonate, talc, titanium dioxide, dicalcium phosphate; celluloses; and mixtures thereof.

Suitable sugar bulking agents include monosaccharides, disaccharides and polysaccharides such as xylose, ribulose, glucose (dextrose), lactose, mannose, galactose, fructose (levulose), sucrose (sugar), maltose, invert sugar, partially hydrolyzed starch and corn syrup solids, and mixtures thereof.

Suitable sugar alcohol bulking agents include sorbitol, xylitol, mannitol, galactitol, lactitol, maltitol, erythritol, isomalt and mixtures thereof. Suitable hydrogenated starch hydrolysates include those disclosed in U.S. Pat. No. 4,279, 931 and various hydrogenated glucose syrups and/or powders which contain sorbitol, maltitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN®, a commercially available product manufactured by Roquette Freres of France, and HYSTAR®, a commercially available product manufactured by SPI Polyols, Inc. of New Castle, Del., are also useful.

The sweetening agents which may be included in the compositions of some embodiments may be any of a variety of sweeteners known in the art. These are described in more detail in the "Additional Components" section herein below and may be used in many distinct physical forms well-known in the art to provide an initial burst of sweetness and/or a prolonged sensation of sweetness. Without being limited thereto, such physical forms include free forms, such as spray dried, powdered, beaded forms, encapsulated forms, and mixtures thereof.

Desirably, the sweetener is a high intensity sweetener such as aspartame, neotame, sucralose, and acesulfame potassium (Ace-K).

In general, an effective amount of sweetener may be utilized to provide the level of sweetness desired, and this amount may vary with the sweetener selected. In some embodiments the amount of sweetener may be present in amounts from about 0.001% to about 3%, by weight of the confectionery composition, depending upon the sweetener or combination of sweeteners used. The exact range of amounts for each type of sweetener may be selected by those skilled in the art.

In some embodiments, particularly confectionery composition embodiments, the elastomeric portion may include a specific polyol composition including at least one polyol which is from about 30% to about 80% by weight of said elastomeric portion, and specifically from 50% to about 60%. In some confectionery composition embodiments, such elastomeric portion compositions may have low hygroscopicity. The polyol composition may include any polyol known in the art including, but not limited to maltitol, sorbitol, erythritol, xylitol, mannitol, isomalt, lactitol and combinations thereof. Lycasin™ which is a hydrogenated starch hydrolysate including sorbitol and maltitol, may also be used.

The amount of the polyol composition or combination of polyols used in the elastomeric portion will depend on many factors including the type of elastomers used in the elastomeric portion and the particular polyols used. For example, wherein the total amount of the polyol composition is in the range of about 40% to about 65% based on the weight of the elastomeric portion, the amount of isomalt may be from about 40% to about 60% in addition to an amount of sorbitol from about 0 up to about 10%, more specifically, an amount of isomalt may be from about 45% to about 55% in combination with sorbitol from about 5% to about 10% based on the weight of the elastomeric portion.

The polyol composition which may include one or more different polyols which may be derived from a genetically modified organism ("GMO") or GMO free source. For example, the maltitol may be GMO free maltitol or provided by a hydrogenated starch hydrolysate. For the purposes of this invention, the term "GMO-free" refers to a composition that has been derived from process in which genetically modified organisms are not utilized.

Coloring agents may be used in amounts effective to produce the desired color. The coloring agents may include pigments which may be incorporated in amounts up to about 6%, by weight of the confectionery composition. For example, titanium dioxide may be incorporated in amounts up to about 2%, and preferably less than about 1%, by weight of the confectionery composition. The colorants may also include natural food colors and dyes suitable for food, drug and cosmetic applications. These colorants are known as F.D.& C. dyes and lakes. The materials acceptable for the foregoing uses are preferably water-soluble. Illustrative non-limiting examples include the indigoid dye known as F.D.& C. Blue No. 2, which is the disodium salt of 5,5-indigotin-disulfonic acid. Similarly, the dye known as F.D.& C. Green No. 1 comprises a triphenylmethane dye and is the monosodium salt of 4-[4-(N-ethyl-p-sulfoniumbenzylamino)di-phenylmethylene]-[1-(N-ethyl-N-p-sulfoniumbenzyl)-delta-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857-884, which text is incorporated herein by reference. Additional coloring components are described in the "Additional Components" section hereinbelow.

Suitable oils and fats usable in confectionery compositions include partially hydrogenated vegetable or animal fats, such as coconut oil, palm kernel oil, beef tallow, and lard, among others. These ingredients when used are generally present in amounts up to about 7%, and preferably up to about 3.5%, by weight of the confectionery composition.

Some embodiments may include a method for preparing the improved compositions for the elastomeric portion, including elastomeric materials for both chewing gum and bubble gum compositions. The elastomeric portion compositions may be prepared using standard techniques and equipment known to those skilled in the art. The apparatus useful in accordance with some embodiments comprises mixing and heating apparatus well known in the confectionery manufacturing arts, and therefore the selection of the specific apparatus will be apparent to the artisan.

Texture Modification

In some embodiments, the texture of confectionery compositions are varied by varying the ratios and/or characteristics of the cooked saccharide and elastomeric portions, by changing processing parameters, or by including a texture modifying component.

When describing the texture profile of a confectionery composition, both analytical/instrumentation-based measures and sensory evaluation measures can be used. Analytical/instrumentation-based measures can include, but are not limited to, penetrometers, textureometers, tenderometers, universal testing machines, and the Texture Analyzer available from Stable MicroSystems of Surrey, United Kingdom. Sensory evaluation measures can include, but are not limited to, texture profiling and quantitative descriptive analysis. In some embodiments, the methods of measuring texture for a confectionery composition include a temporal component that measures the texture over time while the confectionery composition is being consumed. In other embodiments, the methods of measuring texture elucidate a change in the character of the texture over time. This change in the character of the texture over time can be used to define the texture transformation of the confectionery composition.

In some embodiments, varying the ratios and/or characteristics of the cooked saccharide and elastomeric portions can vary the texture of the finished confectionery composition. For example, a confectionery composition comprising 60% to 80% w/w of a cooked saccharide composition wherein the cooked saccharide composition is a hard boiled candy with less than 3% moisture will provide a harder initial texture similar to hard candy as compared to a confectionery composition comprising only 20% to 30% w/w of the same cooked saccharide composition. Alternatively, a confectionery composition comprising 40% to 50% w/w of a cooked saccharide composition wherein the cooked saccharide composition is a hard boiled candy with 2% moisture will provide a harder initial texture than a confectionery composition with the same amount (40%-50% w/w) of a hard boiled candy with 5% moisture. Similarly, a confectionery composition comprising 30% to 40% w/w of a cooked saccharide composition wherein the cooked saccharide composition is a hard boiled candy with 5% moisture will provide a harder initial texture than a confectionery composition with the same amount (40-50% w/w) of a chewy candy such as taffy wherein the taffy includes approximately 12% fat and about 8% moisture.

In some embodiments, varying the characteristics of the elastomeric portion can vary the texture of the confectionery composition. For example, an elastomeric portion including low melting point fats can provide a softer confectionery composition when combined with a cooked saccharide portion than an elastomeric portion including high melting point fats. Similarly, elastomeric portions containing lower levels of plasticizers and softeners may provide softer confectionery compositions when combined with cooked saccharide portions than elastomeric portions including higher levels of plasticizers and softeners.

In some embodiments, the texture of the confectionery composition and be varied by changing the characteristics of the confectionery composition. For example, the confectionery composition can include an outer layer or coating/shell. In some embodiments, the outer layer can be applied by pan coating techniques resulting in a crispy initial texture. In other embodiments, the confectionery composition can include a center-fill. The center-fill can be liquid, semi-solid, solid or gaseous. In some embodiments, a confectionery composition with a liquid center fill has a softer initial texture and requires less energy to bite through than a confectionery composition without a liquid center fill.

In some embodiments, the solid center can include particulates. Particulates can include, but are not limited to nuts; seeds; cocoa beans; coffee beans; milk powders; fruit-containing particles such as restructured fruit as described in U.S. Pat. No. 6,027,758; freeze dried fruit; freeze dried vegetables; fat particles; cocoa powder; sucrose; starch; polyols such as xylitol, erythritol, sorbitol, mannitol, maltitol, isomalt, hydrogenated starch hydrolysates; waxes; and combinations thereof.

In some embodiments, the solid center can include particles onto which other materials have been complexed. In some embodiments, the solid particle can include an absorbent material to which a second material is absorbed. In some embodiments, the solid particle can include an adsorbent material to which a second material is adsorbed. In some embodiments, the solid particle can include a complexation material to which a second material is complexed. In some embodiments, silica particles can absorb at least a second material to form a particulate solid interior portion. In some embodiments, cyclodextrin particles can complex with at least a second material to form a particulate solid interior portion.

In some embodiments where the solid center can change to a liquid, the solid center can include a mixture of invertase and sucrose such invertase operates on sucrose to form liquid invert sugar resulting in a liquid interior portion over time. In some embodiments, the center can be a fat with melting characteristics such that at manufacturing temperatures the fat is solid and then melts to become liquid at storage temperatures. In some embodiments, the solid center can include liquid-filled gelatin or sucrose beads that release liquid when ruptured or disrupted.

In some embodiments, the solid center can include a unitary or particulate solid confectionery composition. Such confectionery compositions can include, but are not limited to, chocolate, compound coating, carob coating, cocoa butter, butter fat, hydrogenated vegetable fat, illipe butter, fondant including fondant-based cremes, fudge, frappe, caramel, nougat, compressed tablet, candy floss (also known as cotton candy), marzipan, hard boiled candy, gummy candy, jelly beans, toffees, jellies including pectin-based gels, jams, preserves, butterscotch, nut brittles or croquant, candied fruit, marshmallow, pastilles, pralines or nougats, flour or starch confectionery, truffles, nonpareils, bon bons, after-dinner mints, fourres, nut pastes, peanut butter, chewing gum, kisses, angel kisses, montelimart, nougatine, fruit chews, Turkish delight, hard gums, soft gums, starch jellies, gelatin jellies, agar jellies, persipan, coconut paste, coconut ice, lozenges, cachous, crème paste, dragees, sugared nuts, sugared almonds, comfits, aniseed balls, licorice, licorice paste, chocolate spreads, chocolate crumb, and combinations thereof.

In some embodiments, the liquid center can be aqueous while in other embodiments the liquid center can be non-aqueous. In some embodiments, the liquid center can be a solution while in other embodiments, the center can be a suspension while in still other embodiments, the center can be an emulsion.

In some embodiments, the viscosity of the liquid center can be manipulated for a variety of reasons including, but not limited to, processing efficiency or creation of a desired perception. In some embodiments, the viscosity of the liquid center can be 3,000 to 10,000 pascal seconds. In some embodiments, the viscosity of the liquid center can be 4,000 to 6,5000 pascal seconds.

In some embodiments, the water activity of the liquid center can be manipulated for a variety of reasons including, but not limited to, microbial stability or maintenance of a desired texture. In some embodiments, the water activity of the liquid center can be 0.1 to 0.7. In some embodiments, the water activity of the liquid center can be 0.25 to 0.35.

Liquids that can be included in the liquid center can include, but are not limited to, fruit juice; vegetable juice; fruit puree; fruit pulp; vegetable pulp; vegetable puree; fruit sauce; vegetable sauce; honey; maple syrup; molasses; corn syrup; sugar syrup; polyol syrup; hydrogenated starch hydrolysates syrup; emulsions; vegetable oil; glycerin; propylene glycol; ethanol; liqueurs; chocolate syrup, dairy-based liquids such as milk, cream, etc.; and combinations thereof.

In some embodiments, a gaseous center can be formed by creating a hollow center. The gas can include a mixed composition gas such as air or it can include a single gas such as nitrogen, carbon dioxide, or oxygen. In some embodiments, a gaseous center will include gas trapped in a matrix such as a glassy candy matrix or foam. In some embodiments where gas can be trapped in a glassy candy matrix, the glass matrix can be sucrose and the gas can be carbon dioxide. In some embodiments where gas can be introduced into the center in a foam, the foam can include milk proteins and the gas can include a mixed composition gas such as air.

In some embodiments, varying processing parameters can result in confectionery products with different textures. In some embodiments, the confectionery composition is prepared by using an extruder to mix the components. For example, in FIG. 1, mixing operation 108 can include an extruder into which cooked saccharide syrup portion components, elastomeric portion components, and other ingredients can be fed and mixed together. Similarly, in FIGS. 2, 3, and 4, mixing operations 208, 314, and 414 respectively can include extruders. The extruders can be configured to input more or less energy into the confectionery composition. In some embodiments, a harder initial texture results from configuring the extruder to input less energy and provide gentle mixing. In other embodiments, the same composition can provide a softer initial texture by configuring the extruder to input more energy and provide vigorous mixing.

In some embodiments, a method for providing a desired texture includes determining a desired confectionery composition rheology (or a range of desired rheologies) and then determining rheologies for the cooked saccharide portion and the elastomeric portion. The desired confectionery composition rheology can be created by varying processing parameters of the extruder based on the rheologies of the portions.

Additional embodiments described herein relate to methods of developing confectionery products which provide a consumer-preferred texture. In accordance therewith, a consumer preference for a texture may first be identified. A variety of methods may be used to identify a consumer preference for a specific texture, such as, market research, including consumer surveys, taste panels, and the like. Once a consumer preference for a texture, such as, for example, a tougher chew that provides more salivation, is identified, a confectionery product tailored to satisfy that preference may be provided. In particular, any of the confectionery products described herein may be prepared. The confectionery product may be marketed to consumers based on the consumer-preferred texture.

The consumer-preferred texture provided by the confectionery product may be marketed to consumers in a variety of manners. Suitable marketing strategies, include, for example, print, radio, satellite radio, television, movie theater and online advertising campaigns, point-of-purchase advertisements, billboard advertisements, public transportation and telephone booth advertisements, indicia on the product packaging, including slogans, trademarks, terms and colors, instant messaging, ringtones, and the like.

In some embodiments, a texture modifying component is added to the confectionery composition. Inclusion of the texture modifying component can result in finished confectionery products with a variety of texture characteristics ranging from hard and friable to soft and pliable.

In some embodiments, a texture modifying component can include a particulate material. Suitable particulate materials can include, but are not limited to, sucrose, polyols such as sorbitol, xylitol, mannitol, galactitol, lactitol, maltitol, erythritol, isomalt, hydrogenated starch hydrolysates and mixtures thereof, starches, proteins, and combinations thereof. In some embodiments, the particulate material serving as a texture modifying component is selected based on its ability or lack of ability to crystallize the saccharides in the cooked saccharide portion. For example, when isomalt is included in the cooked saccharide portion, sorbitol powder can be added to the confectionery composition because it will not cause the isomalt to crystallize. Alternatively, when erythritol is included in the cooked saccharide portion, erythritol powder can be added to the confectionery composition because it will cause the erythritol to crystallize. Such particulates can be included in amounts from 5% to 35% w/w of the confectionery composition.

In some embodiments, a particulate texture modifying component can also include a flavoring component. For example, in embodiments where sorbitol is used as a texture modifying component, peppermint flavoring can be added to the sorbitol powder.

In some embodiments, a texture modifying component can include fats, oils, or other hydrophobic materials. Suitable fats can include, but are not limited to, partially hydrogenated vegetable or animal fats, such as coconut oil, corn oil, palm kernel oil, peanut oil, soy bean oil, sesame oil, cottonseed oil, cocoa butter, milk fat, beef tallow, and lard, among others. Suitable hydrophobic materials include chocolate, chocolate crumb, carob coatings, and compound coatings. Such fats, oils, and/or hydrophobic materials can be included in amounts of 1% to 10% w/w of the confectionery composition.

In some embodiments, the sensory perception of the texture modifying component is similar to that of fat, oil, or other hydrophobic materials even though the texture modifying component is present in the confectionery composition at a lower level. For example, a confectionery composition including 2.5% hydrogenated cottonseed oil can provide the same mouthfeel perception as a confection including 10%-50% fat as measured by sensory evaluation techniques.

In some embodiments, a texture modifying component is incorporated into the confectionery composition when the cooked saccharide composition is being mixed with the elastomeric composition.

Appearance

In some embodiments, a confectionery composition including a cooked saccharide portion and an elastomeric portion provides a desired appearance. For example, in some embodiments, an exterior surface of a confectionery composition provides a desired level or shine or gloss. Appearance aspects of shine and gloss can be measured by a variety of methods such as optometric methods including, but not limited to, reflectance meters, spectophotometers, and consumer testing.

In some embodiments, a confectionery composition can be configured to include a cooked saccharide portion and an elastomeric portion that have been adjusted to be visually different.

Additional Components

Additional additives, such as physiological cooling agents, throat-soothing agents, spices, warming agents, tooth-whitening agents, breath-freshening agents, vitamins, nutraceuticals, phytochemicals, polyphenols, antioxidants, minerals, caffeine, drugs and other actives may also be included in any or all portions of the confectionery composition. Such components may be used in amounts sufficient to achieve their intended effects.

Any of the additional components discussed herein may be added to any portion of the confectionery composition in their modified release form and/or without modified release (sometimes referred to as "free" components). In some embodiments, for example, a single component may be added to the confectionery composition in its modified release form and free form. The modified release component and free component may be included together in the same portion of the confectionery composition or, in some embodiments, the two components may be included in different portions of the confectionery composition.

In some other embodiments, for example, two different components that provide the same functionality, e.g., two different flavors, sweeteners, tastes, sensations, or the like, may be included in a confectionery composition. In some embodiments, both components may have modified release properties. Alternatively, in some embodiments, one of the components may be modified release, whereas the other component may be free. The two components may be included in the same or different portions of the confectionery composition.

Types of individual ingredients for which optional managed release from a confectionery composition may be desired, include, but are not limited to sweeteners, flavors, actives, effervescing ingredients, appetite suppressors, breath fresheners, dental care ingredients, emulsifiers, flavor potentiators, bitterness masking or blocking ingredients, food acids, micronutrients, sensates, mouth moistening ingredients, throat care ingredients, colors, and combinations thereof. Ingredients may be available in different forms such as, for example, liquid form, spray-dried form, or crystalline form. In some embodiments, a delivery system or confectionery composition may include the same type of ingredient in different forms. For example, a confectionery composition may include a liquid flavor and a spray-dried version of the same flavor. In some embodiments, the ingredient may be in its free or encapsulated form and may be present in any portion of the confectionery composition such as in the cooked saccharide portion, the elastomeric portion, or the coating or center-fill.

In some embodiments, an ingredient's release is modified such that when a consumer chews the confectionery composition, they may experience an increase in the duration of flavor or sweetness perception and/or the ingredient is released or otherwise made available over a longer period of time. Modified release may be accomplished by any method known in the art, such as by encapsulation. Where modified release is due to encapsulation, this may be accomplished by a variety of means such as by spray coating or extrusion.

Additionally, if early and extended release of the ingredient is desired, the confectionery composition may include ingredients without modified release (sometimes referred to as "free" ingredients), as well as ingredients with modified release. In some embodiments, a free ingredient may be used to deliver an initial amount or "hit" of an ingredient (e.g., flavor, cooling agent) or an initial sensation or benefit caused by the ingredient (e.g., flavor, nasal action, cooling, warming, tingling, saliva generation, breath freshening, teeth whitening, throat soothing, mouth moistening, etc.). In some embodiments, the same ingredient can be provided with modified release characteristics to provide an additional or delayed amount of the same sensation or benefit. By using both the free ingredient and the ingredient with modified release characteristics, the sensation or benefit due to the ingredient may be provided over a longer period of time and/or perception of the sensation or benefit by a consumer may be improved. Also, in some embodiments the initial amount or "hit" of the ingredient may predispose or precondition the consumers' mouth or perception of the confectionery composition.

In some embodiments, modified release can also be affected by where (what portion of the confectionery composition) the ingredient is included. For example, an ingredient that has an affinity for elastomeric materials, can be included in the cooked saccharide portion where it does not have an affinity and thus it will be released faster and more completely. Similarly, in some embodiments, it may be desirable to release an ingredient over time or less completely. In that case, including the ingredient with an affinity for elastomeric materials in the elastomeric portion will provide the desired release.

As another example, in some embodiments it may be desirable to provide a sustained release of an ingredient in a confectionery composition over time. To accomplish sustained release, the ingredient may be modified to allow for a lower concentration of the ingredient to be released over a longer period of time versus the release of a higher concentration of the ingredient over a shorter period of time. A sustained release of an ingredient may be advantageous in situations when the ingredient has a bitter or other bad taste at the higher concentrations. A sustained release of an ingredient also may be advantageous when release of the ingredient in higher concentrations over a shorter period of time may result in a lesser amount of the ingredient being optimally delivered to the consumer. For example, for a tooth whitening or breath freshening ingredient, providing too much of the ingredient too fast may result in a consumer swallowing a significant portion of the ingredient before the ingredient has had a chance to interact with the consumer's teeth, mucous membranes, and/or dental work, thereby wasting the ingredient or at least reducing the benefit of having the ingredient in the confectionery composition.

In some embodiments described herein, the elastomeric portion of the confectionery composition may include at least one modified release component. At least one modified release component optionally may be added to the cooked saccharide portion, the center-fill and/or coating, as well.

The additional modified release component that may be included in the cooked saccharide portion, center-fill and/or coating may be the same as or different from the modified release component contained in the elastomeric portion.

Ingredient Release Management

In different embodiments, different techniques, ingredients, and/or delivery systems, may be used to manage release of one or more ingredients in a confectionery composition. In some embodiments, more than one of the techniques, ingredients, and/or delivery systems may be used.

In some embodiments, the delay in availability or other release of an ingredient in a confectionery composition caused by encapsulation of the ingredient may be based, in whole or in part, by one or more of the following: the type of encapsulating material, the molecular weight of the encapsulating material, the tensile strength of the delivery system containing the ingredient, the hydrophobicity of the encapsulating material, the presence of other materials in the cooked saccharide portion or elastomeric portion (e.g., tensile strength modifying agents, emulsifiers), presence and/or composition of the texture modifying component, the ratio of the amounts of one or more ingredients in the delivery system to the amount of the encapsulating material in the delivery system, the number of layers of encapsulating material, the desired texture, flavor, shelf life, or other characteristic of a confectionery composition, the ratio of the encapsulating material to the ingredient being encapsulated, etc. Thus, by changing or managing one or more of these characteristics of a delivery system or the confectionery composition, release of one or more ingredients in a confectionery composition during consumption of the confectionery composition can be managed more effectively and/or a more desirable release profile for one or more ingredients in the delivery system or the confectionery composition may be obtained. This may lead to a more positive sensory or consumer experience during consumption of the confectionery composition, more effective release of such one or more ingredients during consumption of the confectionery composition, less need for the ingredient (e.g., more effective release of the ingredient may allow the amount of the ingredient in the confectionery composition to be reduced), increased delivery of a therapeutic or other functional benefit to the consumer, etc. Additionally, in some embodiments, managing the release rate or profile can be tailored to specific consumer segments.

Encapsulation

In some embodiments, one or more ingredients may be encapsulated with an encapsulating material to modify the release profile of the ingredient. In general, partially or completely encapsulating an ingredient used in a confectionery composition with an encapsulating material may delay release of the ingredient during consumption of the confectionery composition, thereby delaying when the ingredient becomes available inside the consumer's mouth, throat, and/or stomach, available to react or mix with another ingredient, and/or available to provide some sensory experience and/or functional or therapeutic benefit. This can be particularly true when the ingredient is water soluble or at least partially water soluble.

In some embodiments, encapsulation may be employed to provide barrier protection to or from a component rather than to modify the release of the component. For example, it often is desirable to limit the exposure of acids to other components in a confectionery composition. Such acids may be encapsulated to limit their exposure to other components, or alternatively, the other components in the confectionery composition may be encapsulated to limit their exposure to the acid.

In some embodiments, a material used to encapsulate an ingredient may include water insoluble polymers, co-polymers, or other materials capable of forming a strong matrix, solid coating, or film as a protective barrier with or for the ingredient. In some embodiments, the encapsulating material may completely surround, coat, cover, or enclose an ingredient. In other embodiments, the encapsulating material may only partially surround, coat, cover, or enclose an ingredient. Different encapsulating materials may provide different release rates or release profiles for the encapsulated ingredient. In some embodiments, encapsulating material used in a delivery system may include one or more of the following: polyvinyl acetate, polyethylene, crosslinked polyvinyl pyrrolidone, polymethylmethacrylate, polylactidacid, polyhydroxyalkanoates, ethylcellulose, polyvinyl acetatephthalate, polyethylene glycol esters, methacrylicacid-co-methylmethacrylate, ethylene-vinylacetate (EVA) copolymer, and the like, and combinations thereof.

In some embodiments, an ingredient may be pre-treated prior to encapsulation with an encapsulating material. For example, an ingredient may be coated with a "coating material" that is not miscible with the ingredient or is at least less miscible with the ingredient relative to the ingredient's miscibility with the encapsulating material.

In some embodiments, an ingredient may be encapsulated with multiple encapsulating materials. For example, an ingredient may be coated with an encapsulating ingredient that contains polyvinyl acetate and may then be coated with an encapsulating ingredient that contains wax. In some embodiments, such multiple encapsulation systems can provide thermal stability protection for ingredients that would be adversely affected by the heat used in confectionery making processes.

In some embodiments, an encapsulation material may be used to individually encapsulate different ingredients in the same confectionery composition. For example, a delivery system may include aspartame encapsulated by polyvinyl acetate. Another delivery system may include acesulfame-K encapsulated by polyvinyl acetate. Both delivery systems may be used as ingredients in the same confectionery composition or in other confectionery compositions. For additional examples, see U.S. Patent Application Ser. No. 60/683,634 entitled "Methods and Delivery Systems for Managing Release of One or More Ingredients in an Edible Composition" and filed May 23, 2005, the entire contents of which are incorporated herein by reference for all purposes.

In some embodiments, different encapsulation materials may be used to individually encapsulate different ingredients used in the same confectionery composition. For example, a delivery system may include aspartame encapsulated by polyvinyl acetate. Another delivery system may include acesulfame-K encapsulated by EVA. Both delivery systems may be used as ingredients in the same confectionery composition or other confectionery compositions. Examples of encapsulated ingredients using different encapsulating materials can be found in U.S. Patent Application Ser. No. 60/655,894 filed Feb. 25, 2005, and entitled "Process for Manufacturing a Delivery System for Active Components as Part of an Edible Composition," the entire contents of which are incorporated herein by reference for all purposes.

Methods of Encapsulation

There are many ways to encapsulate one or more ingredients with an encapsulating material. For example, in some embodiments, a sigma blade or Banbury™ type mixer may be used. In other embodiments, an extruder or other type of continuous mixer may be used. In some embodiments, spray coating, spray chilling, absorption, adsorption, inclusion complexing (e.g., creating a flavor/cyclodextrin complex), coacervation, fluidized bed coating, or other process may be used to encapsulate an ingredient with an encapsulating material.

Examples of encapsulation of ingredients can be found in U.S. Patent Application Ser. No. 60/655,894, filed Feb. 25, 2005, and entitled "Process for Manufacturing a Delivery System for Active Components as Part of an Edible Composition," the entire contents of which are incorporated herein by reference for all purposes. Other examples of encapsulation of ingredients can be found in U.S. patent application Ser. No. 10/955,255 filed Sep. 30, 2004, and entitled "Encapsulated Compositions and Methods of Preparation," the entire contents of which are incorporated herein by reference for all purposes. Further examples of encapsulation of ingredients can be found in U.S. patent application Ser. No. 10/955,149 filed Sep. 30, 2004, and entitled "Thermally Stable High Tensile Strength Encapsulation Compositions for Actives," the entire contents of which are incorporated herein by reference for all purposes. Still further examples of encapsulation of ingredients can be found in U.S. patent application Ser. No. 11/052,672 filed Feb. 7, 2005, and entitled "Stable Tooth Whitening Confectionery with Reactive Components," the entire contents of which are incorporated herein by reference for all purposes. Further encapsulation techniques and resulting delivery systems may be found in U.S. Pat. Nos. 6,770,308, 6,759,066, 6,692,778, 6,592,912, 6,586,023, 6,555,145, 6,479,071, 6,472,000, 6,444,241, 6,365,209, 6,174,514, 5,693,334, 4,711,784, 4,816,265, and 4,384,004, the contents of all of which are incorporated herein by reference for all purposes.

In some embodiments, a delivery system may be ground to a powdered material with a particular size for use as an ingredient in a confectionery composition. For example, in some embodiments, an ingredient may be ground to approximately the same particle size of the other confectionery composition ingredients so as to create a homogeneous mixture. In some embodiments, the delivery system may be ground to a powdered material with an average particle size such as, for example, about 4 to about 100 mesh or about 8 to about 25 mesh or about 12 to about 20 mesh.

Tensile Strength

In some embodiments, selection of an encapsulating material for one or more ingredients may be based on tensile strength desired for the resulting delivery system. For example, in some embodiments, a delivery system produces delayed or otherwise controlled release of an ingredient through the use of a pre-selected or otherwise desired tensile strength.

In some embodiments, increasing the tensile strength of a delivery system may increase the delayed or extended release of an ingredient in the delivery system. The tensile strength for a delivery system may be matched with a desirable release rate selected according to the type of the ingredient(s) to be encapsulated for the delivery system, the encapsulating material used, any other additives incorporated in the delivery system and/or a confectionery composition using the delivery system as an ingredient, the desired rate of release of the ingredient, and the like. In some embodiments, the tensile strength of a delivery system which can be at least 6,500 psi, including 7500, 10,000, 20,000, 30,000, 40,000, 50,000, 60,000, 70,000, 80,000, 90,000, 100,000, 125,000, 135,000, 150,000, 165,000, 175, 000, 180,000, 195,000, 200,000 and all ranges and subranges there between, for example, a tensile strength range of 6,500 to 200,000 psi.

In some embodiments, a delivery system for one or more ingredients can be provided based on the tensile strength of the delivery system having a specific tensile strength when compared to a standard. Thus, the design of the delivery system is not focused on one characteristic (e.g., molecular weight) of one of the materials (e.g., encapsulating material) used to produce the delivery system. In this manner, a delivery system can be formulated to express a desired release profile by adjusting and modifying the tensile strength through the specific selection of the ingredient(s), encapsulating material, additives, amount of the ingredient(s), amount of encapsulating material, relative amounts of ingredient(s) to encapsulating material, etc. If a desired tensile strength is chosen for a delivery system, any delivery system that has the desired tensile strength may be used without being limited to a particular encapsulating material and its molecular weight. The formulation process can be extended to encapsulating materials that exhibit similar physical and chemical properties as the encapsulating material forming part of the standard delivery system.

In some embodiments, a delivery system for delivering an ingredient may be formulated to ensure an effective sustained release of the ingredient based on the type and amount of the ingredient and the desired release rate for the ingredient. For example, it may be desirable to affect the controlled release of a high intensity sweetener from a confectionery composition over a period of twenty-five to thirty minutes to ensure against a rapid burst of sweetness that may be offensive to some consumers. A shorter controlled release time may be desirable for other type of ingredients such as pharmaceuticals or therapeutic agents, which may be incorporated into the same confectionery composition by using separate delivery systems for each of these ingredients. Delivery systems may be formulated with a particular tensile strength associated with a range of release rates based on a standard. The standard may comprise a series of known delivery systems having tensile strengths over a range extending, for example, from low to high tensile strength values. Each of the delivery systems of the standard will be associated with a particular release rate or ranges of release rates. Thus, for example, a delivery system can be formulated with a relatively slow release rate by a fabricating a delivering system having a relatively high tensile strength. Conversely, lower tensile strength compositions tend to exhibit relatively faster release rates.

In some embodiments, encapsulating material in a delivery system may be present in amounts of from about 0.2% to 10% by weight based on the total weight of the chewing confectionery composition, including 0.3, 0.5, 0.7, 0.9, 1.0, 1.25, 1.4, 1.7, 1.9, 2.2, 2.45, 2.75, 3.0, 3.5, 4.0, 4.25, 4.8, 5.0, 5.5, 6.0, 6.5, 7.0, 7.25, 7.75, 8.0, 8.3, 8.7, 9.0, 9.25, 9.5, 9.8 and all values and ranges there between, for example, from 1% to 5% by weight. The amount of the encapsulating material can depend in part on the amount of the ingredient(s) component that is encapsulated. The amount of the encapsulating material with respect to the weight of the delivery system, is from about 30% to 99%, including 35, 40, 45, 50, 55, 60, 65, 70, 75, 80, 85, 95, 97 and all values and ranges there between, for example, from about 60% to 90% by weight.

In some embodiments, the tensile strength of a delivery system may be selected from relatively high tensile strengths when a relatively slow rate of release for an ingredient in the delivery system is desired and relatively lower tensile strengths when a faster rate of release for an ingredient in the delivery system is desired. Thus, when employing a tensile strength of 50,000 psi for a delivery system, the release rate of the ingredient, will generally be lower than the release rate of the ingredient in a delivery system having a tensile strength of 10,000 psi regardless of the type of encapsulating material (e.g., polyvinyl acetate) chosen.

In some embodiments, the encapsulating material for a delivery system is polyvinyl acetate. A representative example of a polyvinyl acetate product suitable for use as an encapsulating material in the present invention is Vinnapas® B100 sold by Wacker Polymer Systems of Adrian, Mich. A delivery system utilizing polyvinyl acetate may be prepared by melting a sufficient amount of polyvinyl acetate at a temperature of about 65° C. to 120° C. for a short period of time, e.g., five minutes. The melt temperature will depend on the type and tensile strength of the polyvinyl acetate encapsulating material where higher tensile strength materials will generally melt at higher temperatures. Once the encapsulating material is melted, a suitable amount of an ingredient (e.g., high intensity sweetener such as aspartame) is added and blended into the molten mass thoroughly for an additional short period of mixing. The resulting mixture is a semi-solid mass, which is then cooled (e.g., at 0° C.) to obtain a solid, and then ground to a U.S. Standard sieve size of from about 30 to 200 (600 to 75 microns). The tensile strength of the resulting delivery system can readily be tested according to ASTM-D638.

For additional information regarding how tensile strength of a delivery system may be used to create managed release of one or more ingredients, see U.S. patent application Ser. No. 11/083,968 entitled "A Delivery System for Active Components as Part of an Edible Composition Having Preselected Tensile Strength" and filed on Mar. 21, 2005, and U.S. patent application Ser. No. 10/719,298 entitled "A Delivery System for Active Components as Part of an Edible Composition" and filed Nov. 21, 2003, the complete contents of both of which are incorporated herein by reference for all purposes.

Hydrophobicity

In some embodiments, the release of one or more ingredients from a delivery system may depend on more than tensile strength. For example, the release of the ingredients may be directly related to the tensile strength of the delivery system and the hydrophobicity (i.e., water resistance) of the encapsulating polymer or other material.

As a more specific example, when a delivery system is used in a confectionery composition, moisture may be absorbed in the encapsulated ingredient(s) during mastication and chewing of the confectionery composition. This may result in softening of the encapsulating material and releasing of the ingredient(s) during the mastication and chewing of the confectionery composition. The softening of the encapsulation material depends on the hydrophobicity of the polymer used as the encapsulation material. In general, the higher the hydrophobicity of the polymer, the longer mastication time is needed for softening the polymer.

As one example, higher hydrophobic polymers such as ethylene-vinylacetate (EVA) copolymer can be used to increase or otherwise manage ingredient (e.g., sweetener) release times from encapsulations. The degree of hydrophobicity can be controlled by adjusting the ratio of ethylene and vinylacetate in the copolymer. In general, the higher the ethylene to vinylacetate ratio, the longer time it will take during consumption to soften the encapsulation particles, and the slower or more delayed will be the release rate of the ingredient. The lower the ethylene to vinylacetate ratio, the shorter time it will take during consumption to soften the encapsulation particles, and the faster or earlier will be the release rate of the ingredient.

As illustrated by the discussion above, in some embodiments, release of an ingredient from a delivery system can be managed or otherwise controlled by formulating the delivery system based on the hydrophobicity of the encapsulating material, e.g., the polymer, for the ingredient. Using highly hydrophobic polymers, the release times of the ingredient can be increased or delayed. In a similar manner, using encapsulating material that is less hydrophobic, the ingredient can be released more rapidly or earlier.

The hydrophobicity of a polymer can be quantified by the relative water-absorption measured according to ASTM D570-98. Thus, by selecting encapsulating material(s) for a delivery system with relatively lower water-absorption properties and adding that to a mixer, the release of the ingredient contained in the produced delivery system can be delayed compared to those encapsulating materials having higher water-absorption properties.

In some embodiments, polymers with water absorption of from about 50 to 100% (as measured according to ASTM D570-98) can be used. Moreover, to decrease the relative delivery rate, the encapsulating material can be selected such that the water absorption would be from about 15% to about 50% (as measured according to ASTM D570-98). Still further, in other embodiments, the water absorption properties of the encapsulating material can be selected to be from 0.0% to about 5% or up to about 15% (as measured according to ASTM D570-98). In other embodiments, mixtures of two or more delivery systems formulated with encapsulating material having different water-absorption properties can also be used in subsequent incorporation into a confectionery composition.

Polymers with suitable hydrophobicity which may be used for delivery systems include homo- and co-polymers of, for example, vinyl acetate, vinyl alcohol, ethylene, acrylic acid, methacrylate, methacrylic acid and others. Suitable hydrophobic copolymers include the following non-limiting examples, vinyl acetate/vinyl alcohol copolymer, ethylene/vinyl alcohol copolymer, ethylene/acrylic acid copolymer, ethylene/methacrylate copolymer, ethylene/methacrylic acid copolymer.

In some examples, the hydrophobic encapsulating material in a delivery system may be present in amounts of from about 0.2% to 10% by weight based on the total weight of a confectionery composition containing the delivery system, including 0.3, 0.5, 0.7, 0.9, 1.0, 1.25, 1.4, 1.7, 1.9, 2.2, 2.45, 2.75, 3.0, 3.5, 4.0, 4.25, 4.8, 5.0, 5.5, 6.0, 6.5, 7.0, 7.25, 7.75, 8.0, 8.3, 8.7, 9.0, 9.25, 9.5, 9.8 and all values and ranges there between, for example, from 1% to 5% by weight. The amount of the encapsulating material will, of course, depend in part on the amount of the ingredient that is encapsulated. The amount of the encapsulating material with respect to the weight of the delivery system, is from about 30% to 99%, including 35, 40, 45, 50, 55, 60, 65, 70, 75, 80, 85, 95, 97 and all values and ranges there between, for example, from about 60% to 90% by weight.

In formulating the delivery system based on the selection criteria of hydrophobicity of the encapsulating material, the encapsulated ingredient can be entirely encapsulated within the encapsulating material or incompletely encapsulated within the encapsulating material provided the resulting delivery system meets the criteria set forth hereinabove. The incomplete encapsulation can be accomplished by modifying and/or adjusting the manufacturing process to create partial coverage of the ingredient.

For example, if ethylene-vinyl acetate is the encapsulating material for an ingredient, the degree of hydrophobicity can be controlled by adjusting the ratio of ethylene and vinyl acetate in the copolymer. The higher the ethylene to vinylacetate ratio, the slower the release of the ingredient. Using vinylacetate/ethylene copolymer as an example, the ratio of the vinylacetate/ethylene in the copolymer can be from about 1 to about 60%, including ratios of 2.5, 5, 7.5, 9, 12, 18, 23, 25, 28, 30, 35, 42, 47, 52, 55, 58.5% and all values and ranges there between.

In some embodiments, a method of selecting a target delivery system containing an ingredient for a confectionery composition is based on the hydrophobicity of the encapsulating material for the ingredient in the delivery system. The method generally includes preparing a targeted delivery system containing an ingredient to be encapsulated, an encapsulating material and optional additives, with the encapsulating material having a pre-selected or otherwise desired hydrophobicity. The hydrophobicity of the encapsulating material employed in the targeted delivery system can be selected to provide a desirable release rate of the ingredient. This selection of the encapsulating material is based on the hydrophobicity of sample delivery systems having the same or similar ingredient and known release rates of the ingredient. In another embodiment of the invention, the method comprises (a) obtaining a plurality of sample delivery systems comprising at least one ingredient, at least one encapsulating material, and optional additives, wherein each of the delivery systems is prepared with different encapsulating materials having different hydrophobicities; (b) testing the sample delivery systems to determine the respective release rates of the ingredient(s); and (c) formulating a target delivery system containing the same ingredient(s) with a hydrophobic encapsulating material corresponding to a desired release rate of the ingredient(s) based on the obtained sample delivery systems.

The method of selecting at least one delivery system suitable for incorporation into a confectionery composition preferably can begin by determining a desired release rate for an ingredient (i.e., a first active component). The determination of the desired release rate may be from known literature or technical references or by in vitro or in vivo testing. Once the desired release rate is determined, the desired hydrophobicity of the encapsulating material can be determined (i.e., a first hydrophobic encapsulating material) for a delivery system (i.e., first delivery system) that can release the first active component at the desired release. Once the delivery system is obtained which can deliver the first active component as required it is then selected for eventual inclusion in a confectionery composition.

The method described above may then be repeated for a second active component and for additional active components as described via the determination and selection of a suitable delivery system.

For additional information regarding the relationship of hydrophobicity of an encapsulating material to the release of an ingredient from a delivery system, see U.S. Patent Application Ser. No. 60/683,634 entitled "Methods and Delivery Systems for Managing Release of One or More Ingredients in an Edible Composition" and filed on May 23, 2005, with the U.S. Patent and Trademark Office, the complete contents of which are incorporated herein by reference for all purposes.

Ratio of Ingredient to Encapsulating Material for Ingredient in Delivery System

In general, the "loading" of an ingredient in a delivery system can impact the release profile of the ingredient when the ingredient is used in a confectionery composition. Loading refers to the amount of one or more ingredients contained in the delivery system relative to the amount of encapsulating material. More specifically, the ratio of the amount of one or more ingredients in a delivery system to the amount of encapsulating material in the delivery system can impact the release rate of the one or more ingredients. For example, the lower the ratio or loading of the amount of one or more ingredients in a delivery system to the amount of encapsulating material in the delivery system, the longer or more delayed will be the release of the one or more ingredients from the delivery system. The higher the ratio or loading of the amount of one or more ingredients in a delivery system to the amount of encapsulating material in the delivery system, the faster or earlier will be the release of the one or more ingredients from the delivery system. This principle can be further employed to manage the release profiles of the one or more ingredients by using higher loading of ingredients designed to be released early in combination with lower loading of ingredients designed to be released later. In some embodiments, the one or more ingredients can be the same or different.

For additional information regarding the relationship of the ratio of the amount ingredient in a delivery system to the amount of encapsulating material in the delivery system to the release of an ingredient from a delivery system, see U.S. patent application Ser. No. 11/134,371 entitled "A Delivery System For Active Components as Part of and Edible Composition Including a Ratio of Encapsulating Material and Active Component" and filed on May 23, 2005, with the U.S. Patent and Trademark Office, the complete contents of which are incorporated herein by reference for all purposes.

There are many types of ingredients for which managed release of the ingredients from a confectionery composition may be desired. In addition, there are many groups of two or more ingredients for which managed release of the group of ingredients from a confectionery composition may be desired.

Flavorants

In some embodiments, flavorants may include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, yazu, sudachi, and fruit essences including apple, pear, peach, grape, blueberry, strawberry, raspberry, cherry, plum, pineapple, apricot, banana, melon, apricot, ume, cherry, raspberry, blackberry, tropical fruit, mango, mangosteen, pomegranate, papaya and so forth. Other potential flavors whose release profiles can be managed include a milk flavor, a butter flavor, a cheese flavor, a cream flavor, and a yoghurt flavor; a vanilla flavor; tea or coffee flavors, such as a green tea flavor, a oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an angelica flavor, a fennel flavor, an allspice flavor, a cinnamon flavor, a camomile flavor, a mustard flavor, a cardamom flavor, a caraway flavor, a cumin flavor, a clove flavor, a pepper flavor, a coriander flavor, a sassafras flavor, a savory flavor, a Zanthoxyli Fructus flavor, a perilla flavor, a juniper berry flavor, a ginger flavor, a star anise flavor, a horseradish flavor, a thyme flavor, a tarragon flavor, a dill flavor, a capsicum flavor, a nutmeg flavor, a basil flavor, a marjoram flavor, a rosemary flavor, a bayleaf flavor, and a wasabi (Japanese horseradish) flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture. Flavors may also provide breath freshening properties, particularly the mint flavors when used in combination with the cooling agents, described herein below.

In some embodiments, other flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used. This publication is incorporated herein by reference. These may include natural as well as synthetic flavors.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, .e., melonal (melon), 2,6-dimethyloctanal (green fruit), and 2-dodecenal (citrus, mandarin), cherry, grape, blueberry, blackberry, strawberry shortcake, and mixtures thereof.

In some embodiments, flavoring agents are used at levels that provide a perceptible sensory experience i.e. at or above their threshold levels. In other embodiments, flavoring agents are used at levels below their threshold levels such that they do not provide an independent perceptible sensory experience. At subthreshold levels, the flavoring agents may provide an ancillary benefit such as flavor enhancement or potentiation.

In some embodiments, a flavoring agent may be employed in either liquid form and/or dried form. When employed in the latter form, suitable drying means such as spray drying the liquid may be used. Alternatively, the flavoring agent may be absorbed onto water soluble materials, such as cellulose, starch, sugar, maltodextrin, gum arabic and so forth or may be encapsulated. In still other embodiments, the flavoring agent may be adsorbed onto silicas, zeolites, and the like.

In some embodiments, the flavoring agents may be used in many distinct physical forms. Without being limited thereto, such physical forms include free forms, such as spray dried, powdered, beaded forms, encapsulated forms, and mixtures thereof.

Illustrations of the encapsulation of flavors as well as other additional components can be found in the examples provided herein. Typically, encapsulation of a component will result in a delay in the release of the predominant amount of the component during consumption of a confectionery composition that includes the encapsulated component (e.g., as part of a delivery system added as an ingredient to the chewing confectionery composition). In some embodiments, the release profile of the ingredient (e.g., the flavor, sweetener, etc.) can be managed by managing various characteristics of the ingredient, delivery system containing the ingredient, and/or the confectionery composition containing the delivery system and/or how the delivery system is made. For example, characteristics might include one or more of the following: tensile strength of the delivery system, water solubility of the ingredient, water solubility of the encapsulating material, water solubility of the delivery system, ratio of ingredient to encapsulating material in the delivery system, average or maximum particle size of ingredient, average or maximum particle size of ground delivery system, the amount of the ingredient or the delivery system in the confectionery composition, ratio of different polymers used to encapsulate one or more ingredients, hydrophobicity of one or more polymers used to encapsulate one or more ingredients, hydrophobicity of the delivery system, the type or amount of coating on the delivery system, the type or amount of coating on an ingredient prior to the ingredient being encapsulated, etc.

Sweetening Ingredients

The sweeteners involved may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as dihydrochalcones, monellin, steviosides, lo han quo, lo han quo derivatives, glycyrrhizin, dihydroflavenol, and sugar alcohols such as sorbitol, mannitol, maltitol, xylitol, erythritol, and L-aminodicarboxylic acid aminoalkenoic acid ester amides, such as those disclosed in U.S. Pat. No. 4,619,834, which disclosure is incorporated herein by reference, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and mixtures thereof;

(c) dipeptide based sweeteners, such as L-aspartic acid derived sweeteners, such as L-aspartyl-L-phenylalanine methyl ester (Aspartame), N—[N-(3,3-dimethylbutyl)-L-α-aspartyl]-L-phenylalanine 1-methyl ester (Neotame), and materials described in U.S. Pat. No. 3,492,131, L-alphaaspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and mixtures thereof;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructo-f uranoside, or 4,1'-dichloro-4,1'-dideoxygalactosucrose; 1',6'-dichloro1,6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideoxy-beta-D-fructofuranoside, or 4,6,1',6'-tetrachloro-4,6,1',6'-tetradeoxygalacto-sucrose; and 4,6,1',6'-tetradeoxy-sucrose, and mixtures thereof;

(e) protein based sweeteners such as thaumaoccous danielli (Thaumatin I and II) and talin; and (f) the sweetener monatin (2-hydroxy-2-(indol-3-ylmethyl)-4-aminoglutaric acid) and its derivatives.

The intense sweetening agents may be used in many distinct physical forms well-known in the art to provide an initial burst of sweetness and/or a prolonged sensation of sweetness. Without being limited thereto, such physical forms include free forms, spray dried forms, powdered forms, beaded forms, encapsulated forms, and mixtures thereof. In one embodiment, the sweetener is a high intensity sweetener such as aspartame, sucralose, and acesulfame potassium (e.g., Ace-K or acesulfame-K).

In some embodiments, the sweetener may be a polyol. Polyols can include, but are not limited to glycerol, sorbitol, maltitol, maltitol syrup, mannitol, isomalt, erythritol, xylitol, hydrogenated starch hydrolysates, polyglycitol syrups, polyglycitol powders, lactitol, and combinations thereof.

The active component (e.g., sweetener), which is part of the delivery system, may be used in amounts necessary to impart the desired effect associated with use of the active component (e.g., sweetness). In general, an effective amount of intense sweetener may be utilized to provide the level of sweetness desired, and this amount may vary with the sweetener selected. The intense sweetener may be present in amounts from about 0.001% to about 3%, by weight of the composition, depending upon the sweetener or combination of sweeteners used. The exact range of amounts for each type of sweetener may be selected by those skilled in the art.

Sensate Ingredients

Sensate compounds can include cooling agents, warming agents, tingling agents, effervescent agents, and combinations thereof. A variety of well known cooling agents may be employed. For example, among the useful cooling agents are included xylitol, erythritol, dextrose, sorbitol, menthane, menthone, ketals, menthone ketals, menthone glycerol ketals, substituted p-menthanes, acyclic carboxamides, mono menthyl glutarate, substituted cyclohexanamides, substituted cyclohexane carboxamides, substituted ureas and sulfonamides, substituted menthanols, hydroxymethyl and hydroxymethyl derivatives of p-menthane, 2-mercapto-cyclo-decanone, hydroxycarboxylic acids with 2-6 carbon atoms, cyclohexanamides, menthyl acetate, menthyl salicylate, N,2,3-trimethyl-2-isopropyl butanamide (WS-23), N-ethyl-p-menthane-3-carboxamide (WS-3), isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methyl-cyclohexanecarboxamide, Japanese mint oil, peppermint oil, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, n-ethyl-t-2-c-6 nonadienamide, N,N-dimethyl menthyl succinamide, substituted p-menthanes, substituted p-menthane-carboxamides, 2-isopropanyl-5-methylcyclohexanol (from Hisamitsu Pharmaceuticals, hereinafter "isopregol"); menthone glycerol ketals (FEMA 3807, tradename FRESCOLAT® type MGA); 3-1-menthoxypropane-1,2-diol (from Takasago, FEMA 3784); and menthyl lactate; (from Haarman & Reimer, FEMA 3748, tradename FRESCOLAT® type ML), WS-30, WS-14, Eucalyptus extract (p-Mehtha-3,8-Diol), Menthol (its natural or synthetic derivatives), Menthol PG carbonate, Menthol EG carbonate, Menthol glyceryl ether, N-tertbutyl-p-menthane-3-carboxamide, P-menthane-3-carboxylic acid glycerol ester, Methyl-2-isopryl-bicyclo (2.2.1), Heptane-2-carboxamide; and Menthol methyl ether, and menthyl pyrrolidone carboxylate among others. These and other suitable cooling agents are further described in the following U.S. patents, all of which are incorporated in their entirety by reference hereto: U.S. Pat. Nos. 4,230,688; 4,032,661; 4,459,425; 4,136,163; 5,266,592; 6,627,233.

In some embodiments, warming components may be selected from a wide variety of compounds known to provide the sensory signal of warming to the user. These compounds offer the perceived sensation of warmth, particularly in the oral cavity, and often enhance the perception of flavors, sweeteners and other organoleptic components. In some embodiments, useful warming compounds can include vanillyl alcohol n-butylether (TK-1000) supplied by Takasago Perfumary Company Limited, Tokyo, Japan, vanillyl alcohol n-propylether, vanillyl alcohol isopropylether, vanillyl alcohol isobutylether, vanillyl alcohol n-aminoether, vanillyl alcohol isoamyleather, vanillyl alcohol n-hexyleather, vanillyl alcohol methylether, vanillyl alcohol ethylether, gingerol, shogaol, paradol, zingerone, capsaicin, dihydrocapsaicin, nordihydrocapsaicin, homocapsaicin, homodihydrocapsaicin, ethanol, isopropyl alcohol, iso-amylalcohol, benzyl alcohol, glycerine, and combinations thereof.

In some embodiments, a tingling sensation can be provided. One such tingling sensation is provided by adding jambu, oleoresin, or spilanthol to some examples. In some embodiments, alkylamides extracted from materials such as jambu or sanshool can be included. Additionally, in some embodiments, a sensation is created due to effervescence. Such effervescence is created by combining an alkaline material with an acidic material. In some embodiments, an alkaline material can include alkali metal carbonates, alkali metal bicarbonates, alkaline earth metal carbonates, alkaline earth metal bicarbonates and mixtures thereof. In some embodiments, an acidic material can include acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof. Examples of "tingling" type sensates can be found in U.S. Pat. No. 6,780,443, the entire contents of which are incorporated herein by reference for all purposes.

Sensate components may also be referred to as "trigeminal stimulants" such as those disclosed in U.S. Patent Application No. 205/0202118, which is incorporated herein by reference. Trigeminal stimulants are defined as an orally consumed product or agent that stimulates the trigeminal nerve. Examples of cooling agents which are trigeminal stimulants include menthol, WS-3, N-substituted p-menthane carboxamide, acyclic carboxamides including WS-23, methyl succinate, menthone glycerol ketals, bulk sweeteners such as xylitol, erythritol, dextrose, and sorbitol, and combinations thereof. Trigeminal stimulants can also include flavors, tingling agents, Jambu extract, vanillyl alkyl ethers, such as vanillyl n-butyl ether, spilanthol, Echinacea extract, Northern Prickly Ash extract, capsaicin, capsicum oleoresin, red pepper oleoresin, black pepper oleoresin, piperine, ginger oleoresin, gingerol, shoagol, cinnamon oleoresin, cassia oleoresin, cinnamic aldehyde, eugenol, cyclic acetal of vanillin and menthol glycerin ether, unsaturated amides, and combinations thereof.

In some embodiments, sensate components are used at levels that provide a perceptible sensory experience i.e. at or above their threshold levels. In other embodiments, sensate components are used at levels below their threshold levels such that they do not provide an independent perceptible sensory experience. At subthreshold levels, the sensates may provide an ancillary benefit such as flavor or sweetness enhancement or potentiation.

Breath Freshening Ingredients

Breath fresheners can include essential oils as well as various aldehydes, alcohols, and similar materials. In some embodiments, essential oils can include oils of spearmint, peppermint, wintergreen, sassafras, chlorophyll, citral, geraniol, cardamom, clove, sage, carvacrol, eucalyptus, cardamom, magnolia bark extract, marjoram, cinnamon, lemon, lime, grapefruit, and orange. In some embodiments, aldehydes such as cinnamic aldehyde and salicylaldehyde can be used. Additionally, chemicals such as menthol, carvone, iso-garrigol, and anethole can function as breath fresheners. Of these, the most commonly employed are oils of peppermint, spearmint and chlorophyll.

In addition to essential oils and chemicals derived from them, in some embodiments breath fresheners can include but are not limited to zinc citrate, zinc acetate, zinc fluoride, zinc ammonium sulfate, zinc bromide, zinc iodide, zinc chloride, zinc nitrate, zinc fluorosilicate, zinc gluconate, zinc tartarate, zinc succinate, zinc formate, zinc chromate, zinc phenol sulfonate, zinc dithionate, zinc sulfate, silver nitrate, zinc salicylate, zinc glycerophosphate, copper nitrate, chlorophyll, copper chlorophyll, chlorophyllin, hydrogenated cottonseed oil, chlorine dioxide, beta cyclodextrin, zeolite, silica-based materials, carbon-based materials, enzymes such as laccase, and combinations thereof.

In some embodiments, the release profiles of probiotics can be managed for a confectionery including, but not limited to lactic acid producing microorganisms such as *Bacillus coagulans, Bacillus subtilis, Bacillus laterosporus, Bacillus laevolacticus, Sporolactobacillus inulinus, Lactobacillus acidophilus, Lactobacillus curvatus, Lactobacillus plantarum, Lactobacillusjenseni, Lactobacillus casei, Lactobacillusfermentumn, Lactococcus lactis, Pedioccocus acidilacti, Pedioccocus pentosaceus, Pedioccocus urinae, Leuconostoc mesenteroides, Bacillus coagulans, Bacillus subtilis, Bacillus laterosporus, Bacillus laevolacticus, Sporolactobacillus inulinus* and mixtures thereof. Breath fresheners are also known by the following trade names: Retsyn,™ Actizol,™ and Nutrazin.™ Examples of malodor-controlling compositions are also included in U.S. Pat. No. 5,300,305 to Stapler et al. and in U.S. Patent Application Publication Nos. 2003/0215417 and 2004/0081713 which are incorporated in their entirety herein by reference for all purposes.

Dental Care Ingredients

Dental care ingredients (also known as oral care ingredients) may include but are not limited to tooth whiteners, stain removers, oral cleaning, bleaching agents, desensitizing agents, dental remineralization agents, antibacterial agents, anticaries agents, plaque acid buffering agents, surfactants and anticalculus agents. Non-limiting examples of such ingredients can include, hydrolytic agents including proteolytic enzymes, abrasives such as hydrated silica, calcium carbonate, sodium bicarbonate and alumina, other active stain-removing components such as surface-active agents, including, but not limited to anionic surfactants such as sodium stearate, sodium palminate, sulfated butyl oleate, sodium oleate, salts of fumaric acid, glycerol, hydroxylated lecithin, sodium lauryl sulfate and chelators such as polyphosphates, which are typically employed as tartar control ingredients. In some embodiments, dental care ingredients can also include tetrasodium pyrophosphate and sodium tri-polyphosphate, sodium bicarbonate, sodium acid pyrophosphate, sodium tripolyphosphate, xylitol, sodium hexametaphosphate.

In some embodiments, peroxides such as carbamide peroxide, calcium peroxide, magnesium peroxide, sodium peroxide, hydrogen peroxide, and peroxydiphospate are included. In some embodiments, potassium nitrate and potassium citrate are included. Other examples can include casein glycomacropeptide, calcium casein peptone-calcium phosphate, casein phosphopeptides, casein phosphopeptide-amorphous calcium phosphate (CPP-ACP), and amorphous calcium phosphate. Still other examples can include papaine, krillase, pepsin, trypsin, lysozyme, dextranase, mutanase, glycoamylase, amylase, glucose oxidase, and combinations thereof.

Further examples can include surfactants such as sodium stearate, sodium ricinoleate, and sodium lauryl sulfate surfactants for use in some embodiments to achieve increased prophylactic action and to render the dental care ingredients more cosmetically acceptable. Surfactants can preferably be detersive materials which impart to the composition detersive and foaming properties. Suitable examples of surfactants are water-soluble salts of higher fatty acid monoglyceride monosulfates, such as the sodium salt of the monosulfated monoglyceride of hydgrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine.

In addition to surfactants, dental care ingredients can include antibacterial agents such as, but not limited to, triclosan, chlorhexidine, zinc citrate, silver nitrate, copper, limonene, and cetyl pyridinium chloride. In some embodiments, additional anticaries agents can include fluoride ions or fluorine-providing components such as inorganic fluoride salts. In some embodiments, soluble alkali metal salts, for example, sodium fluoride, potassium fluoride, sodium fluorosilicate, ammonium fluorosilicate, sodium monofluorophosphate, as well as tin fluorides, such as stannous fluoride and stannous chloride can be included. In some embodiments, a fluorine-containing compound having a beneficial effect on the care and hygiene of the oral cavity, e.g., diminution of enamel solubility in acid and protection of the teeth against decay may also be included as an ingredient. Examples thereof include sodium fluoride, stannous fluoride, potassium fluoride, potassium stannous fluoride (SnF.sub.2-KF), sodium hexafluorostannate, stannous chlorofluoride, sodium fluorozirconate, and sodium monofluorophosphate. In some embodiments, urea is included.

Further examples are included in the following U.S. patents and U.S. published patent applications, the contents of all of which are incorporated in their entirety herein by reference for all purposes: U.S. Pat. No. 5,227,154 to Reynolds, U.S. Pat. No. 5,378,131 to Greenberg, U.S. Pat. No. 6,846,500 to Luo et al., U.S. Pat. No. 6,733,818 to Luo et al., U.S. Pat. No. 6,696,044 to Luo et al., U.S. Pat. No. 6,685,916 to Holme et al., U.S. Pat. No. 6,485,739 to Luo et al., U.S. Pat. No. 6,479,071 to Holme et al., U.S. Pat. No. 6,471,945 to Luo et al., U.S. Patent Publication Nos. 20050025721 to Holme et al., 2005008732 to Gebreselassie et al., and 20040136928 to Holme et al.

Active Ingredients

Actives generally refer to those ingredients that are included in a delivery system and/or confectionery composition for the desired end benefit they provide to the user. In some embodiments, actives can include medicaments, nutrients, nutraceuticals, herbals, nutritional supplements, pharmaceuticals, drugs, and the like and combinations thereof.

Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocryptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of active ingredients contemplated for use in some embodiments can include antacids, H2-antagonists, and analgesics. For example, antacid dosages can be prepared using the ingredients calcium carbonate alone or in combination with magnesium hydroxide, and/or aluminum hydroxide. Moreover, antacids can be used in combination with H2-antagonists.

Analgesics include opiates and opiate derivatives, such as Oxycontin™, ibuprofen, aspirin, acetaminophen, and combinations thereof that may optionally include caffeine.

Other drug active ingredients for use in embodiments can include anti-diarrheals such as Immodium™ AD, anti-histamines, anti-tussives, decongestants, vitamins, and breath fresheners. Also contemplated for use herein are anxiolytics such as Xanax™; anti-psychotics such as Clozaril™ and Haldol™; non-steroidal anti-inflammatories (NSAID's) such as ibuprofen, naproxen sodium, Voltaren™ and Lodine™, anti-histamines such as Claritin™, Hismanal™, Relafen™, and Tavist™; anti-emetics such as Kytril™ and Cesamet™; bronchodilators such as Bentolin™, Proventil™; anti-depressants such as Prozac™, Zoloft™, and Paxil™; anti-migraines such as Imigra™, ACE-inhibitors such as Vasotec™, Capoten™ and Zestril™; anti-Alzheimer's agents, such as Nicergoline™; and CaH-antagonists such as Procardia™, Adalat™, and Calan™.

The popular H2-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients can include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

A variety of nutritional supplements may also be used as active ingredients including virtually any vitamin or mineral. For example, vitamin A, vitamin C, vitamin D, vitamin E, vitamin K, vitamin $B_6$, vitamin $B_{12}$, thiamine, riboflavin, biotin, folic acid, niacin, pantothenic acid, sodium, potassium, calcium, magnesium, phosphorus, sulfur, chlorine, iron, copper, iodine, zinc, selenium, manganese, choline, chromium, molybdenum, fluorine, cobalt and combinations thereof, may be used.

Examples of nutritional supplements that can be used as active ingredients are set forth in U.S. Patent Application Publication Nos. 2003/0157213 A1, 2003/0206993 and 2003/0099741 A1 which are incorporated in their entirety herein by reference for all purposes.

Various herbals may also be used as active ingredients such as those with various medicinal or dietary supplement properties, Herbals are generally aromatic plants or plant parts and or extracts thereof that can be used medicinally or for flavoring. Suitable herbals can be used singly or in various mixtures. Commonly used herbs include Echinacea, Goldenseal, Calendula, Rosemary, Thyme, Kava Kava, Aloe, Blood Root, Grapefruit Seed Extract, Black Cohosh, Ginseng, Guarana, Cranberry, Gingko Biloba, St. John's Wort, Evening Primrose Oil, Yohimbe Bark, Green Tea, Ma Huang, Maca, Bilberry, Lutein, and combinations thereof.

Effervescing System Ingredients

An effervescent system may include one or more edible acids and one or more edible alkaline materials. The edible acid(s) and the edible alkaline material(s) may react together to generate effervescence.

In some embodiments, the alkaline material(s) may be selected from, but is not limited to, alkali metal carbonates, alkali metal bicarbonates, alkaline earth metal carbonates, alkaline earth metal bicarbonates, and combinations thereof. The edible acid(s) may be selected from, but is not limited to, citric acid, phosphoric acid, tartaric acid, malic acid, ascorbic acid, and combinations thereof. In some embodiments, an effervescing system may include one or more other ingredients such as, for example, carbon dioxide, oral care ingredients, flavorants, etc.

For examples of use of an effervescing system in a chewing confectionery, refer to U.S. Provisional Patent No. 60/618,222 filed Oct. 13, 2004, and entitled "Effervescent Pressed Confectionery Tablet Compositions," the contents of which are incorporated herein by reference for all purposes. Other examples can be found in U.S. Pat. No. 6,235,318, the contents of which are incorporated herein by reference for all purposes.

Appetite Suppressor Ingredients

Appetite suppressors can be ingredients such as fiber and protein that function to depress the desire to consume food. Appetite suppressors can also include benzphetamine, diethylpropion, mazindol, phendimetrazine, phentermine, hoodia (P57), Olibra,™ ephedra, caffeine and combinations thereof. Appetite suppressors are also known by the following trade names: Adipex,™ Adipost,™ Bontril™ PDM, Bontril™ Slow Release, Didrex,™ Fastin,™ Ionamin,™ Mazanor,™ Melfiat,™ Obenix,™ Phendiet,™ Phendiet-105,™ Phentercot,™ Phentride,™ Plegine,™ Prelu-2,™ Pro-Fast,™ PT 105,™ Sanorex,™ Tenuate,™ Sanorex,™ Tenuate,™ Tenuate Dospan,™ Tepanil Ten-Tab,™ Teramine,™ and Zantryl.™ These and other suitable appetite suppressors are further described in the following U.S. patents, all of which are incorporated in their entirety by reference hereto: U.S. Pat. No. 6,838,431 to Portman, U.S. Pat. No. 6,716,815 to Portman, U.S. Pat. No. 6,558,690 to Portman, U.S. Pat. No. 6,468,962 to Portman, U.S. Pat. No. 6,436,899 to Portman.

Potentiator Ingredients

Potentiators can consist of materials that may intensify, supplement, modify or enhance the taste and/or aroma perception of an original material without introducing a characteristic taste and/or aroma perception of their own. In some embodiments, potentiators designed to intensify, supplement, modify, or enhance the perception of flavor, sweetness, tartness, umami, kokumi, saltiness and combinations thereof can be included.

In some embodiments, examples of suitable potentiators, also known as taste potentiators include, but are not limited to, neohesperidin dihydrochalcone, chlorogenic acid, alapyridaine, cynarin, miraculin, glupyridaine, pyridinium-betain compounds, glutamates, such as monosodium glutamate and monopotassium glutamate, neotame, thaumatin, tagatose, trehalose, salts, such as sodium chloride, monoammonium glycyrrhizinate, vanilla extract (in ethyl alcohol), sugar acids, potassium chloride, sodium acid sulfate, hydrolyzed vegetable proteins, hydrolyzed animal proteins, yeast extracts, adenosine monophosphate (AMP), glutathione, nucleotides, such as inosine monophosphate, disodium inosinate, xanthosine monophosphate, guanylate monophosphate, alapyridaine (N-(1-carboxyethyl)-6-(hydroxymethyl)pyridinium-3-ol inner salt, sugar beet extract (alcoholic extract), sugarcane leaf essence (alcoholic extract), curculin, strogin, mabinlin, gymnemic acid, hydroxybenzoic acids, 3-hydrobenzoic acid, 2,4-dihydrobenzoic acid, citrus aurantium, vanilla oleoresin, sugarcane leaf essence, maltol, ethyl maltol, vanillin, licorice glycyrrhizinates, compounds that respond to G-protein coupled receptors (T2Rs and T1Rs) and taste potentiator compositions that impart kokumi, as disclosed in U.S. Pat. No. 5,679,397 to Kuroda et al., which is incorporated in its entirety herein by reference. "Kokumi" refers to materials that impart "mouthfulness" and "good body".

Sweetener potentiators, which are a type of taste potentiator, enhance the taste of sweetness. In some embodiments, exemplary sweetener potentiators include, but are not limited to, monoammonium glycyrrhizinate, licorice glycyrrhizinates, citrus aurantium, alapyridaine, alapyridaine (N-(1-carboxyethyl)-6-(hydroxymethyl)pyridinium-3-ol) inner salt, miraculin, curculin, strogin, mabinlin, gymnemic acid, cynarin, glupyridaine, pyridinium-betain compounds, sugar beet extract, neotame, thaumatin, neohesperidin dihydrochalcone, hydroxybenzoic acids, tagatose, trehalose, maltol, ethyl maltol, vanilla extract, vanilla oleoresin, vanillin, sugar beet extract (alcoholic extract), sugarcane leaf essence (alcoholic extract), compounds that respond to G-protein coupled receptors (T2Rs and T1Rs) and combinations thereof.

Additional examples of potentiators for the enhancement of salt taste include acidic peptides, such as those disclosed in U.S. Pat. No. 6,974,597, herein incorporated by reference. Acidic peptides include peptides having a larger number of acidic amino acids, such as aspartic acid and glutamic acid, than basic amino acids, such as lysine, arginine and histidine. The acidic peptides are obtained by peptide synthesis or by subjecting proteins to hydrolysis using endopeptidase, and if necessary, to deamidation. Suitable proteins for use in the production of the acidic peptides or the peptides obtained by subjecting a protein to hydrolysis and deamidation include plant proteins, (e.g. wheat gluten, corn protein (e.g., zein and gluten meal), soybean protein isolate), animal proteins (e.g., milk proteins such as milk casein and milk whey protein, muscle proteins such as meat protein and fish meat protein, egg white protein and collagen), and microbial proteins (e.g., microbial cell protein and polypeptides produced by microorganisms).

The sensation of warming or cooling effects may also be prolonged with the use of a hydrophobic sweetener as described in U.S. Patent Application Publication 2003/0072842 A1 which is incorporated in its entirety herein by reference. For example, such hydrophobic sweeteners include those of the formulae I-XI as set forth below:

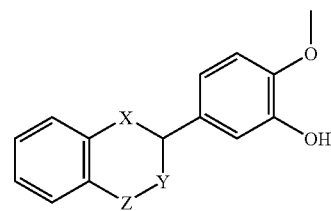

I wherein X, Y and Z are selected from the group consisting of $CH_2$, O and S;

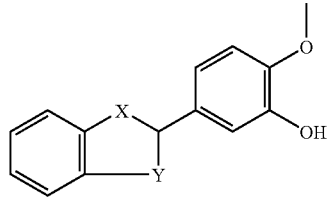

II wherein X and Y are selected from the group consisting of S and O;

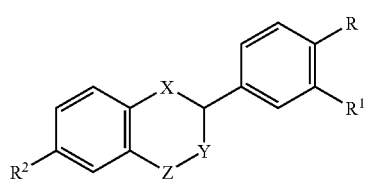

III wherein X is S or O; Y is O or $CH_2$; Z is $CH_2$, $SO_2$ or S; R is $OCH_3$, OH or H; $R^1$ is SH or OH and $R^2$ is H or OH;

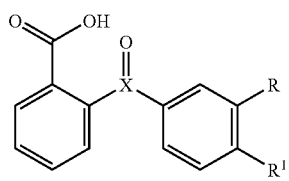

IV wherein X is C or S; R is OH or H and $R^1$ is $OCH_3$ or OH;

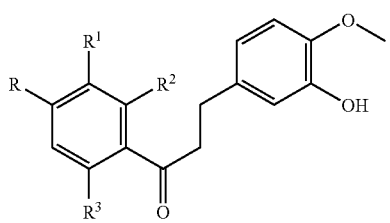

V wherein R, $R^2$ and $R^3$ are OH or H and $R^1$ is H or COOH;

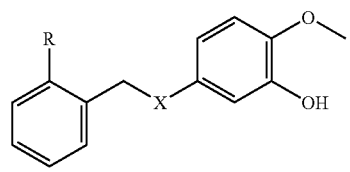

VI wherein X is O or $CH_2$ and R is COOH or H;

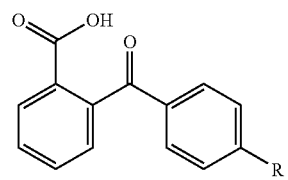

VII wherein R is $CH_3CH_2$, OH, $N(CH_3)_2$ or Cl;

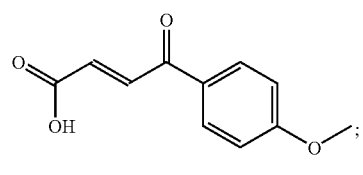

VIII

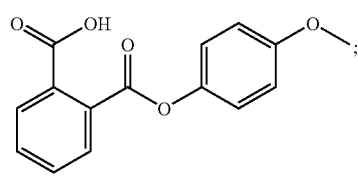

IX

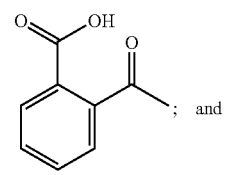

X

; and

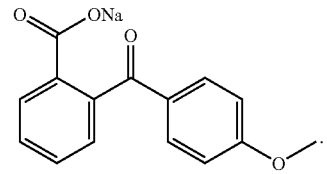

XI

Perillartine may also be added as described in U.S. Pat. No. 6,159,509 also incorporated in its entirety herein by reference.

Food Acid Ingredients

Acids can include, but are not limited to acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof.

Micronutrient Ingredients

Micronutrients can include materials that have an impact on the nutritional well being of an organism even though the quantity required by the organism to have the desired effect is small relative to macronutrients such as protein, carbohydrate, and fat. Micronutrients can include, but are not limited to vitamins, minerals, enzymes, phytochemicals, antioxidants, and combinations thereof.

In some embodiments, vitamins can include fat soluble vitamins such as vitamin A, vitamin D, vitamin E, and vitamin K and combinations thereof. In some embodiments, vitamins can include water soluble vitamins such as vitamin C (ascorbic acid), the B vitamins (thiamine or $B_1$, riboflavoin or $B_2$, niacin or $B_3$, pyridoxine or $B_6$, folic acid or $B_9$, cyanocobalimin or $B_{12}$, pantothenic acid, biotin), and combinations thereof.

In some embodiments minerals can include but are not limited to sodium, magnesium, chromium, iodine, iron, manganese, calcium, copper, fluoride, potassium, phosphorous, molybdenum, selenium, zinc, and combinations thereof.

In some embodiments micronutrients can include but are not limited to L-carnitine, choline, coenzyme Q10, alpha-lipoic acid, omega-3-fatty acids, pepsin, phytase, trypsin, lipases, proteases, cellulases, and combinations thereof.

Antioxidants can include materials that scavenge free radicals. In some embodiments, antioxidants can include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

In some embodiments phytochemicals can include but are not limited to cartotenoids, chlorophyll, chlorophyllin, fiber, flavanoids, anthocyanins, cyaniding, delphinidin, malvidin, pelargonidin, peonidin, petunidin, flavanols, catechin, epicatechin, epigallocatechin, epigallocatechingallate (EGCG), theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

Mouth Moistening Ingredients

Mouth moisteners can include, but are not limited to, saliva stimulators such as acids and salts and combinations thereof. In some embodiments, acids can include acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof. In some embodiments, salts can include sodium chloride, calcium chloride, potassium chloride, magnesium chloride, sea salt, sodium citrate, and combinations thereof.

Mouth moisteners can also include hydrocolloid materials that hydrate and may adhere to oral surface to provide a sensation of mouth moistening. Hydrocolloid materials can include naturally occurring materials such as plant exudates, seed confectionerys, and seaweed extracts or they can be chemically modified materials such as cellulose, starch, or natural confectionery derivatives. In some embodiments, hydrocolloid materials can include pectin, gum arabic, acacia gum, alginates, agar, carageenans, guar gum, xanthan gum, locust bean gum, gelatin, gellan gum, galactomannans, tragacanth gum, karaya gum, curdlan, konjac, chitosan, xyloglucan, beta glucan, furcellaran, gum ghatti, tamarin, bacterial gums, and combinations thereof. Additionally, in some embodiments, modified natural gums such as propylene glycol alginate, carboxymethyl locust bean gum, low methoxyl pectin, and their combinations can be included. In some embodiments, modified celluloses can be included such as microcrystalline cellulose, carboxymethlcellulose (CMC), methylcellulose (MC), hydroxypropylmethylcellulose (HPCM), and hydroxypropylcellulose (MPC), and combinations thereof.

Similarly, humectants which can provide a perception of mouth hydration can be included. Such humectants can include, but are not limited to glycerol, sorbitol, polyethylene glycol, erythritol, and xylitol. Additionally, in some embodiments, fats can provide a perception of mouth moistening. Such fats can include medium chain triglycerides, vegetable oils, fish oils, mineral oils, and combinations thereof.

Throat Care Ingredients

Throat soothing ingredients can include analgesics, anesthetics, demulcents, antiseptic, and combinations thereof. In some embodiments, analgesics/anesthetics can include menthol, phenol, hexylresorcinol, benzocaine, dyclonine hydrochloride, benzyl alcohol, salicyl alcohol, and combinations thereof. In some embodiments, demulcents can include but are not limited to slippery elm bark, pectin, gelatin, and combinations thereof. In some embodiments, antiseptic ingredients can include cetylpyridinium chloride, domiphen bromide, dequalinium chloride, and combinations thereof.

In some embodiments, antitussive ingredients such as chlophedianol hydrochloride, codeine, codeine phosphate, codeine sulfate, dextromethorphan, dextromethorphan hydrobromide, diphenhydramine citrate, and diphenhydramine hydrochloride, and combinations thereof can be included.

In some embodiments, throat soothing agents such as honey, propolis, aloe vera, glycerine, menthol and combinations thereof can be included. In still other embodiments, cough suppressants can be included. Such cough suppressants can fall into two groups: those that alter the consistency or production of phlegm such as mucolytics and expectorants; and those that suppress the coughing reflex such as codeine (narcotic cough suppressants), antihistamines, dextromethorphan and isoproterenol (non-narcotic cough suppressants). In some embodiments, ingredients from either or both groups can be included.

In still other embodiments, antitussives can include, but are not limited to, the group consisting of codeine, dextromethorphan, dextrorphan, diphenhydramine, hydrocodone, noscapine, oxycodone, pentoxyverine and combinations thereof. In some embodiments, antihistamines can include, but are not limited to, acrivastine, azatadine, brompheniramine, chlorpheniramine, clemastine, cyproheptadine, dexbrompheniramine, dimenhydrinate, diphenhydramine, doxylamine, hydroxyzine, meclizine, phenindamine, phenyltoloxamine, promethazine, pyrilamine, tripelennamine, triprolidine and combinations thereof. In some embodiments, non-sedating antihistamines can include, but are not limited to, astemizole, cetirizine, ebastine, fexofenadine, loratidine, terfenadine, and combinations thereof.

In some embodiments, expectorants can include, but are not limited to, ammonium chloride, guaifenesin, ipecac fluid extract, potassium iodide and combinations thereof. In some embodiments, mucolytics can include, but are not limited to, acetylcycsteine, ambroxol, bromhexine and combinations thereof. In some embodiments, analgesic, antipyretic and anti-inflammatory agents can include, but are not limited to, acetaminophen, aspirin, diclofenac, diflunisal, etodolac, fenoprofen, flurbiprofen, ibuprofen, ketoprofen, ketorolac, nabumetone, naproxen, piroxicam, caffeine and mixtures thereof. In some embodiments, local anesthetics can include, but are not limited to, lidocaine, benzocaine, phenol, dyclonine, benzonotate and mixtures thereof.

In some embodiments nasal decongestants and ingredients that provide the perception of nasal clearing can be included. In some embodiments, nasal decongestants can include but are not limited to phenylpropanolamine, pseudoephedrine, ephedrine, phenylephrine, oxymetazoline, and combinations thereof. In some embodiments ingredients that provide a perception of nasal clearing can include but are not limited to menthol, camphor, borneol, ephedrine, eucalyptus oil, peppermint oil, methyl salicylate, bornyl acetate, lavender oil, wasabi extracts, horseradish extracts, and combinations thereof. In some embodiments, a perception of nasal clearing can be provided by odoriferous essential oils, extracts from woods, confectionerys, flowers and other botanicals, resins, animal secretions, and synthetic aromatic materials.

Coloring Ingredients

In some embodiments, one or more colors can be included. As classified by the United States Food, Drug, and Cosmetic Act (21 C.F.R. 73), colors can include exempt from certification colors (sometimes referred to as natural even though they can be synthetically manufactured) and certified colors (sometimes referred to as artificial), or combinations thereof. In some embodiments, exempt from certification or natural colors can include, but are not limited to annatto extract, (E160b), bixin, norbixin, astaxanthin, dehydrated beets (beet powder), beetroot red/betanin (E162), ultramarine blue, canthaxanthin (E161g), cryptoxanthin (E161c), rubixanthin (E161d), violanxanthin (E161e), rhodoxanthin (E161f), caramel (E150(a-d)), β-apo-8'-carotenal (E160e), β-carotene (E160a), alpha carotene, gamma carotene, ethyl ester of beta-apo-8 carotenal (E160f), flavoxanthin (E161a), lutein (E161b), cochineal extract (E120); carmine (E132), carmoisine/azorubine (E122), sodium copper chlorophyllin (E141), chlorophyll (E140), toasted partially defatted cooked cottonseed flour, ferrous gluconate, ferrous lactate, grape color extract, grape skin extract (enocianina), anthocyanins (E163), haematococcus algae meal, synthetic iron oxide, iron oxides and hydroxides (E172), fruit juice, vegetable juice, dried algae meal, tagetes (Aztec marigold) meal and extract, carrot oil, corn endosperm oil, paprika, paprika oleoresin, phaffia yeast, riboflavin (E101), saffron, titanium dioxide, turmeric (E100), turmeric oleoresin, amaranth (E123), capsanthin/capsorbin (E160c), lycopene (E160d), and combinations thereof.

In some embodiments, certified colors can include, but are not limited to, FD&C blue #1, FD&C blue #2, FD&C green #3, FD&C red #3, FD&C red #40, FD&C yellow #5 and FD&C yellow #6, tartrazine (E102), quinoline yellow (E104), sunset yellow (E110), ponceau (E124), erythrosine (E127), patent blue V (E131), titanium dioxide (E171), aluminium (E173), silver (E174), gold (E175), pigment rubine/lithol rubine BK (E180), calcium carbonate (E170), carbon black (E153), black PN/brilliant black BN (E151), green S/acid brilliant green BS (E142), and combinations thereof. In some embodiments, certified colors can include FD&C aluminum lakes. These consist of the aluminum salts of FD&C dyes extended on an insoluble substrate of alumina hydrate. Additionally, in some embodiments, certified colors can be included as calcium salts.

Multiple Ingredients

In some embodiments, a delivery system or confectionery composition may include two or more ingredients for which managed release from the confectionery composition during consumption of the confectionery composition is desired. In some embodiments, the ingredients may be encapsulated or otherwise included separately in different delivery systems. Alternatively, in some embodiments the ingredients may be encapsulated or otherwise included in the same delivery system. As another possibility, one or more of the ingredients may be free (e.g., unencapsulated) while one or more other ingredients may be encapsulated. Additionally, the multiple ingredients can be included in different portions of a confectionery composition.

A confectionery composition may include a group of ingredients for which managed release of the group during consumption of the confectionery composition is desired. Groups of two or more ingredients for which managed release from a confectionery composition during consumption of the confectionery composition may be desired include, but are not limited to: color and flavor, multiple flavors, multiple colors, cooling agent and flavor, warming agent and flavor, cooling agent and warming agent, cooling agent and high intensity sweetener, warming agent and high intensity sweetener, multiple cooling agents (e.g., WS-3 and WS-23, WS-3 and menthyl succinate), menthol and one or more cooling agents, menthol and one or more warming agents, multiple warming agents, high intensity sweetener(s) and tooth whitening active(s), high intensity sweetener(s) and breath freshening active(s), an ingredient with some bitterness and a bitterness suppressor for the ingredient, multiple high intensity sweeteners (e.g., ace-k and aspartame), multiple tooth whitening actives (e.g., an abrasive ingredient and an antimicrobial ingredient, a peroxide and a nitrate, a warming agent and a polyol, a cooling agent and a polyol, multiple polyols, a warming agent and micronutrient, a cooling agent and a micronutrient, a warming agent and a mouth moistening agent, a cooling agent and a mouth moistening agent, a warming agent and a throat care agent, a cooling agent and a throat care agent, a warming agent and a food acid, a cooling agent and food acid, a warming agent and an emulsifier/surfactant, a cooling agent and an emulsifier/surfactant, a warming agent and a color, a cooling agent and a color, a warming agent and a flavor potentiator, a cooling agent and a flavor potentiator, a warming agent with sweetness potentiator, a cooling agent with a sweetness potentiator, a warming agent and an appetite suppressant, a cooling agent and an appetite suppressant, a high intensity sweetener and a flavor, a cooling agent and a teeth whitening agent, a warming agent and a teeth whitening agent, a warming agent and breath freshening agent, a cooling agent and a breath freshening agent, a cooling agent and an effervescing system, a warming agent and an effervescing system, a warming agent and an antimicrobial agent, a cooling agent and an antimicrobial agent, multiple anticalculus ingredients, multiple remineralization ingredients, multiple surfactants, remineralization ingredients with demineralization ingredients, acidic ingredients with acid buffering ingredients, anticalculus ingredients with antibacterial ingredients, remineralization ingredients with anticalculus ingredients, anticalculus ingredients with remineralization ingredients with antibacterial ingredients, surfactant ingredients with anticalculus ingredients, surfactant ingredients with antibacterial ingredients, surfactant ingredients with remineralization ingredients, surfactants with anticalculus ingredients with antibacterial ingredients, multiple types of vitamins or minerals, multiple micronutrients, multiple acids, multiple antimicrobial ingredients, multiple breath freshening ingredients, breath freshening ingredients and antimicrobial ingredients, multiple appetite suppressors, acids and bases that react to effervesce, a bitter compound with a high intensity sweetener, a cooling agent and an appetite suppressant, a warming agent and an appetite suppressant, a high intensity sweetener and an appetite suppressant, a high intensity sweetener with an acid, a probiotic ingredient and a prebiotic ingredient, a vitamin and a mineral, a metabolic enhancement ingredient with a macronutrient, a metabolic enhancement ingredient with a micronutrient, an enzyme with a substrate, a high intensity sweetener with a sweetness potentiator, a cooling compound with a cooling potentiator, a flavor with a flavor potentiator, a warming compound with a warming potentiator, a flavor with salt, a high intensity sweetener with salt, an acid with salt, a cooling compound with salt, a warming compound with salt, a flavor with a surfactant, an astringent compound with an ingredient to provide a sensation of hydration, etc. In some embodiments, the multiple ingredients may be part of the same delivery system or may be part of different delivery systems. Different delivery systems may use the same or different encapsulating materials.

In some embodiments, encapsulation of the multiple ingredients will result in a delay in the release of the predominant amount of the multiple ingredients during consumption of a confectionery composition that includes the encapsulated multiple ingredients (e.g., as part of a delivery system added as an ingredient to the confectionery composition). This may be particularly helpful in situations wherein separate encapsulation of the ingredients may cause them to release with different release profiles. For example, different high intensity sweeteners may have different release profiles because they have different water solubilities or differences in other characteristics. Encapsulating them together may cause them to release more simultaneously.

In some embodiments, the release profile of the multiple ingredients can be managed for a confectionery composition by managing various characteristics of the multiple ingredients, the delivery system containing the multiple ingredients, and/or the portion of the confectionery composition containing the delivery system and/or how the delivery system is made in a manner as previously discussed above.

The additional components, as described above, may be used in any portion of the confectionery composition such as in the cooked saccharide portion, the elastomeric portion, the coating, or the center-fill as desired. Suitable amounts for the additional components are set forth in Table 2, above. The amounts in Table 2 generally apply to each of the additional components as they may be added to a confectionery composition in a free form, i.e., unencapsulated. In some embodiments, where the additional component is provided in an encapsulated form, an amount greater than those amounts as set forth in Table 2 may be used due to the modified release profile of the additional component. Also, because many of the additional components shown in Table 2 are optional, the amounts represent amounts used when the component is selected for inclusion in the composition. In other words, the lower limit of 0% is not included even though the additional component is an optional component.

The components listed in Table 2, above, may be added to any portion of the confectionery composition in their encapsulated and/or unencapsulated forms, as well as in combination with any of the other optional components. For example, a single component may be added to a confectionery composition in its encapsulated and unencapsulated forms. The two different forms of the component may be added to the same or different portions of the confectionery composition the same or different amounts.

In some embodiments, a single component may be added in two or more different encapsulated forms. In particular, two or more different encapsulating materials, such as different polymers, may be used to encapsulate two or more separate portions of the component. The different encapsulated forms of the same component may be added to the same or different portions of the confectionery composition in the same or different amounts. Further, in some embodiments, an unencapsulated form of the same component may be added in combination with the two or more different encapsulated forms. The unencapsulated form of the component may be added to any portion of the confectionery composition in the same or different amount from the encapsulated forms. Moreover, some embodiments may add an unencapsulated form of a similar component in combination with the two or more different encapsulated forms. For example, two encapsulated forms of a single sweetener may be used in combination with an unencapsulated form of a different sweetener.

In some embodiments, combinations of two or more different components from Table 2, above, may be employed. In some embodiments, at least one of the components may be encapsulated, while at least one of the components may be unencapsulated. The multiple components may be the same type of component, e.g., two different sweeteners, or components from distinctly different categories, e.g., a sweetener and a warming agent. The different components may be added to the same or different portions of the confectionery composition in the same or different amounts.

Some embodiments may include multiple components from Table 2, above, each of which is encapsulated. The multiple encapsulated components may be included in the same or different portions of the confectionery composition in the same or different amounts. The multiple encapsulated components may be the same type of component or from distinctly different categories.

In some embodiments in which multiple encapsulated components are added to the confectionery composition, the multiple components may be encapsulated together or separately. In embodiments in which the multiple components are encapsulated together, the components may be mixed together and encapsulated by a single encapsulating material. In embodiments in which the multiple components are encapsulated separately, the material used to encapsulate the components may be the same or different. The amounts provided for the components are based on the specified portion in which the component is contained.

As described above, Table 2 provides a list of components which may optionally be present in one or more portions of the confectionery product. Suitable amounts which may be present in the coating, center-fill, cooked saccharide portion, or elastomeric portion are provided in the table. The amounts in Table 2 are provided as ppm or weight % in a portion or layer of the confectionery product. Table 2 is only representative and is not be construed to limit the ingredients that can be included in the confectionery composition portions in any way.

Processing

Confectionery compositions can be created by mixing the cooked saccharide portion as described with compositions creating the elastomeric portion using any technique known in the art. For example, mixers including, but not limited to, sigma blade mixers, Hobart mixers, etc. can be used to blend specified proportions of the compositions. In some embodiments, a confectionery composition is formed by blending 5%-95% w/w of a cooked saccharide composition together with 5%-95% w/w of an elastomeric composition. In some embodiments, the composition representing the larger proportion of the confectionery composition is metered or loaded into the mixer first. Then, the composition representing the smaller proportion of the confectionery composition is added to the mixer, with mixing and the final confectionery composition is removed from the mixer once a homogeneous mass is achieved. Depending on the nature of the cooked saccharide and elastomeric compositions, the mixer may involve different mixing actions. In some embodiments, a highly distributive mixer supplying vigorous mixing action can be used while in other embodiments, a less intense mixer supplying gentle mixing action can be used.

In some embodiments, the cooked saccharide component can be created by applying a heat process that increases the solids content of the cooked saccharide component by removing moisture from an aqueous saccharide syrup. In other embodiments, the cooked saccharide component can be created by increasing the solids content of a saccharide syrup without a heat process such as by incorporating solid saccharides into an aqueous saccharide syrup.

In some embodiments, the confectionery composition is created using a continuous process. In some embodiments, a continuous process employing an extruder is used to blend the cooked saccharide composition and the elastomeric portion. As with batch processes, the nature of the cooked saccharide and elastomeric compositions dictates the type of mixing elements used in the extruder. In some embodiments, highly distributive mixing elements can be used while in other embodiments, less intensive mixing can be used.

As with the mixing operation, confectionery product forming operations can include any technique known in the art. In some embodiments, the confectionery product can be formed using rolling and scoring operations, cut and wrap operations, chain die operations, or any other confectionery or chewing confectionery forming operation. Additionally, in some embodiments, the viscosity of the confectionery composition can be low enough to employ confectionery depositing operations.

In some embodiments, cost savings may arise because the confectionery compositions can be processed using equipment designed for confectionery compositions such as hard and soft candies. Additionally, in some embodiments, confectionery compositions may be processed without the need for some chewing confectionery unit operations such as rolling and scoring and conditioning. Further, in some embodiments, the confectionery compositions demonstrate shelf life stability that negates the need for moisture resistant packaging.

In some embodiments, cost savings may arise because a cooked saccharide portion contains an amount of water that substitutes for more expensive components such as those in an elastomeric portion.

In some embodiments, cost savings may arise because a cooked saccharide composition can include a higher amount of a cheaper material. For example, in some embodiments, a starch can be used to replace sucrose and/or corn syrup.

The confectionery compositions with optional coating and/or center-fill may be formed by any technique known in the art which includes the method described by U.S. Pat. No. 6,280,780 to Degady et al. ("Degady") which is hereby incorporated in its entirety for all purposes. Degady describes an apparatus and method for forming center-filled confectionery pellets. The method includes first extruding a liquid-filled rope of a confectionery layer and passing the rope through a sizing mechanism including a series of pairs of pulley-shaped roller members. The roller members "size" the rope or strand of confectionery material such that it leaves the series of rollers with the desired size and shape for entering a tablet-forming mechanism. In some embodiments, the confectionery compositions described herein form the confectionery layer of Degady.

The rope is then led into a tablet-forming mechanism including a pair of rotating chain die members which are endless chain mechanisms and both rotate at the same speed by a motor and gear mechanism. Each of the chain mechanisms include a plurality of open curved die groove members which mate and form die cavities in which the pieces of confectionery composition material (pellets or tablets) are formed. While Degady is limited to the formation of pellet or tablet shaped pieces, the confectionery pieces may be of other shapes as described above. The shape of the die groove members may be altered to provide any desired shape.

The confectionery composition may optionally be passed through a cooling tunnel either before entering the tablet-forming mechanism, after exiting the tablet-forming mechanism or both. Cooling of the rope prior to entering the tablet-forming mechanism may be beneficial to prevent rebound of the individual pieces and thus may provide an increase in productivity.

The cooled pieces of confectionery composition material can then be fed into a storage container for conditioning and further processing. At this point, the cooled pieces of confectionery material could also be fed directly into a coating tunnel mechanism, such as a rotating tunnel mechanism.

Whether the pieces of formed confecteriony material are first stored, transported in a storage container, or fed directly into a coating tunnel or mechanism, the individual pieces of confectionery material may subsequently be subjected to a conventional sugar or sugarless coating process in order to form a hard exterior shell on the confectionery composition material. A variety of coating processes or mechanisms of this type are known. In some embodiments, the coating is applied in numerous thin layers of material in order to form an appropriate uniform coated and finished quality surface on the confectionery products. The hard coating material, which may include sugar, maltitol, erythritol, isomalt, sorbitol or any other polyol, including those described herein, and optionally flavoring, is sprayed onto the pellets of confectionery composition material as they pass through a coating mechanism or a coating tunnel and are tumbled and rotated therein. In addition, conditioned air is circulated or forced into the coating tunnel or mechanism in order to dry each of the successive coating layers on the formed products. In some embodiments, the coating, or outermost portion, can be formed by lamination, dual or multiple extrusion, or any other process that creates an outermost portion.

In some embodiments, an outermost layer, coating, or shell is formed by enrobing the confectionery composition. Enrobing can include the steps of submerged a confectionery composition piece in a quantity of enrobing material. In some embodiments, a confectionery composition can be enrobed in a fat-based material such as chocolate, compound coating or the like.

The coating composition may range from about 2% to about 80%, more specifically, about 20% to about 40% by weight of an individual confectionery composition piece which includes a cooked saccharide portion, an elastomeric portion and optionally a center-fill; even more specifically, from 25% to 35% and still more specifically around 30%. The coating may include sugar or polyol such as maltitol as the primary component, but may also include flavors, colors, etc. as described below in the discussion of the elastomeric portion. The coating or outermost portion may be crystalline or amorphous.

In addition to forming a confectionery composition product, in some embodiments, the confectionery compositions as described herein can become components of other compositions. For example, in some embodiments, a confectionery composition including a cooked saccharide portion and an elastomeric portion can become one of a plurality of layers in a confectionery product.

The features and advantages of the present invention are more fully shown by the following examples which are provided for purposes of illustration, and are not to be construed as limiting the invention in any way.

EXAMPLES

The following examples 100-120 in Table 1 are directed to inventive confectionery compositions of some embodiments. These examples are directed to sucrose-based compositions. Examples 200-330 in Tables 2 and 3 are directed to polyol-based compositions. Example 500 in Table 4 is directed to a soft textured composition.

Individual confectionery pieces of any of these examples may be optionally center filled with liquid, semi-liquid, or solid fillings and they may be optionally coated. Furthermore, the shape of the confectionery pieces may be chosen from any shape such as ball, pellet, chunk, slab, etc.

Examples 100-120

TABLE 1

| | % w/w | | |
|---|---|---|---|
| Component | 100 | 110 | 120 |
| Granulated sugar | 43.40 | 44.50 | 45.20 |
| Glucose Syrup | 35.50 | 36.50 | 37.00 |
| Color | 0.20 | 0.20 | 0.20 |
| Flavor | 1.80 | 1.80 | 1.60 |
| High Intensity Sweetener | | 0.30 | 0.44 |
| Gum Base* | 19.10 | 16.70 | 15.56 |
| Total | 100.00 | 100.00 | 100.00 |

*Gum Base may include, but is not limited to, elastomer, plasticizer, and filler For Examples 100-130, a saccharide solution is prepared by dissolving the granulated sugar and corn syrup in water. The color is then dissolved in water and a color solution is added to the saccharide solution. Next, the saccharide and color solutions are cooked to 145C to form a candy mass. The candy mass is then placed on a cooling table where the flavor is mixed in. The high intensity sweeteners can be added to this candy mass at the same time the flavor is added. Alternatively, the high intensity sweeteners can be added to the gum base component that forms the elastomeric portion. Once the flavor (and possibly the high intensity sweetener) is dispersed in the candy mass, the gum base is heated to 70-90C and kneaded into the flavored candy mass to form a homogeneous confectionery mass. Lastly, the homogeneous confectionery mass is shaped into finished product pieces. One method of shaping is to pass the confectionery mass through a drop roller to form finished product pieces.

Examples 200-330

TABLE 2

| | % w/w | | | | | | | | |
|---|---|---|---|---|---|---|---|---|---|
| Component | 200 | 210 | 220 | 230 | 240 | 250 | 260 | 270 | 280 |
| Isomalt | 80.00 | 55.00 | 35.00 | 60.00 | 71.67 | 63.33 | 73.33 | 66.67 | 48.33 |
| Flavor | 2.50 | 2.50 | 2.50 | 2.50 | 2.50 | 2.50 | 2.50 | 2.50 | 2.50 |
| Gum Base* | 15.00 | 40.00 | 40.00 | 15.00 | 23.33 | 31.67 | 15.00 | 15.00 | 40.00 |
| Powdered Isomalt | | | | | | | | | |
| Powdered Sorbitol | | | 20.00 | 20.00 | | | 6.67 | 13.33 | 6.67 |
| Aspartame | 2.00 | 2.00 | 2.00 | 2.00 | 2.00 | 2.00 | 2.00 | 2.00 | 2.00 |
| Acesulfame-K | 0.50 | 0.50 | 0.50 | 0.50 | 0.50 | 0.50 | 0.50 | 0.50 | 0.50 |
| Total | | | | | | | | | |

*Gum Base may include, but is not limited to, elastomer, plasticizer, and filler

Examples 290-330

TABLE 3

| | % w/w | | | | |
|---|---|---|---|---|---|
| Component | 290 | 300 | 310 | 320 | 330 |
| Isomalt | 41.67 | 43.33 | 51.67 | 57.50 | 59.73 |
| Flavor | 2.50 | 2.50 | 2.50 | 2.50 | 1.49 |
| Gum Base* | 40.00 | 31.67 | 23.33 | 27.50 | 22.00 |
| Powdered Isomalt | | | | | 15.00 |
| Powdered Sorbitol | 13.33 | 20.00 | 20.00 | 10.00 | |
| Aspartame | 2.00 | 2.00 | 2.00 | 2.00 | 1.43 |
| Acesulfame-K | 0.50 | 0.50 | 0.50 | 0.50 | 0.35 |
| Total | 100.00 | 100.00 | 100.00 | 100.00 | 100.00 |

*Gum Base may include, but is not limited to, elastomer, plasticizer, and filler For Examples 200-330, a cooked saccharide solution is prepared by dissolving the isomalt in water and cooking to 172C to form a candy mass. Alternatively, the isomalt can be melted by heating to 172C without water to form a candy mass. Next, the candy mass is placed on a cooling table where the flavor and powdered isomalt or powdered sorbitol are mixed in. The high intensity sweeteners can be added to the candy mass at the same time the flavor is added. Alternatively, the high intensity sweeteners can be added to the gum base component that forms an elastomeric portion. Once the flavor (and possibly the high intensity sweetener) is dispersed in the candy mass, the gum base is heated to 70-90C and kneaded into the flavored candy mass to form a homogeneous confectionery mass. Lastly, the homogeneous confectionery mass is shaped into finished product pieces. One method of shaping is to pass the confectionery mass through a drop roller to form finished product pieces.

Example 500

TABLE 4

| Component | % w/w |
|---|---|
| Granular Sugar | 15.00-22.00 |
| Glucose Syrup | 20.00-25.00 |
| Gelatin Solution | 3.00-6.00 |
| Fat Mixture | 8.00-12.00 |
| Fondant | 6.00-10.00 |
| Food Acid Blend | 0.75-2.50 |
| Flavor | 0.80-1.80 |
| Color | 0.01-0.10 |

TABLE 4-continued

| Component | % w/w |
|---|---|
| High Intensity Sweetener | 0.75-3.00 |
| Gum Base* | 15.00-45.00 |

*Gum Base may include, but is not limited to, elastomer, plasticizer, and filler To prepare a confectionery product with a softer texture, texture modifying agents such as fat and hydrocolloids may be included. In Example 500, a fat blend of hydrogenated vegetable fats is added along with a hydrated gelatin blend. To prepare the confectionery product, the sugar and corn syrup are first dissolved in water and heated to 172C. Separately, the gelatin is dissolved in hot water and added to the hot sugar syrup. Next, the fat is added to the cooked sugar syrup and the mass is placed on a cooling table. Once on the cooling table, fondant, color, and flavor are worked into the candy to form a candy mass. High intensity sweetener can be added to the candy on the cooling table or it can be added to the gum base component that forms an elastomeric portion. The gum base component is heated to 50-65C and mixed with the candy mass to form a confectionery mass. Lastly, the confectionery mass is shaped into finished product pieces. One method of shaping is to pass the confectionery mass through a drop roller.

What is claimed is:

1. A soft textured multi-component confectionery composition, comprising:
    a first portion, said first portion including a cooked saccharide component comprising isomalt, 3-6% w/w of hydrated gelatin, and 8-12% w/w of a fat based on the weight of the soft textured multi-component confectionery composition; and
    a second portion, said second portion including an elastomeric component;
    wherein at least one of said first portion and said second portion comprises at least one first ingredient, wherein the first ingredient is a flavor; and
    wherein said first portion and said second portion form a mixture.

2. The confectionery composition of claim 1, wherein said second portion includes a gum base.

3. The confectionery composition of claim 1, wherein at least a portion of said at least one first ingredient is encapsulated.

4. The confectionery composition of claim 1, further including a coating.

5. The confectionery composition of claim 1, further including a center-fill.

6. The confectionery composition of claim 5, wherein said center-fill includes at least one of a liquid, a powder, and a combination thereof.

7. The confectionery composition of claim 1, comprising a cooked sugar component.

8. The confectionery composition of claim 1, further comprising at least one sweetener potentiator.

9. The confectionery composition of claim 1, further comprising a high intensity sweetener.

10. A soft textured multi-component confectionery composition, comprising:
    a first portion, said first portion including a cooked saccharide component comprising isomalt, 3-6% w/w of a hydrated gelatin, and 8-12% w/w of a fat based on the weight of the soft textured multi-component confectionery composition; and
    a second portion, said second portion including an elastomeric component;
    wherein said soft textured multi-component confectionery composition comprises at least one first ingredient wherein the first ingredient is a flavor; and at least one second ingredient wherein the second ingredient is a flavor; and
    wherein said first portion and said second portion form a mixture.

11. The confectionery composition of claim 10, wherein said first portion comprises said first ingredient and said second portion comprises said second ingredient.

12. The confectionery composition of claim 10, wherein said first ingredient and said second ingredient are the same.

13. The confectionery composition of claim 10, wherein said first ingredient and said second ingredient are two different flavors.

14. The confectionery composition of claim 10, wherein said first ingredient and said second ingredient are complementary.

15. The confectionery composition of claim 10, wherein said first ingredient and said second ingredient are two flavors opposed to each other.

16. The confectionery composition of claim 10, wherein at least a portion of at least one of said first ingredient and said second ingredient is encapsulated.

17. The confectionery composition of claim 10, wherein said first ingredient is encapsulated and said second ingredient is unencapsulated.

18. The confectionery composition of claim 10, wherein said first ingredient and said second ingredient have different intensities, wherein said first ingredient and said second ingredient are two flavors.

19. The confectionery composition of claim 10, wherein during consumption of said soft textured confectionery composition, said first ingredient releases earlier in the chew than said second ingredient.

20. A soft textured multi-component confectionery composition, comprising:
    a first portion, said first portion including a cooked saccharide component comprising isomalt, 3-6% w/w of a hydrated gelatin, and 8-12% w/w of a fat based on the weight of the soft textured multi-component confectionery composition; and
    a second portion, said second portion including an elastomeric component;
    wherein said soft textured multi-component confectionery composition comprises at least one first ingredient wherein the first ingredient is a flavor; at least one second ingredient wherein the second ingredient is a flavor; and at least one third ingredient wherein the third ingredient is a flavor; and
    wherein said first portion and said second portion form a mixture.

21. The confectionery composition of claim 1, wherein at least one of said first portion and said second portion comprises at least one second ingredient selected from the group consisting of flavors, food acids, functional ingredients, sensates and sweeteners.

22. The confectionery composition of claim 10, wherein at least one of said first portion and said second portion comprises at least one third ingredient selected from the group consisting of flavors, food acids, functional ingredients, sensates and sweeteners.

23. The confectionery composition of claim 20, wherein at least one of said first portion and said second portion comprises at least one fourth ingredient selected from the group consisting of flavors, food acids, functional ingredients, sensates and sweeteners.

24. The confectionery composition of claim 1, wherein all of the flavor of the composition is in the first portion, and wherein the flavor is present in an amount of 0.01 to 10% based on the total weight of the cooked saccharide portion.

25. The confectionery composition of claim 10, wherein all of the flavor of the composition is in the first portion, and wherein each flavor is present in an amount of 0.01 to 10% based on the total weight of the cooked saccharide portion.

26. The confectionery composition of claim 20, wherein all of the flavor of the composition is in the first portion, and wherein each flavor is present in an amount of 0.01 to 10% based on the total weight of the cooked saccharide portion.

* * * * *